(12) United States Patent
Honda

(10) Patent No.: US 6,242,928 B1
(45) Date of Patent: Jun. 5, 2001

(54) METHOD AND APPARATUS FOR DETECTING RESISTANCE OF OXYGEN CONCENTRATION SENSOR

(75) Inventor: Takayoshi Honda, Nagoya (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/226,221

(22) Filed: Jan. 7, 1999

(30) Foreign Application Priority Data

Jan. 16, 1998 (JP) .................................................. 10-007061
Jan. 20, 1998 (JP) .................................................. 10-008926
Feb. 18, 1998 (JP) .................................................. 10-036071

(51) Int. Cl.[7] .................................................. G01R 27/08
(52) U.S. Cl. .......................................... 324/713; 324/71.1
(58) Field of Search .................................. 324/439, 693, 324/713, 71.1

(56) References Cited

U.S. PATENT DOCUMENTS 4,803,866 * 2/1989 Miki et al. ........................... 73/23.32
5,833,836 * 11/1998 Takami et al. ........................ 204/424
6,084,418 * 7/2000 Takami et al. ........................ 324/713

FOREIGN PATENT DOCUMENTS 9-292364   11/1997 (JP).

* cited by examiner

Primary Examiner—Glenn W. Brown
(74) Attorney, Agent, or Firm—Nixon & Vanderhye P.C.

(57) ABSTRACT

The resistance of an air-fuel-ratio sensor element is determined from current detected before changing an applied voltage to the sensor and current detected when a predetermined period elapses after changing the applied voltage to the sensor. A resistance detector includes operational amplifiers, resistors and transistors. The applied voltage is changed by switching the transistors to more accurately detect a resistance value.

17 Claims, 22 Drawing Sheets

| Y' | Ty |
|---|---|
| 0 | — |
| 4 | 450 |
| 6 | 475 |
| 10 | 500 |
| 16 | 525 |
| 23 | 550 |
| 32 | 575 |
| 44 | 600 |
| 57 | 625 |

METHOD AND APPARATUS FOR DETECTING RESISTANCE OF OXYGEN CONCENTRATION SENSOR

BACKGROUND OF THE INVENTION

1. Field of the Invention

The present invention relates to an oxygen concentration sensor for the exhaust gas of an engine. More specifically, the present invention relates to:

- detecting the impedance (that is, the alternating-current impedance) or the admittance of the oxygen concentration sensor;
- an oxygen-concentration detecting apparatus which detects the resistance of the oxygen concentration sensor; and
- detecting the temperature of the oxygen concentration sensor according to its resistance component.

2. Description of Related Art

In recent years, there has been a demand for an increased control accuracy and a demand for a change to lean burning in control of the air-fuel ratio of an engine used in a vehicle. In response to such demands, there has been provided a linear air-fuel-ratio sensor or an oxygen concentration sensor capable of detecting the air-fuel ratio of mixed air supplied to the engine or the concentration of oxygen contained in exhausted gas which varies with the current flowing through sensor linearly over a wide range.

In order to maintain a high detection accuracy of such an air-fuel-ratio sensor, it is necessary to keep the sensor in an activated state. In general, in order to sustain the activated state of the air-fuel-ratio sensor, it is necessary to heat the sensor element by controlling the current supply to a heater attached to the sensor.

Regarding such current-supply control to the heater, there has been developed a conventional technology of implementing feedback control whereby the temperature of the sensor element is detected and adjusted to a desired activation temperature of typically about 700 degrees Celsius(° C.). The temperature of the sensor element is referred to simply as an element temperature. As a possible technique to detect the element temperature from time to time, a temperature sensor may be attached to the sensor element. The element temperature is then derived from output by the temperature sensor. With such a technique, however, the sensor will become large in size and its cost will rise.

In order to solve the problem described above, there has been proposed a technique whereby the impedance of the sensor element which is also referred to hereafter simply as an element impedance is detected instead of the element temperature. The element temperature can then be found from the detected element impedance by using a known relation between the element temperature and the element impedance. It should be noted that a result of detection of the element impedance can also be used for, among other purposes, determining the degree of deterioration of the air-fuel-ratio sensor.

With the conventional element-impedance detecting apparatus, however, the element impedance can not be detected accurately in some cases.

Furthermore, as a technique of detecting element impedance of an air-fuel-ratio sensor of the limit-current type for example, a voltage Vneg is applied to a resistance-dominant zone not including a limit-current zone, and a current Ineg flowing through the sensor as a result of the application of the voltage Vneg is measured. The element impedance is then found as a ratio of the voltage Vneg to the current Ineg as follows:

Element impedance=$V_{neg}/I_{neg}$

According to another technique of detecting an element impedance, an applied voltage is lowered or raised, and a decrease or an increase in flowing current resulting from the decrease or the raise in applied voltage is measured. The element impedance (alternating-current element impedance), is determined by the decrease or increase in applied voltage and the decrease or increase in the flowing current.

According to the conventional technologies, however, conversion from an element impedance to an element temperature may cause an error, and the detection accuracy of the element temperature may be compromised. This problem of a poor detection accuracy is explained as follows. A relation between the element impedance and the element temperature shown in FIG. 25 is known. The vertical axis of FIG. 25 represents the impedance count value obtained as a result of LSB conversion of a detected element impedance. As shown in the figure, the impedance count value is not inversely proportional to the element temperature. Particularly, in the zone of low element temperatures, the impedance count value increases abruptly as the element temperature decreases.

In the activation-temperature zone, on the other hand, a difference of 1 count in impedance count value corresponds to a large difference in element temperature. In an activation-temperature zone of the sensor element, for example, the following relations between the impedance count value and the element temperature exist. When the impedance count value changes from 26 to 25, the derived element temperature substantially changes from 746 degrees Celsius to 750 degrees Celsius. Likewise, when the impedance count value changes from 25 to 24, the derived element temperature greatly changes from 750 degrees Celsius to 760 degrees Celsius. Accordingly, such large change in the element temperature causes a problem that the element temperature is not detected accurately.

SUMMARY OF THE INVENTION

The present invention is made in light of the foregoing problems, and it is an object of the present invention to provide an element-resistance-component detecting apparatus for an oxygen concentration sensor and an oxygen-concentration detecting apparatus, having a simple configuration capable of detecting the element resistance component of an oxygen concentration sensor with a high degree of accuracy.

It is another object of the present invention to provide an element temperature detection apparatus for a gas concentration sensor, which can improve the accuracy of element-temperature detection.

According to an aspect of the present invention, an applied-voltage changing means changes a voltage output of a voltage applying means in order to detect the element resistance component of an oxygen concentration sensor. The voltage applying means applies a voltage to the oxygen concentration sensor for detecting the concentration of oxygen in an object gas. Before the applied-voltage changing means changes the oxygen-concentration-detection voltage output by the voltage applying means, a first current detecting means detects a current flowing through the oxygen concentration sensor.

Then, when a predetermined period of time has elapsed after the applied-voltage changing means starts the operation to change the oxygen-concentration-detection voltage outputted by the voltage applying means, a second current detecting means detects the current flowing through the oxygen concentration sensor. Subsequently, a resistor-element calculating means calculates an element resistance component of the oxygen concentration sensor from a difference between a current detected by the first current detecting means and a current detected by the second current detecting means.

That is, the element resistance component of the oxygen concentration sensor is calculated from a difference between a current flowing through the oxygen concentration sensor before changing the oxygen-concentration-detection voltage and a current which flows through the sensor after the predetermined period of time has elapsed after the start of the operation to change the oxygen-concentration-detection voltage.

The voltage applying means includes:
  an output circuit for outputting a voltage supplied to an input terminal of the output circuit to the oxygen concentration sensor;
  a constant-voltage circuit for supplying a first predetermined constant voltage, to the input terminal of the output circuit through an output resistor; and
  a voltage switching circuit having a voltage dividing resistor and a switching device, which are connected in series between a signal line from the output resistor to the input terminal of the output circuit and a first terminal having a second predetermined voltage.

Thus, if the switching device employed in the voltage switching circuit in the configuration described above is put in a turned-off state, the first predetermined constant voltage generated by the constant-voltage circuit is outputted to the oxygen concentration sensor. If the switching device employed in the voltage switching circuit is put in a turned-on state, on the other hand, a divided voltage is outputted to the oxygen concentration sensor. The divided voltage is obtained by dividing the voltage difference between the first predetermined constant voltage and the second predetermined voltage with a ratio of the resistance of the voltage dividing resistor to the resistance of the output resistor.

The applied-voltage changing means changes the oxygen-concentration-detection voltage, that is, the voltage applied to the oxygen concentration sensor, by switching the switching device.

According to the resistance component detecting apparatus for the oxygen concentration sensor of the present invention, when the applied-voltage changing means changes the oxygen-concentration-detection voltage output by the voltage applying means by switching the switching device, the oxygen-concentration-detection voltage output by the voltage applying means changes quickly. Thus, the second current detecting means is capable of detecting the sensor current accurately when a predetermined period of time has elapsed after the oxygen-concentration-detection voltage applied to the oxygen concentration sensor starts changing. As a result, by virtue of the element resistance component of the oxygen concentration sensor, it is possible to change the oxygen-concentration-detection voltage applied to the oxygen concentration sensor without a delay and, hence, to detect the element resistance component of the sensor with a high degree of accuracy with a simple configuration.

According to another aspect of the present invention, the oxygen-concentration-detection voltage applied to the sensor element of the oxygen concentration sensor is temporarily increased or decreased, and an element resistance is calculated as an admittance from a voltage changing amount and a current changing amount caused by such voltage change. Then, the element temperature is determined based on the calculated admittance.

Accordingly, in the detection of an element resistance, the admittance Y, that is, the reciprocal of an element impedance, is calculated as follows:

$$Y = \Delta I / \Delta V$$

where notation $\Delta I$ is a change in current and notation $\Delta V$ is a change in voltage. In this specification, by the way, the technical term "element resistance" is used to include "element impedance" and "element admittance".

Thus, an element resistance is determined from the admittance which has a proportional relationship with element temperature. Accordingly, the element temperature is determined by the admittance, and thereby improving the detection accuracy.

BRIEF DESCRIPTION OF THE DRAWINGS

Other features and advantages of the present invention will be appreciated, as well as methods of operation and the function of the related parts, from a study of the following detailed description, the appended claims and the drawings, all of which form a part of this application. In the drawings:

DETAILED DESCRIPTION OF PREFERRED EMBODIMENTS

An air-fuel-ratio detecting apparatus of the present invention will now be described in reference to the accompanying drawings. The air-fuel-ratio detecting apparatus of embodiments of the present invention is employed in an electronically controlled gasoline-injection engine for an automobile, and an air-fuel-ratio control system of the engine controls the injection volume of fuel injected to the engine to achieve a desired air-fuel ratio on the basis of a detection result obtained by the air-fuel-ratio detecting apparatus. The following description explains details of configuration and processing for an air-fuel ratio detection by means of an air-fuel-ratio sensor and detection of the element resistance component, that is, the element admittance or the element impedance, of the sensor.

(First Embodiment)

Figure 1:
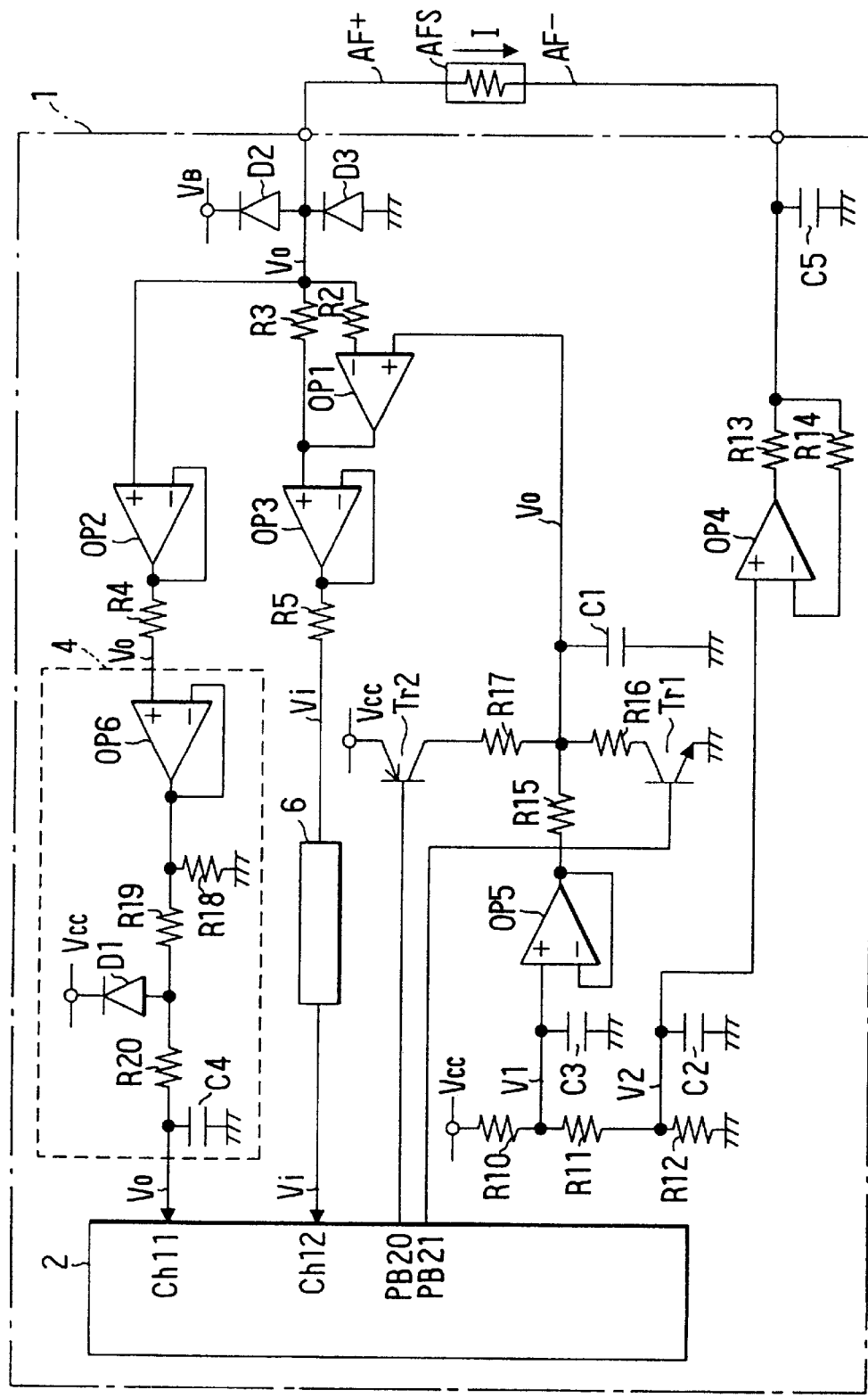
FIG. 1 is a circuit diagram showing an air-fuel-ratio detecting apparatus according to a first embodiment of the present invention.

FIG. 1 is a circuit diagram showing an air-fuel-ratio detecting apparatus 1 implemented by a first embodiment.

Figure 2:
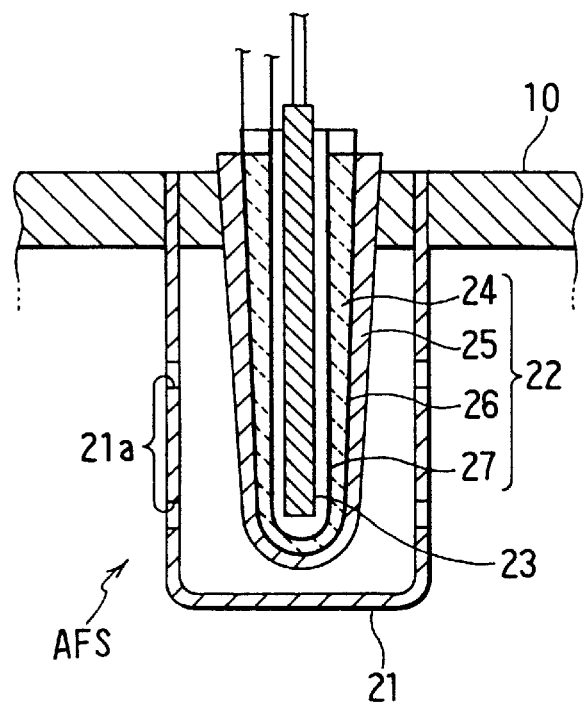
FIG. 2 is a sectional view of an air-fuel-ratio sensor employed in the air-fuel-ratio detecting apparatus according to the first through sixth embodiments of the present invention.

As shown in FIG. 1, an air-fuel-ratio sensor AFS of the limit-current type is connected to the air-fuel-ratio detecting apparatus 1 as an oxygen concentration sensor. The air fuel ratio sensor AFS is installed in an exhaust pipe 10 as shown in FIG. 2. When an oxygen-concentration-detection voltage is applied to the air-fuel-ratio sensor AFS, a sensor current, proportional to the concentration of oxygen contained in gas exhausted through the exhaust pipe 10, flows through the sensor AFS.

FIG. 2 is a sectional view showing the configuration of the air-fuel-ratio sensor AFS. As shown in FIG. 2, the air-fuel-ratio sensor AFS protrudes toward the inner side of the exhaust pipe 10, comprising main components such as a cover 21, a sensor main body 22 and a heater 23. The cover 21 has a U-shaped cross section. A number of apertures 21a are formed on the wall of the cover 21 to provide paths between the inside and the outside of the cover 21. The sensor main body 22 generates limit current corresponding to the concentration of oxygen contained in a lean region of the air-fuel ratio or the concentration of unburned gas such as CO, HC and H2 in a rich region of the air-fuel ratio.

The configuration of the sensor main body 22 will now be explained in detail. An exhaust-gas-side electrode layer 26 is fixed to the outer surface of a solid electrolyte layer 24 having a cross section with a shape resembling a cup. On the inner surface of a solid electrolyte layer 24, on the other hand, an atmosphere-side electrode layer 27 is fixed. On the outer side of the exhaust-gas-side electrode layer 26, a diffusion-resistance layer 25 is created by using a technique such as a plasma spraying method.

The solid electrolyte layer 24 is an oxygen-ion conducting oxide sintered body made by dissolving a stabilizer such as CaO, MgO, Y2O3 or Yb2O3 in an oxide such as ZrO2, HfO2, ThO2 or Bi2O3. The diffusion-resistance layer 25 is made of a heat resistant inorganic material such as alumina, magnesia, quartzite, spinel or mullite. The exhausted-gas-side electrode layer 26 and the atmosphere-side electrode layer 27 are each made of a precious metal with a high catalyst activity such platinum. On the surfaces of the layers 26 and 27, porous chemical plating is applied. It should be noted that the area and the thickness of the exhausted-gas-side electrode layer 26 have values in the range 10 to 100 square mm and 0.5 to 2.0 microns respectively. On the other hand, the area and the thickness of the atmosphere-side electrode layer 27 have a value of 10 square mm or greater and a value in the range 0.5 to 2.0 microns respectively.

Accommodated in the atmosphere-side electrode layer 27, the heater 23 generates heat. Thermal energy of the heat generated by the heater raises the temperature of the sensor main body 22 which comprises the exhaust-gas-side electrode layer 26, the solid electrolyte layer 24, the atmosphere-side electrode layer 27 and the diffusion-resistance layer 25. The heater 23 has a heat generating capacity sufficient for activating the sensor main body 22.

In the air-fuel-ratio sensor AFS having a configuration described above, the sensor main body 22 generates a limit current corresponding to the concentration of oxygen contained in a zone leaner than a stoichiometric air-fuel ratio point (lean region). In this case, the magnitude of the limit current corresponding to the concentration of oxygen is determined by the area of the exhausted-gas-side electrode layer 26, the thickness of the diffusion-resistance layer 25, the porosity and the average aperture diameter.

While the sensor main body 22 is capable of detecting the concentration of oxygen which varies linearly with the current flowing through the sensor, it is necessary to raise the temperature of the sensor main body 22 to about 600 degrees Celsius or higher in order to activate the sensor main body 22.

In addition, since the activation-temperature range of the sensor main body 22 is narrow, the temperature of the sensor main body 22 can not be controlled to a value in the activation range by merely heating the sensor main body 22 using gas exhausted by the engine. For this reason, the temperature of the sensor main body 22 is raised and controlled to a value in the activation-temperature range by heating using the heater 23. It should be noted that, in a region richer than the stoichiometric air-fuel ratio, the concentration of unburned gas such as carbon mono-oxide (CO) varies approximately linear with the air-fuel ratio, and the sensor main body 22 generates a limit current corresponding to the concentration of unburned gas such as carbon mono-oxide.

Figure 3:
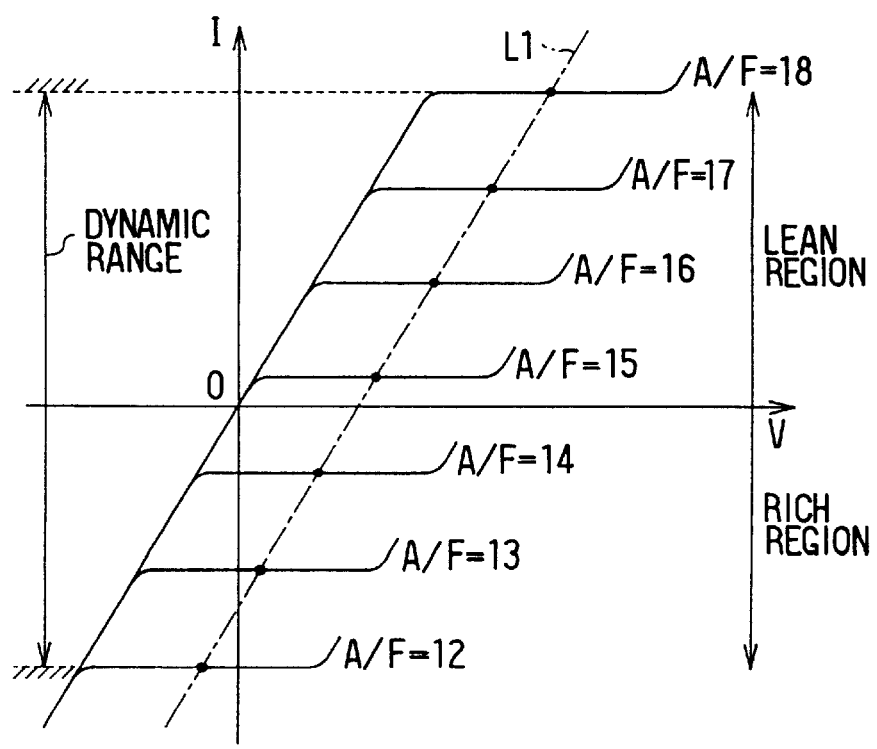
FIG. 3 is a graph showing voltage-current characteristics of the air-fuel-ratio sensor according to the first through sixth embodiments of the present invention.

A voltage-current characteristic of the sensor main body 22 of the air-fuel-ratio sensor AFS is explained by referring to FIG. 3. The segment of each curve parallel to the voltage axis V (flat portion) is the so-called limit current generated by the sensor main body 22. The current flowing into the solid electrolyte layer 24 of the sensor main body 22 is linearly proportional to the voltage applied to the solid electrolyte layer 24. An increase and decrease of the limit current (sensor current) correspond to an increase and decrease of the air-fuel ratio (that is, lean and rich). That is, the more the air-fuel ratio is shifted to the lean side, the greater the magnitude of the limit current, and the more the air-fuel ratio is shifted to the rich side, the smaller the magnitude of the limit current.

In the voltage-current characteristic shown in FIG. 3, a region of voltages lower than voltage levels corresponding to the limit current (flat portion) is the so-called resistance-dominant region. The gradient of a straight linear line in this resistance-dominant region represents the internal impedance or the element impedance of the solid electrolyte layer 24 of the sensor main body 22. The element impedance changes in accordance with the temperature change. Therefore, when the temperature of the sensor main body 22 decreases, the element impedance increases, and the gradient of the linear line decreases.

As shown in FIG. 1, the air-fuel-ratio detecting apparatus 1 to which the air-fuel-ratio sensor AFS is connected is provided with a microcomputer 2 having an embedded A/D converter. Two terminals ch11 and ch12 of the microcomputer 2 are input terminals of the A/D converter. On the other hand, 2 other terminals PB20 and PB21 of the microcomputer 2 are terminals of an ordinary output port of the microcomputer 2.

In addition, the air-fuel-ratio detecting apparatus 1 also includes operational amplifiers OP1, OP2, OP3 and OP4 as well as input circuits 4 and 6. An inverting input terminal of the operational amplifier OP1 is connected to a plus-side terminal AF+ of the air-fuel-ratio sensor AFS by a resistor R2. The plus-side terminal AF+ is a terminal connected to the atmosphere-side electrode layer 27 shown in FIG. 2. An output terminal of the operational amplifier OP1 is connected to the plus-side terminal AF+ of the air-fuel-ratio sensor AFS by a shunt resistor R3. A non-inverting input terminal of the operational amplifier OP2 is connected directly to the plus-side terminal AF+ of the air-fuel-ratio sensor AFS. An output terminal and an inverting input terminal of the operational amplifier OP2 are connected to each other. An input terminal of the input circuit 4 is connected to the output terminal of the operational amplifier OP2 by a resistor R4. An output terminal of the input circuit 4 is connected directly to the input terminal ch11 of the microcomputer 2. A non-inverting input terminal of the operational amplifier OP3 is connected directly to the output terminal of the operational amplifier OP1. An output terminal and an inverting input terminal of the operational amplifier OP3 are connected to each other. The output terminal of the operational amplifier OP3 is connected to the input terminal of the input circuit 6 by a resistor R5. An output terminal of the input circuit 6 is connected directly to the input terminal ch12 of the microcomputer 2.

Enclosed by a dashed line in FIG. 1, the input circuit 4 includes an operational amplifier OP6 which serves as a buffer. A non-inverting input terminal of the operational amplifier OP6 is used as the input terminal of the input circuit 4. An output terminal and an inverting input terminal of the operational amplifier OP6 are connected to each other. A pull-down resistor R18 is connected between the output terminal of the operational amplifier OP6 and a ground potential GND of 0 V. One end of a resistor R19 is connected to the output terminal of the operational amplifier OP6 and the other end of the resistor R19 is connected to an anode of a diode D1 serving as an over-voltage protection component. A cathode of the diode D1 is connected to a power-supply voltage VCC which is set at a level of 5V in the case of this embodiment. One end of a resistor R20 is used as the output terminal of the input circuit 4 and the other end of the resistor R20 is connected to the anode of the diode D1. Used for eliminating noise, a capacitor C4 is connected between the output terminal of the input circuit 4 and the ground potential GND. As described above, the input terminal of the input circuit 4, that is, the non-inverting input terminal of the operational amplifier OP6, is connected to the output terminal of the operational amplifier OP2 by the resistor R4 and the output terminal of the input circuit 4, that is, a point of junction between one end of the resistor R20 and one end of the capacitor C4, is connected directly to the input terminal ch11 of the microcomputer 2. The input circuit 6 has exactly the same configuration as the input circuit 4.

A capacitor C1 is connected between a non-inverting input terminal of the operational amplifier OP1 and the ground potential GND. The capacitor C1 forms a low pass filter in conjunction with resistors R15, R16 and R17 described later.

In particular, the air-fuel-ratio detecting apparatus implemented by the first embodiment includes 3 resistors, namely, R10, R11 and R12 serving as a voltage divider for generating a first voltage V1 and a second voltage V2 by dividing the potential of the power-supply voltage VCC of 5 V. The resistors R10, R11 and R12 are connected between the power-supply voltage VCC and the ground potential GND of 0 V to form a series circuit. The resistors R10, R11 and R12 have resistance values of 2.21 kΩ, 390Ω and 3.9 kΩ respectively. Thus, the first voltage V1 is generated at a point of junction between the resistors R10 and R11 at a potential of 3.3 V, and the second voltage V2 is generated at a point of junction between the resistors R11 and R12 at a potential of 3.0 V.

In addition, the air-fuel-ratio detecting apparatus also includes an operational amplifier OP5, an NPN transistor Tr1 and a PNP transistor Tr2. A non-inverting input terminal of the operational amplifier OP5 is connected to the point of junction between the resistors R10 and R11. An output terminal and an inverting input terminal of the operational amplifier OP5 are connected to each other. Thus, the operational amplifier OP5 serves as a constant-voltage circuit generating the first voltage V1 of 3.3 V mentioned above. The output terminal of the operational amplifier OP5 is connected to the non-inverting input terminal of the operational amplifier OP1 by a resistor R15.

An emitter of the transistor Tr1 is connected to the ground potential GND which is lower than the first voltage V1

(GND<V1). A base of the transistor Tr1 is connected to the output terminal PB21 of the microcomputer 2. A collector of the transistor Tr1 is connected to one end of a resistor R16. The other end of the resistor R16 is connected to a signal line from the resistor R15 to the non-inverting terminal of the operational amplifier OP1. Thus, the resistors R15 and R16 serve as a voltage divider to divide a difference in electric potential between the first voltage V1 of 3.3 V and the ground potential GND of 0 V and to supply a voltage level Vo of the divided electric potential to the non-inverting input terminal of the operational amplifier OP1.

On the other hand, an emitter of the transistor Tr2 is connected to the power-supply voltage VCC which is higher than the first voltage V1 (VCC>V1). A base of the transistor Tr2 is connected to the output terminal PB20 of the microcomputer 2. A collector of the transistor Tr1 is connected to one end of a resistor R17. The other end of the resistor R17 is connected to the signal line from the resistor R15 to the non-inverting terminal of the operational amplifier OP1.

Thus, the resistors R15 and R17 serve as a voltage divider to divide a difference in electric potential between the power supply voltage VCC of 5 V and the first voltage V1 of 3.3 V and to supply the voltage level Vo of the divided electric potential to the non-inverting input terminal of the operational amplifier OP1.

The air-fuel-ratio detecting apparatus 1 also includes an operational amplifier OP4. A non-inverting input terminal of the operational amplifier OP4 is connected to the point of junction between the resistors R11 and R12. An output terminal of the operational amplifier OP4 is connected to a minus-side terminal AF− of the air-fuel-ratio sensor AFS by a resistor R13. The minus-side terminal AF− is a terminal connected to the exhausted-gas-side electrode layer 26 shown in FIG. 2. An inverting input terminal of the operational amplifier OP4 is also connected to the minus-side terminal AF− of the air-fuel-ratio sensor AFS by a resistor R14.

In addition, the air-fuel-ratio detecting apparatus 1 also includes capacitors C2, C3 and C5 as well as diodes D2 and D3. The capacitor C2 for eliminating noise is connected between the non-inverting input terminal of the operational amplifier OP4 and the ground potential GND. By the same token, the capacitor C3 for eliminating noise is connected between the non-inverting input terminal of the operational amplifier OP5 and the ground potential GND.

The capacitor C5 is connected between a signal line from the resistor R13 to the minus-side terminal AF− of the air-fuel-ratio sensor AFS and the ground potential GND. An anode of the diode D2 is connected to a signal line from the shunt resistor R3 to the plus-side terminal AF+ of the air-fuel-ratio sensor AFS. A cathode of the diode D2 is connected to a battery voltage VB (normally 12 V). On the other hand, a cathode of the diode D3 is connected to the signal line from the shunt resistor R3 to the plus-side terminal AF+ of the air-fuel-ratio sensor AFS. An anode of the diode D3 is connected to the ground potential GND. The capacitor C5 is used for preventing a high-voltage surge or high-voltage static electricity from being introduced from the signal line between the air-fuel-ratio detecting apparatus 1 and the minus-side terminal AF− of the air-fuel-ratio sensor AFS into the air-fuel-ratio detecting apparatus 1. By the same token, the two diodes D2 and D3 are used for preventing a high-voltage surge or high-voltage static electricity from being introduced from the signal line between the air-fuel-ratio detecting apparatus 1 and the plus-side terminal AF+ of the air-fuel-ratio sensor AFS into the air-fuel-ratio detecting apparatus 1.

In the air-fuel-ratio detecting apparatus 1 with a configuration described above, the operational amplifier OP1, the resistor R2 and the shunt resistor R3 form an output circuit. As described above, the aforementioned voltage level Vo is supplied to the non-inverting input terminal of the operational amplifier OP1 which serves as an input terminal of this output circuit. This output circuit outputs the voltage Vo to the plus-side terminal AF+ of the air-fuel-ratio sensor AFS.

When both the transistors Tr1 and Tr2 are put in a turned-off state, the operational amplifier OP5 outputs the first voltage V1 of 3.3 V to the non-inverting input terminal of the operational amplifier OP1 as the voltage Vo. As a result, the first voltage V1 is applied to the plus-side terminal AF+ of the air-fuel-ratio sensor AFS.

When only the transistor Tr1 is put in a turned-on state while the transistor Tr2 is turned off, the resistors R15 and R16 work as a voltage divider to divide a difference in electric potential (V1−GND) between the first voltage V1 of 3.3 V and the ground potential GND of 0 V and to supply the voltage level (=V1−$\Delta$Va) of the divided electric potential to the non-inverting input terminal of the operational amplifier OP1. As a result, a divided voltage (=V1−$\Delta$Va) lower than the first voltage V1 by a difference of $\Delta$va is applied to the plus-side terminal AF+ of the air-fuel-ratio sensor AFS.

When only the transistor Tr2 is put in a turned-on state while the transistor Tr1 is turned off, on the other hand, the resistors R17 and R15 work as a voltage divider to divide a difference in electric potential (VCC−V1) between the power-supply voltage VCC of 5 V and the first voltage V1 of 3.3 V and to supply the voltage level (=V1+$\Delta$Vb) of the divided electric potential to the non-inverting input terminal of the operational amplifier OP1. As a result, a divided voltage (=V1+$\Delta$Vb) higher than the first voltage V1 by a difference of $\Delta$Vb is applied to the plus-side terminal AF+ of the air-fuel-ratio sensor AFS.

In this embodiment, the resistance values of the resistors R15, R16 and R17 are set at 200$\Omega$, 3.09 k$\Omega$ and 1.5 k$\Omega$ respectively. Thus, the voltage level (V1−$\Delta$Va) is 3.1 V whereas the voltage level (V1+$\Delta$Vb) is 3.5 V. Each of the differences $\Delta$Va and $\Delta$Vb is 0.2 V.

Connected to the output circuit comprising the operational amplifier OP4 and the resistors R13 and R14, the second voltage V2 of 3.0 V, which is to be input to the non-inverting input terminal of the operational amplifier OP4, is always applied to the minus-side terminal AF− of the air-fuel-ratio sensor AFS.

As a result, during a normal state in which the two transistors Tr1 and Tr2 are both put in a turned-off state, a difference in electric potential (V1−V2=0.3 V) between the first and second voltages V1 and V2 generated by the resistors R10, R11 and R12 are applied to both ends of the air-fuel-ratio sensor AFS as a voltage for detecting the air-fuel ratio (the concentration of oxygen in the exhaust gas) of mixture (a voltage for detecting the concentration of oxygen). The voltage applied to the air-fuel-ratio sensor AFS causes a current I, corresponding to the present concentration of oxygen contained in exhaust gas, to flow through the sensor AFS.

Also referred to hereafter as a sensor current, the current I flowing through the air-fuel-ratio sensor AFS also flows through the shunt resistor R3. Thus, an electric-potential difference proportional to the sensor current I appears between the ends of the shunt resistor R3. This electric-potential difference is supplied to the microcomputer 2 as follows. The voltage Vo appearing at the end of the shunt resistor R3 connected to the plus-side terminal AF+ of the air-fuel-ratio sensor AFS, that is, the voltage applied to the plus-side terminal AF+ of the air-fuel-ratio sensor AFS, is supplied to the input terminal ch11 of the microcomputer 2 through the operational amplifier OP2 and the input circuit 4. On the other hand, a voltage Vi having the same potential level as a voltage appearing at the other end of the shunt resistor R3, that is, a voltage output by the operational amplifier OP1, is supplied to the input terminal ch12 of the microcomputer 2 through the operational amplifier OP3 and the input circuit 6.

Figure 4:
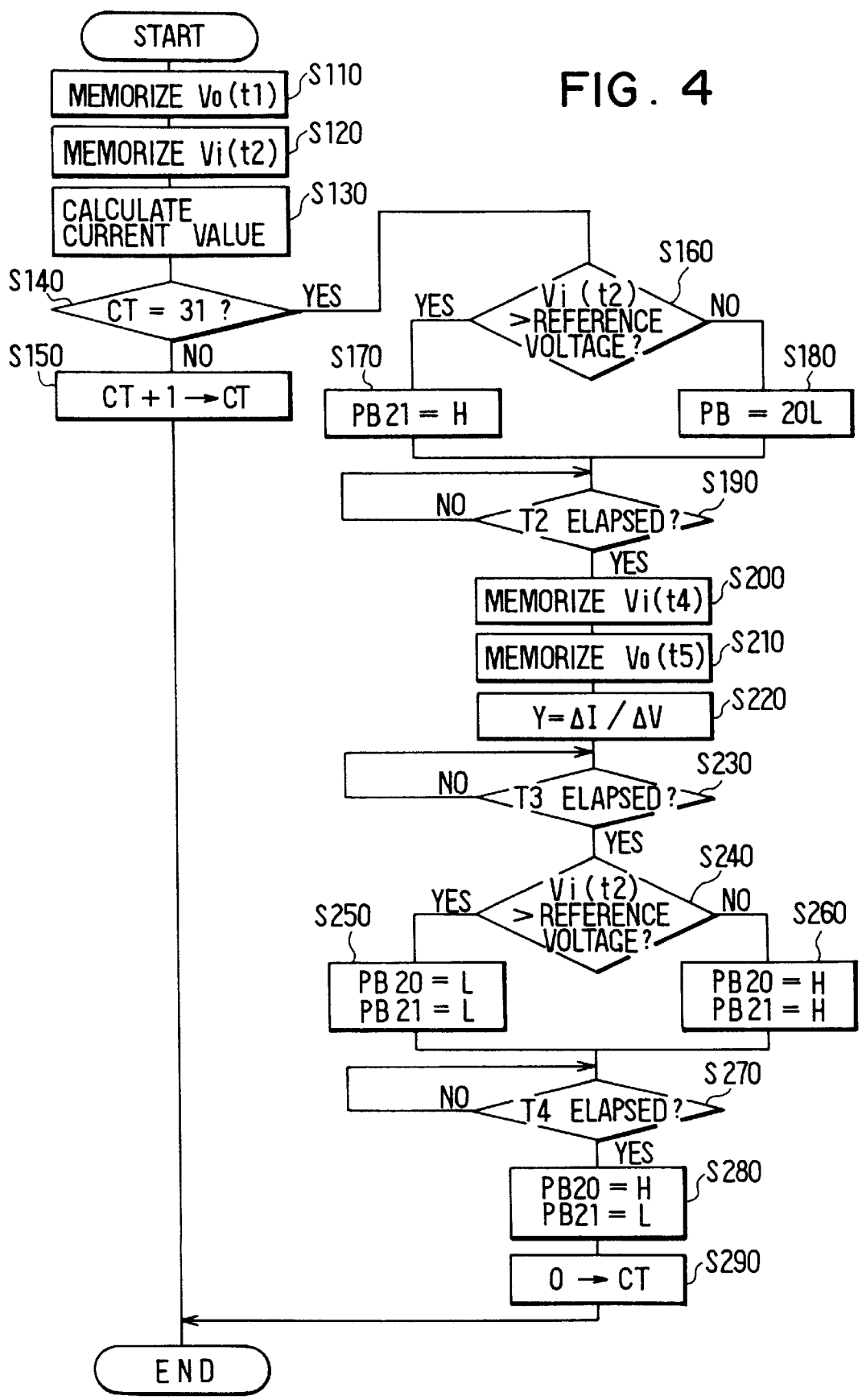
FIG. 4 is a flowchart showing a detection routine carried out by a microcomputer installed in the air-fuel-ratio detecting apparatus according to the first embodiment of the present invention.

The microcomputer 2 of the air-fuel-ratio detecting apparatus 1 according to this embodiment periodically carries out detection routine shown in FIG. 4 to determine the air fuel ratio of the mixture (oxygen concentration of the exhaust gas) by detecting the sensor current I of the AFS, and to detect the element admittance Y of the air-fuel-ratio sensor AFS.

The detection routine, which is carried out by the microcomputer 2 of the air-fuel-ratio detecting apparatus 1, will now be described by referring to a flowchart shown in FIG. 4. The detection routine shown in FIG. 4 is carried out at time intervals of 4 ms. In addition, the microcomputer 2 initially sets signals output through the output terminals PB20 and PB21 at levels that put both the transistors Tr1 and Tr2 in a turned-off state. To be more specific, the initial output levels of the terminals PB20 and PB21 are set at a high level of 5 V and a low level of 0 V respectively.

As shown in FIG. 4, the flowchart begins with step S110 at which the microcomputer 2 starts execution of the detection routine to detect the voltage Vo supplied to the input terminal ch11 and stores the detected voltage Vo as Vo(t1). Then, it proceeds to step S120 at which the microcomputer 2 detects the voltage Vi to be supplied to the input terminal ch12 and stores the detected voltage Vi as Vi(t2).

Then, the flow of the detection processing goes on to step S130 at which the microcomputer 2 calculates the current value (the limiting current value) of the sensor current I by dividing (Vi(t2)−Vo(t1)) by the resistance RS of the shunt resistor R3. (Vi(t2)−Vo(t1)) is a difference between the voltage Vi(t2) detected at the step S120 and the voltage Vo(t1) detected at the step S110. Furthermore, an air-fuel ratio of the air-fuel mixture (that is, the oxygen concentration in the exhaust gas) is calculated from the limiting current value and a characteristic map stored in advance in a ROM of the microcomputer 2.

Subsequently, the flow of the detection processing goes on to step S140 at which the microcomputer 2 determines whether the value of a counter CT is equal to "31" corresponding to a predetermined period T1 (=128 ms). The value of the counter CT is stored in a RAM on the microcomputer 2. When the value of the counter CT is not equal to "31" in step S140, the flow of the detection processing proceeds to step S150 at which the microcomputer 2 increase the value of the counter CT by 1, and then ends the detection processing.

On the other hand, when the value of the counter CT is determined in step S140 that it is equal to "31", it is considered that it is time to detect the element admittance Y, and the flow proceeds to step 160. In step S160, the microcomputer 2 determines whether the voltage Vi(t2) detected in step S120 is greater than predetermined reference voltage. The reference voltage is set at the level of an output voltage Vi which is outputted from the operational amplifier OP1 when a predetermined current (for example, a center value) for the AFS, within the dynamic range shown in FIG. 3, flows through the shunt resistor R3. The dynamic range is a range in which a current is detectable.

When the voltage Vi(t2) is determined at the step S160 to be higher than the reference voltage, that is, if the present sensor current I is greater than the predetermined current in the dynamic range, the flow of the detection processing proceeds to step S170. In step S170, the microcomputer 2 changes the output level of the output terminal PB21 from low level to high level as shown at time t3 in FIG. 5A to turn on the transistor Tr1. Then, the flow of the detection processing proceeds to step S190. Accordingly, as shown at time t3 in FIG. 5A, the voltage Vo applied to the plus-side terminal AF+ of the air-fuel-ratio sensor AFS changes to a voltage of 3.1 V which is lower than the first voltage V1 of 3.3 V by the difference ΔVa of 0.2 V described above. Accordingly, the sensor current I and the voltage Vi, which is an input voltage to the input terminal ch12, that is, an output voltage outputted from the operational amplifier OP1, also change to the negative side.

When the voltage Vi(t2) is determined in step S160 to be not higher than the reference voltage, that is, when the present sensor current I is not greater than the predetermined current in the dynamic range, the flow of the detection processing proceeds to step S180. Instep S180, the microcomputer 2 changes the output level of the output terminal PB20 from high level to low level as shown at time t3 in FIG. 5B to turn on the transistor Tr2. Then, the flow of the detection processing proceeds to step S190. Accordingly, as shown at time t3 in FIG. 5B, the voltage Vo applied to the plus-side terminal AF+ of the AFS changes to a voltage of 3.5 V which is higher than the first voltage V1 by the difference ΔVb of 0.2 V described above. Accordingly, the sensor current I and the voltage Vi, which is an input voltage to the input terminal ch12, also change to the positive side.

In step S190, the microcomputer 2 determines whether a period T2 (=135 microseconds) has elapsed after completion of the processing of step S170 or S180. The period T2 is predetermined such that the change amount ΔI in sensor current I is expected to reach the peak at the end of the period T2. The microcomputer 2 repeats the processing of the step S190 until the period T2 elapses. When the microcomputer 2 determines that the period T2 has elapsed, the flow of the detection processing then goes on to step S200 to detect the voltage Vi supplied to the input terminal ch12, and to store the detected voltage Vi as Vi(t4) mentioned above. Then, the flow of the detection processing then goes on to step S210 to detect the voltage Vo supplied to the input terminal ch11 and to store the detected voltage Vo as Vo(t5).

Then, the flow of the detection processing then goes on to step S220 to calculate the admittance Y (the reciprocal of the element resistance of the sensor element) according to equation (1) as follows:

$$Y = \frac{\Delta I}{\Delta V} \qquad (1)$$
$$= \frac{\{Vi(t2) - Vo(t1)\} - \{Vi(t4) - Vo(t5)\}}{\{Vo(t1) - Vo(t5) \times Rs\}}$$

It should be noted that the element admittance Y calculated in step S220 is used for at least controlling the heater 23 installed in the air-fuel-ratio sensor AFS. More specifically, necessary current supply amount to the heater 23 is calculated to equalize a difference between the element admittance Y calculated in step S220 and a target element admittance required for sufficiently activating the air-fuel-ratio sensor AFS. Further, the current supply to the heater 23 is duty-controlled according to the calculated current supply amount via a heater driving circuit (not shown).

Then, the flow of the detection processing proceeds to step S230 at which the microcomputer 2 determines whether a period of time T3 (=200 microseconds) has elapsed after completion of the processing of the step S170 or S180. The microcomputer 2 repeats the processing of the step S230 until the period T3 elapses. When the microcomputer 2 determines that the period T3 has elapsed, the flow of the detection processing goes on to step S240 to determine whether the voltage Vi(t2) detected in step S120 is greater than the reference voltage.

If the voltage Vi(t2) is determined in the step S240 to be greater than the reference voltage, the flow of the detection processing proceeds to step S250. Instep S250, the output level of the output terminal PB21 is returned from high level to low level to turn off the transistor Tr1, and the output level of the output terminal PB20 is changed from high level to low level to turn on the transistor Tr2, as shown at time t6 in FIG. 5A. Then, the flow of the detection processing proceeds to step S270. Accordingly, as shown at time t6 in FIG. 5A, the voltage Vo applied to the plus-side terminal AF+ of the air-fuel-ratio sensor AFS changes to a voltage of 3.5 V which is higher than the first voltage V1 by the difference ΔVb of 0.2 V described above. Accordingly, the sensor current I and the voltage Vi, which is an input voltage to the input terminal ch12, also change to the positive side.

If the voltage Vi(t2) is determined in step S240 to be not greater than the reference voltage, the flow of the detection processing proceeds to step S260. In step S260, the output level of the output terminal PB20 is returned from low level to high level to turn off the transistor Tr2, and the output level of the output terminal PB21 is changed from low level to high level to turn on the transistor Tr1, as shown at time t6 in FIG. 5B. Then, the flow of the detection processing proceeds to step S270. Accordingly, as shown at time t6 in FIG. 5B, the voltage Vo applied to the plus-side terminal AF+ of the air-fuel-ratio sensor AFS changes to a voltage of 3.1 V which is lower than the first voltage V1 by the difference ΔVa of 0.2 V described above. Accordingly, the sensor current I and the voltage Vi, which is an input voltage to the input terminal ch12, also change to the negative side.

In step S270, the microcomputer 2 determines whether a period of time T4 (=200 microseconds) has elapsed after completion of the processing of the step S250 or S260. The microcomputer 2 repeats the step S270 until the period of time T4 elapses. When the microcomputer 2 determines that the period of time T4 has elapsed, the flow of the detection processing goes on to step S280. In step S280, the output level of the output terminal PB21 is returned to the low level of the initial state to turn off the transistor Tr1, and the output level of the output terminal PB20 is returned to the high level of the initial stage to turn off the transistor Tr2, as shown at time T7 in FIGS. 5A and 5B. Accordingly, as shown at time t7 in FIGS. 5A and 5B, the voltage Vo applied to the plus-side terminal AF+ of the sensor AFS is returned to the first voltage V1, and the sensor current I and the voltage Vi, which is an input voltage to the input terminal ch12, are also returned to the initial state.

Finally, the flow of the detection processing goes on to step S290 to reset the value of the counter CT at "0", and ends the detection processing.

Figure 5A:
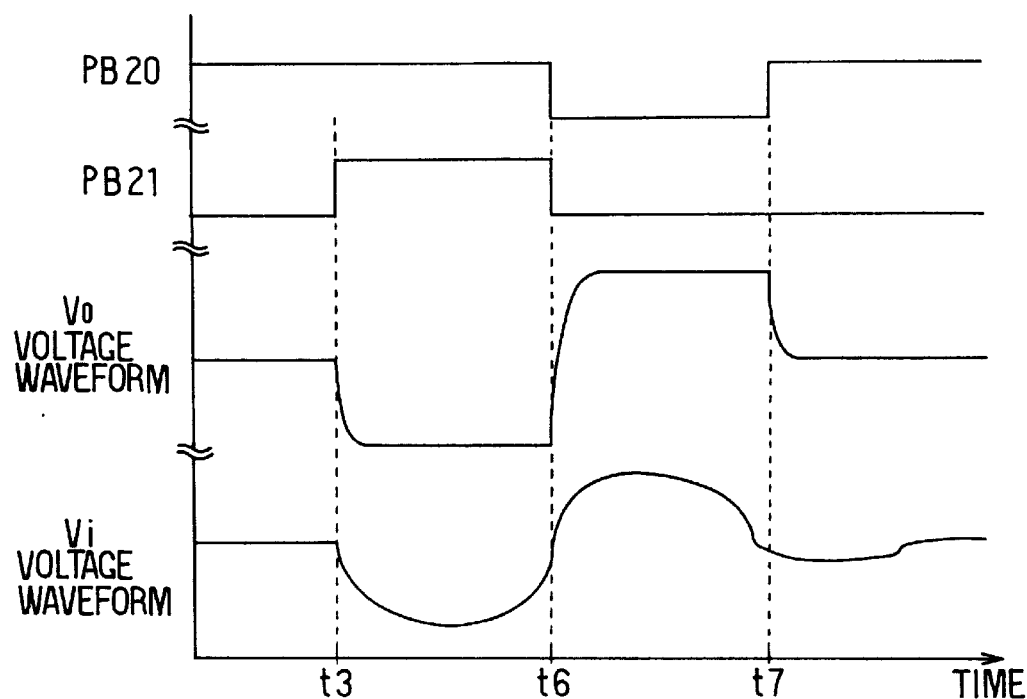
FIGS. 5A and 5B are time charts showing operations of the detection processing in FIG. 4 according to the first embodiment of the present invention.
Figure 5B:
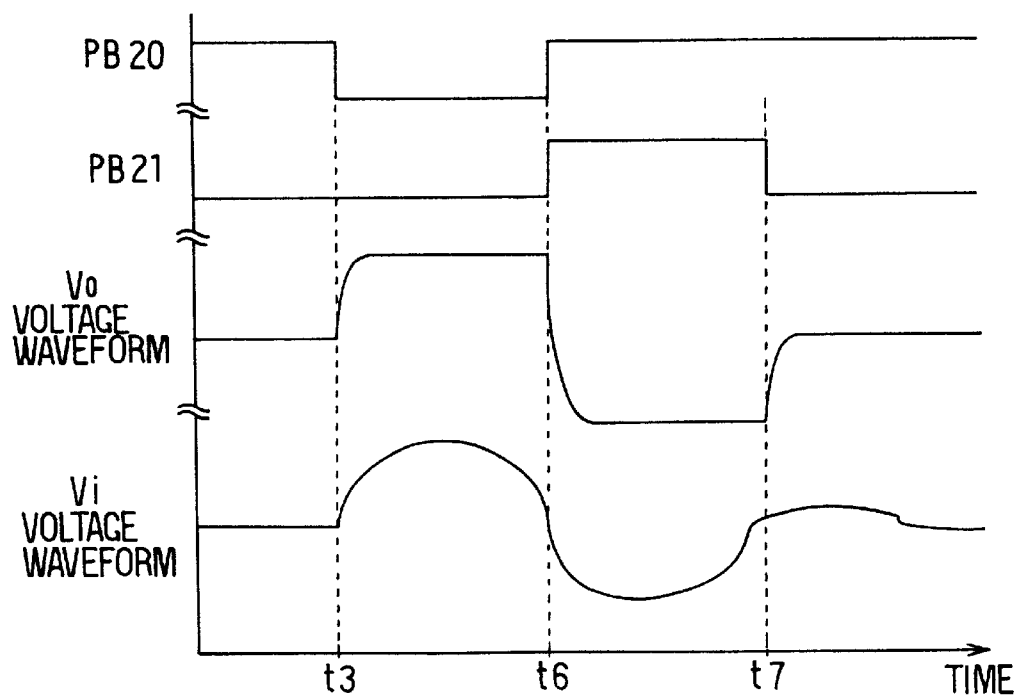

According to the detection processing shown in FIG. 4, in short, the predetermined period T1 (=128 ms), which is a cyclic period for detecting the element admittance Y, is counted by steps of S140, S150 and S290. When it is determined that the predetermined period T1 has elapsed ("YES" in step S140), the transistors Tr1 and Tr2 are turned on/off by the processing in steps S160 to S180 and S230 to S280 as an applied-voltage changing means to change the voltage Vo to a level higher than the first voltage V1 and to a level lower than the first voltage V1 as shown in FIG. 5A or 5B.

Furthermore, the processing of the steps S110 and S120, as a first current detecting means, is carried out to detect the sensor current I as a difference between the voltages Vi(t2) and Vo(t1) appearing at respective ends of the shunt resistor R3 before the voltage Vo applied to the plus-side terminal AF+ is changed in step S170 or S180. The processing of the steps S190 to S210, as a second current detecting means, is carried out to detect the sensor current I as a difference between the voltages Vi(t4) and Vo(t5) appearing at respective ends of the shunt resistor R3 when it is determine that the predetermined time T2 (=135 microseconds) has elapsed ("YES" in step S190) after the voltage Vo applied to the plus-side terminal AF+ is changed in step S170 or S180.

And furthermore, the processing in step S220, as an admittance calculating means (element-resistance-component calculating means), is carried out to calculate the element admittance Y of the air-fuel-ratio sensor AFS from a difference in sensor current I calculated from the voltages Vo(t1), Vi(t2), Vi(t4) and Vo(t5) detected in steps S110, S120, S200 and S210. More specifically, such difference in the sensor current I is a difference between the sensor current I represented by [{Vi(t2)–Vo(t1)}/RS] prior to the change in voltage Vo and the sensor current I represented by [{Vi(t4)–Vo(t5)}/RS] when the predetermined period T2 has elapsed after the change in voltage Vo.

The processing in the step S130 as an oxygen concentration calculating means calculates the limiting current of the air-fuel-ratio sensor AFS from Vi(t2) and Vo(t1) detected at the steps S120 and S110. The air-fuel ratio of the air-fuel mixture (the oxygen concentration of exhaust gas) is determined based on the limiting current.

It should be noted that, in the first embodiment shown in FIG. 1, a circuit, comprising the resistors R10 to R12, the resistors R15 to R17, the resistor R2, the shunt resistor R3, the operational amplifiers OP1 and OP5 and the transistors Tr1 and Tr2, corresponds to first voltage applying means. On the other hand, a circuit, comprising the operational amplifier OP4 and the resistors R13 and R14, corresponds to second voltage applying means. A circuit, including the circuit corresponding to the first voltage applying means and the circuit corresponding to the second voltage applying means, corresponds to voltage applying means of the present invention. Each one of a circuit comprising the transistor Tr1 and the resistor R16 and a circuit comprising the transistor Tr2 and the resistor R17 corresponds to voltage switching circuit of the present invention.

According to the air-fuel-ratio detecting apparatus 1 of the first embodiment of the present invention, by putting the transistors Tr1 and Tr2 in a turned-on or turned-off state, the voltage applied to the plus-side terminal AF+ of the air-fuel-ratio sensor AFS is changed immediately. Thus, the sensor current I, when the predetermined period of time T2 has elapsed after the change in voltage applied to the terminal, is detected reliably. As a result, by virtue of the air-fuel-ratio detecting apparatus 1, the element admittance or the element impedance, which is a resistance component of the sensor element, is detected accurately by changing the voltage applied to the air-fuel-ratio sensor AFS without a delay in spite of the simple configuration of the sensor AFS. Accordingly, it is possible to accurately execute feedback control of the heater 23 for maintaining the activated state of the air-fuel-ratio sensor AFS, and to evaluate the deterioration degree of the sensor AFS.

According to the air-fuel-ratio detecting apparatus 1 of the first embodiment of the present invention, the voltage applied to the sensor AFS is changed to positive and negative sides by turning on/off the transistors Tr1 and Tr2.

Accordingly, when the applied voltage is returned to its initial level, electric charges are discharged from capacitance components of the sensor AFS in a short period of time. The capacitance components include a particle-boundary capacitance on a particle boundary surface of the solid electrolyte layer 24, and an electrode boundary-surface capacitance. As a result, the sensor current after detecting the element admittance of the sensor AFS is stabilized quickly.

Furthermore, in the air-fuel-ratio detecting apparatus 1 of the first embodiment of the present invention, the emitter of the transistor Tr2 is connected to the power-supply voltage Vcc which is set at a higher level than the first voltage V1 outputted by the operational amplifier OP5 while the emitter of the transistor Tr1 is connected to the ground potential GND which is lower than the first voltage V1. The voltage applied to the plus-side terminal AF+ of the sensor AFS is changed to the positive side higher than the first voltage V1 by turning eon the transistor Tr2. The voltage applied to the plus-side terminal AF+ of the sensor AFS is changed to the negative side lower than the first voltage V1 by turning on the transistor Tr1.

Accordingly, the voltage applied to the sensor AFS is changed to positive and negative sides by turning on the transistors Tr1 and Tr2 sequentially as shown in FIGS. 5A and 5B. Therefore, both of the transistors Tr1 and Tr2 can be turned off while the element impedance detection is not carried out, and an increase in the electric-power consumption is prevented.

In order to show the advantage of the first embodiment, a comparative configuration of the air-fuel-ratio detecting apparatus will now be explained as follows. In the comparative configuration, NPN transistor, which is used for the transistor Tr1, is used for the transistor Tr2. In this case, the emitter of the transistor Tr2 is connected to the ground potential GND as is the case with the transistor Tr1. In such a configuration, the voltage applied to the plus-side terminal AF+ of the air-fuel sensor AFS can be changed in three ways as follows:

(a) When both of the transistors Tr1 and Tr2 are turned off, the first voltage Vi is output to the plus-side terminal AF+ of the air-fuel sensor AFS from the operational amplifier OP5.
(b) When one of the transistors Tr1 and Tr2 is turned on (for example, when Tr1 is turned on), a voltage, that is obtained by dividing the first voltage Vi by the resistors R15 and R16, is output to the plus-side terminal AF+ of the air-fuel sensor AFS. If it is the transistor Tr1 that is put in a turned-on state, for example, a voltage divider comprising the resistors R15 and R16 divides the difference between the first voltage V1 and the ground potential GND, applying the divided voltage to the plus-side terminal AF+ of the air-fuel sensor AFS.
(c) When both of the transistors Tr1 and Tr2 are turned on, a voltage, that is obtained by dividing the first voltage V1 by the resistors R15 and the summation of the resistors R16 and R17, is output to the plus-side terminal AF+ of the air-fuel sensor AFS.

In a normal operation, the air-fuel-ratio detecting apparatus 1 is driven as in the above (b), and the voltage applied to the sensor AFS is changed to positive and negative sides by turning on/off the transistors Tr1 and Tr2 in the order of (b)→(a)→(c), or (b)→(c)→(a) to change the voltage applied to the plus-side terminal AF+ of the air-fuel sensor AFS from the normal voltage. It should be noted that the same theory is applied to another comparative configuration in which a PNP transistor is used as the transistor Tr1 as is the case with the transistor Tr2. In this case, the emitter of the transistor Tr1 is connected to the power-supply voltage Vcc as is the case with the transistor Tr2.

According to the above-described comparative configurations, however, one of the transistors Tr1 and Tr2 should be kept in the turned-on state while the element admittance is not detected. Therefore, they cause an increase in electric-power consumption.

According to the air-fuel-ratio detecting apparatus 1 of the first embodiment of the present invention, on the contrary, it is possible to reduce the electric-power consumption.

In addition, according to the air-fuel-ratio detecting apparatus 1 of the first embodiment of the present invention, the 3 resistors R10, R11 and R12 connected in series between the power-supply voltage Vcc and the ground potential GND are employed as a source for generating the first voltage V1 of 3.3 V applied to the plus-side terminal AF+ of the air-fuel sensor AFS and a source for generating the second voltage V2 of 3.0 V applied to the minus-side terminal AF– of the air-fuel sensor AFS.

As a result, a predetermined oxygen-concentration-detection voltage of 0.3 V is stably applied to the air-fuel-ratio sensor AFS. Therefore, the air-fuel ratio is detected accurately even if the ambient temperature of the air-fuel-ratio detecting apparatus 1 changes. This is because the resistance values of the resistors R10–R12 change in the same way as the ambient temperature changes. As a result, the ratios of resistance values among the resistors R10–R12 do not change substantially, and thereby keeping the first and second voltages V1 and V2 substantially constant.

Furthermore, in the air-fuel-ratio detecting apparatus 1 implemented by the first embodiment, when the voltage Vi(t2) is determined to be greater than the predetermined value in the dynamic range, that is, if the result of the determination of the step S160 is YES, the voltage applied to the air-fuel sensor AFS is changed to the negative side, that is, the applied voltage is decreased (step S170), and the element admittance is calculated from the current change accompanied by the change of the applied voltage.

On the other hand, when the voltage Vi(t2) is determined to be less than the predetermined value in the dynamic range, that is, if the result of the determination of the step S160 is NO, the voltage applied to the air-fuel sensor AFS is changed to the positive side, that is, the applied voltage is increased (step S180), and the element admittance is calculated from the current change accompanied by the change of the applied voltage.

Thus, in the detection of an element admittance Y, it is possible to prevent the voltage applied to the sensor AFS at the admittance detection from being out of the dynamic range securely. Accordingly, the sensor current is detected within the dynamic range, and the element admittance is detected accurately.

(Second Embodiment)

In the air-fuel-ratio detecting apparatus 1 of the first embodiment of the present invention, only one air-fuel-ratio sensor AFS is used. It should be noted that, however, in the case of an ordinary engine such as a V-type 6-cylinder engine or a V-type 8-cylinder engine, an air-fuel-ratio sensor AFS is provided on each exhaust pipe. Thus, in the case of an engine provided with a couple of air-fuel-ratio sensors AFS, a pair of air-fuel-ratio detecting apparatuses 1 shown in FIG. 1 except the microcomputer 2 are required.

With such a dual-sensor configuration, however, the size of the circuit becomes almost twice the size of that of the air-fuel-ratio detecting apparatuses 1 shown in FIG. 1.

Figure 6:
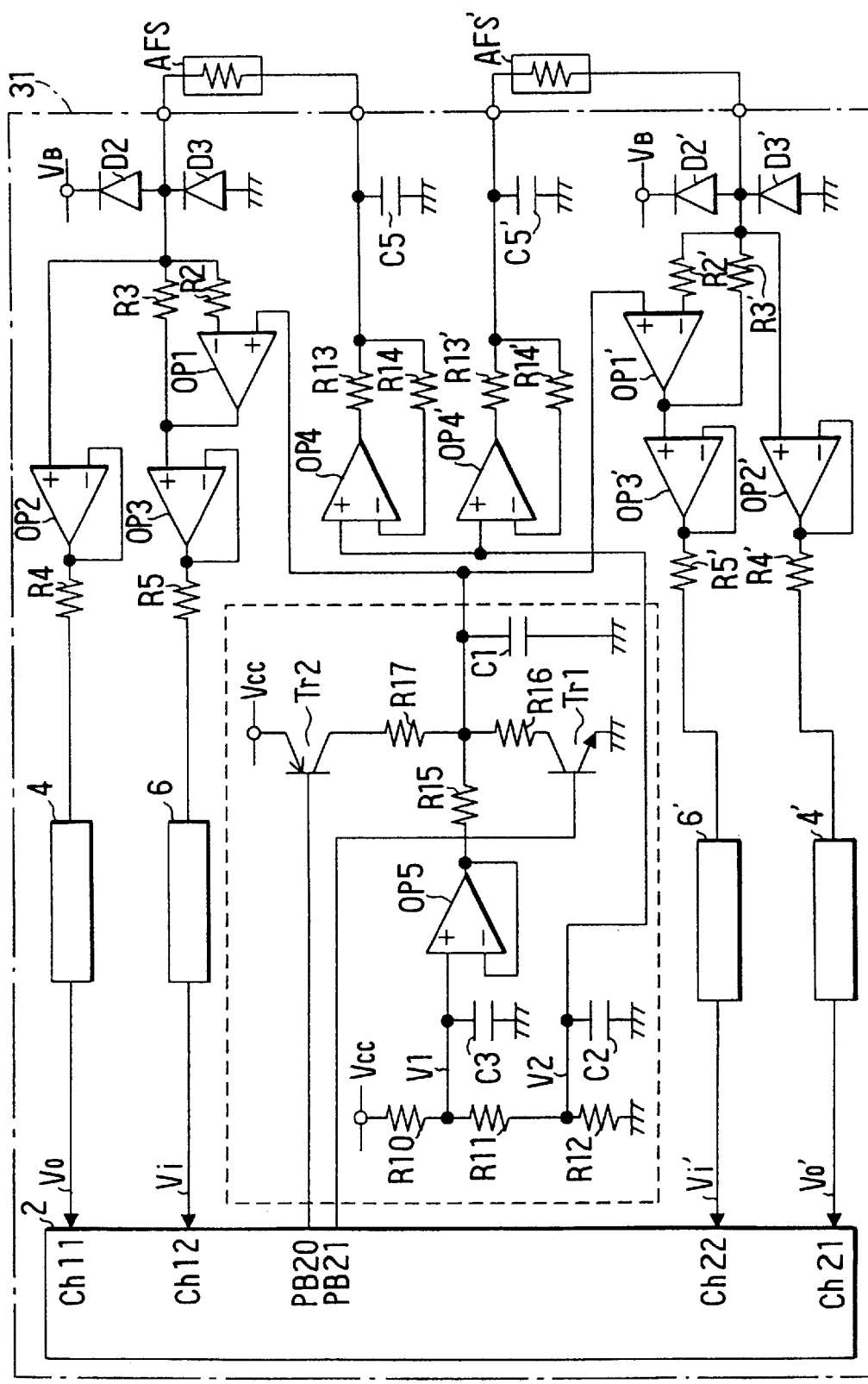
FIG. 6 is a circuit diagram showing an air-fuel-ratio detecting apparatus according to a second embodiment of the present invention.

In order to reduce in size, there is provided a second embodiment implementing an air-fuel-ratio detecting apparatus connected to 2 air-fuel-ratio sensors AFS in a preferred typical configuration shown in FIG. 6.

FIG. 6 is a circuit diagram showing a typical configuration of an air-fuel-ratio detecting apparatus 31 implemented by the second embodiment. Members and voltage signals of the air-fuel-ratio detecting apparatus 31 shown in FIG. 6 identical with those of the air-fuel-ratio detecting apparatus 1 shown in FIG. 1 are assigned the same reference numerals and notations as the latter. To put it in detail, newly added members and voltage signals of the air-fuel-ratio detecting apparatus 31 shown in FIG. 6 performing similar functions to those of the air-fuel-ratio detecting apparatus 1 shown in FIG. 1 are assigned the same reference numerals and notations as the latter except an apostrophe "'" is appended to each reference numeral and notation denoting a new member and a new voltage signal. Detailed description of such new members and voltage signals is not repeated.

As a matter of fact, components employed in the second and subsequent embodiments substantially identical with those of the first embodiment are denoted by the same reference numerals and notations as the latter.

In this and the following embodiments, components which are substantially the same as those in previous embodiments are assigned the same reference numerals.

As shown in FIG. 6, the air-fuel-ratio detecting apparatus 31 implemented by the second embodiment comprises component pairs each comprising a component for a first air-fuel-ratio sensor AFS and an identical component for a second air-fuel-ratio sensor AFS' except the microcomputer 2 shown in FIG. 1 and a block enclosed by a dashed line in FIG. 6. The microcomputer 2 and the block enclosed by the dashed line are components common to both the air-fuel-ratio sensors AFS and AFS'. Much like the input terminals ch11 and ch12 of the microcomputer 2 of the first embodiment shown in FIG. 1, the input terminals ch21 and ch22 of the microcomputer 2 employed in the second embodiment shown in FIG. 6 are input terminals of an A/D converter embedded in the microcomputer 2.

As a result, according to the air-fuel-ratio detecting apparatus 31 according to the second embodiment of the present invention, the size of the circuit configuration and the cost of the apparatus 31 can be reduced.

(Third Embodiment)

Figure 7:
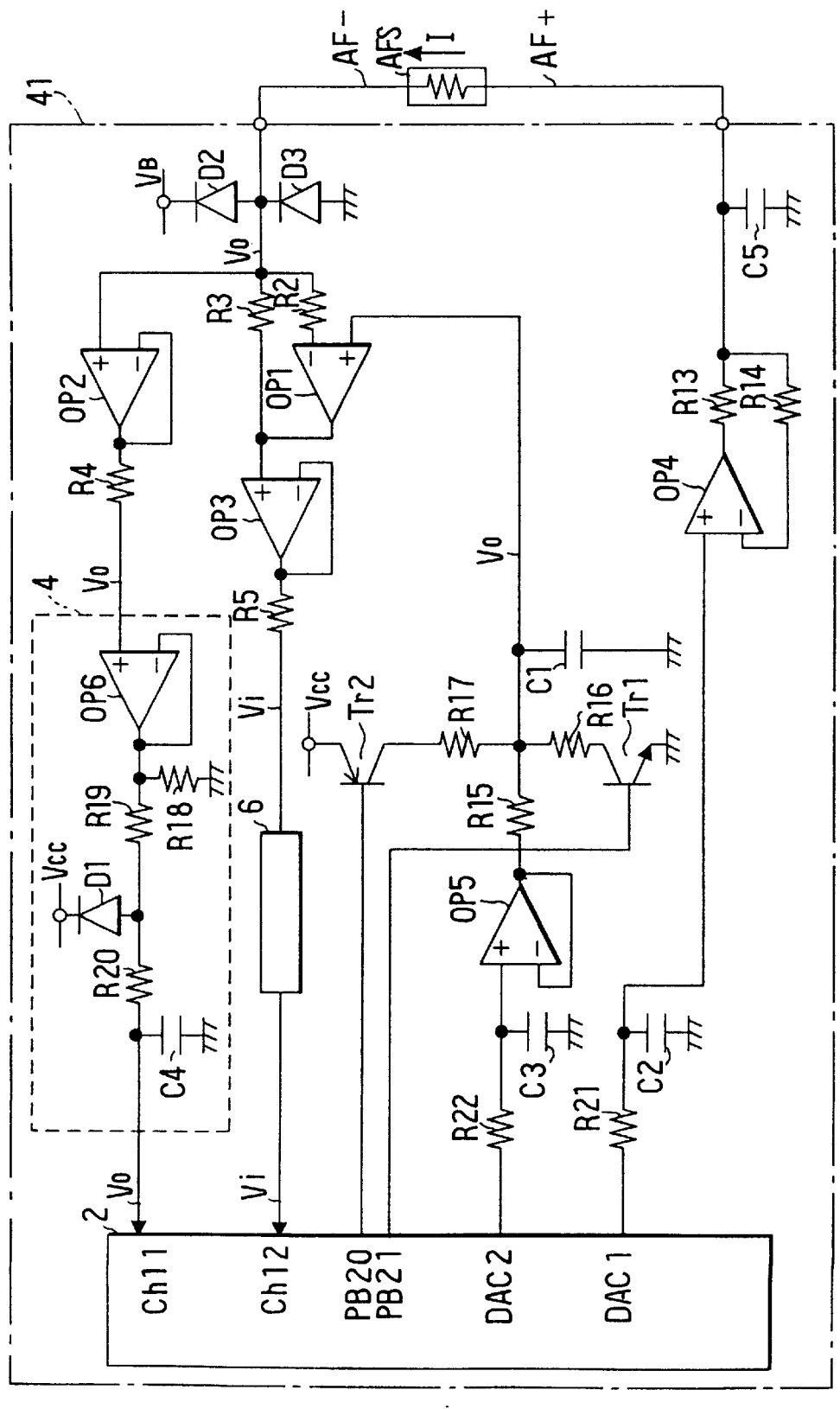
FIG. 7 is a circuit diagram showing an air-fuel-ratio detecting apparatus according to a third embodiment of the present invention.
Figure 8:
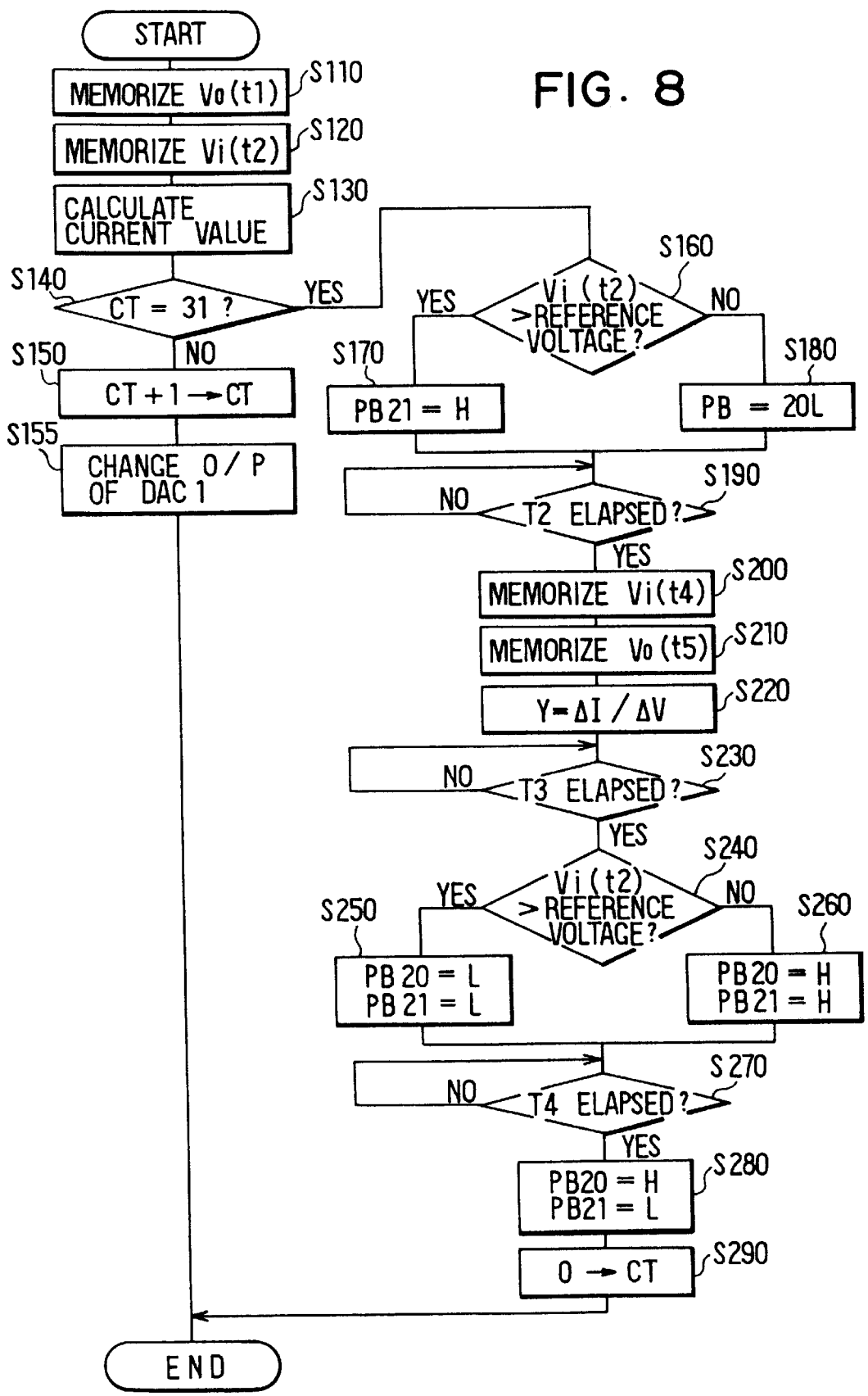
FIG. 8 shows a flowchart showing a detection routine carried out by a microcomputer employed in the air-fuel-ratio detecting apparatus according to the third embodiment of the present invention.
Figure 9:
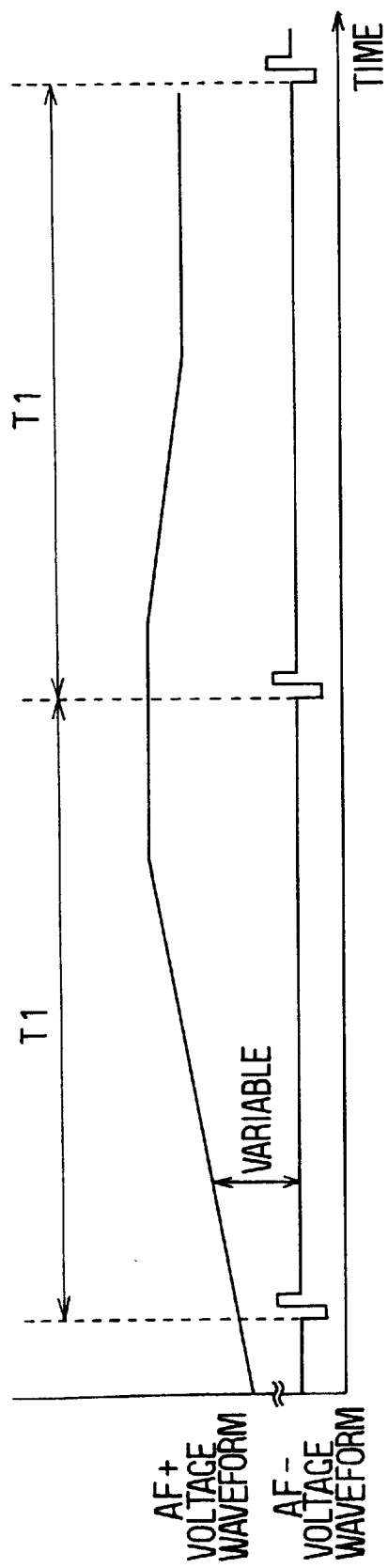
FIG. 9 is a time chart showing operations of the detection processing according to the third embodiment of the present invention.

Next, an air-fuel-ratio detecting apparatus implemented by a third embodiment is explained by referring to FIGS. 7 to 9.

FIG. 7 is a circuit diagram showing the configuration of an air-fuel-ratio detecting apparatus 41 implemented by the third embodiment. It should be noted that components employed in the third embodiment shown in FIG. 7 identical with those of the first embodiment shown in FIG. 1 are denoted by the same reference numerals and notations as the latter.

Four differences, namely, differences 1 to 4, between the air-fuel-ratio detecting apparatus 41 implemented by the third embodiment shown in FIG. 7 and the air-fuel-ratio detecting apparatus 1 implemented by the first embodiment shown in FIG. 1 are listed below. That is, the air-fuel-ratio detecting apparatus 41 implemented by the third embodiment shown in FIG. 7 is implemented as follows:

1: In the first place, the microcomputer 2 employed in the air-fuel-ratio detecting apparatus 41 is provided with not only an A/D converter but also with a simple D/A converter like one shown in FIG. 12. Terminals DAC1 and DAC2 of the microcomputer 2 are output terminals of the simple D/A converter embedded in the microcomputer 2.

2: In the second place, the air-fuel-ratio sensor AFS is connected reversely. To put it in detail, the minus-side terminal AF− of the air-fuel-ratio sensor AFS is connected to a point of junction between the resistor R2 and the shunt resistor R3 whereas the plus-side terminal AF+ is connected to a point of junction between the resistor R13 and the resistor R14.

3: In the third place, the 3 resistors R10, R11 and R12 are eliminated. The non-inverting input terminal of the operational amplifier OP4 is connected to the output terminal DAC1 of the microcomputer 2 by a resistor R21 and the non-inverting input terminal of the operational amplifier OP5 is connected to the output terminal DAC2 of the microcomputer 2 by a resistor R22.

The simple D/A converter embedded in the microcomputer 2 is capable of outputting a constant voltage of typically 3.0 V all the time through the output terminal DAC2 and a variable voltage higher than 3.0 V, for example 3.3 V, through the output terminal DAC1.

In the third embodiment, the constant voltage of 3.0 V output through the output terminal DAC2 and the variable voltage higher than 3.0 V output through the output terminal DAC1 correspond to the first and second voltages and respectively.

4: In the fourth place, the microcomputer 2 carries out detection processing shown in FIG. 8 in place of the detection processing shown in FIG. 4. As shown in FIG. 8, the current-detection processing carried out in the third embodiment is different from the detection processing shown in FIG. 4 only in that processing of step S155 is added to the former.

To put it in detail, in the detection processing carried out in the third embodiment, after the value of the counter CT is incremented by 1 at the step S150, the flow of the processing goes on to step S155 at which an optimum oxygen-concentration-detection voltage to be applied to the air-fuel-ratio sensor AFS is determined from an air-fuel ratio found at the step S130. Then, the magnitude of the voltage output through the output terminal DAC1 is changed in accordance with the voltage determined at the step S155.

To put it in detail, a voltage on a chain line L1 of the voltage-current characteristic of the air-fuel-ratio sensor AFS shown in FIG. 3 for an air-fuel ratio A/F found at the step S130 is taken as an optimum oxygen-concentration-detection voltage to be applied next. The magnitude of the voltage output through the output terminal DAC1 is computed by adding this optimum oxygen-concentration-detection voltage to the constant voltage of 3.0 output through the output terminal DAC2. That is, the voltage output through the output terminal DAC1 is changed to a level equal to the sum of this optimum oxygen-concentration-detection voltage and the constant voltage of 3.0 within a period of time not longer than the maximum processing time delay inherent in the simple D/A converter embedded in the microcomputer 2. It should be noted that the chain line L1 is a line connecting points at about the centers of the limit-current segments parallel to the V axis of the voltage-current characteristic shown in FIG. 3.

After the processing of the step S155, the detection processing is ended.

In a normal operation of the air-fuel-ratio detecting apparatus 41 implemented by the third embodiment as described above wherein both the transistors Tr1 and Tr2 are put in a turned off state, the constant voltage of 3.0 V output through the output terminal DAC2 of the microcomputer 2 is applied to the minus-side terminal AF− of the air-fuel-ratio sensor AFS an the variable voltage higher than 3.0 V output through the output terminal DAC1 of the microcomputer 2 is applied to the plus-side terminal AF+ of the air-fuel-ratio sensor AFS.

Much like the first embodiment, when the microcomputer 2 employed in the air-fuel-ratio detecting apparatus 41 puts the transistor Tr1 and/or the transistor Tr2 in a turned-on state, a voltage divider works, changing the voltage of 3.0 V applied to the minus-side terminal AF− of the air-fuel-ratio sensor AFS. Thus, it is possible to detect a sensor current I that flows after the predetermined period of time T2 has elapsed since the operation to change the voltage of 3.0 V applied to the minus-side terminal AF− of the air-fuel-ratio sensor AFS by means of the voltage divider with a high degree of reliability. As a result, the element admittance Y of the air-fuel-ratio sensor AFS can be detected with a high degree of accuracy.

In particular, according to the air-fuel-ratio detecting apparatus 41 implemented by the third embodiment, the variable voltage applied to the plus-side terminal AF+ of the air-fuel-ratio sensor AFS can be changed by a simple D/A converter as shown in FIG. 9. As a result, the voltage applied to the plus-side terminal AF+ of the air-fuel-ratio sensor AFS, that is, the oxygen-concentration-detection voltage applied between the plus-side terminal AF+ and the minus-side terminal AF− of the air-fuel-ratio sensor AFS, can be changed arbitrarily at the step S155 of the flowchart shown in FIG. 8 to optimize the operating zone of the air-fuel-ratio sensor AFS.

It should be noted that, in the operation to change the oxygen-concentration-detection voltage, that is, a voltage applied between the plus-side terminal AF+ and the minus-side terminal AF− of the air-fuel-ratio sensor AFS to detect an air-fuel ratio, a transient change generating a fast response like the detection of an alternating-current element admittance Y is not required. Thus, in configuration of the air-fuel-ratio detecting apparatus 41 wherein the variable voltage applied to the plus-side terminal AF+ of the air-fuel-ratio sensor AFS is changed by a simple D/A converter, there is no problem.

In the third embodiment, on the other hand, the simple D/A converter embedded in the microcomputer 2, the operational amplifier OP4 and the resistors R13, R14 and R21 function as the second voltage applying means.

In addition, the air-fuel-ratio sensor AFS employed in the third embodiment is connected reversely to the first embodiment. Thus, a voltage Vi(t2) determined at the step S160 to be higher than the reference voltage indicates that the magnitude of the present sensor current I is not greater than the predetermined magnitude in the dynamic range. In this case, the flow of the detection processing proceeds to the step S170 at which the microcomputer 2 puts the transistor Tr1 in a turned-on state, lowering the level of the voltage applied to the minus-side terminal AF− of the air-fuel-ratio sensor AFS. Thus, the oxygen-concentration-detection voltage applied across the air-fuel-ratio sensor AFS rises instead of going down.

By the same token, a voltage Vi(t2) determined at the step S160 to be lower than the reference voltage indicates that the magnitude of the present sensor current I is greater than the predetermined magnitude in the dynamic range. In this case, the flow of the detection processing proceeds to the step S180 at which the microcomputer 2 puts the transistor Tr2 in a turned-on state, raising the level of the voltage applied to the minus-side terminal AF− of the air-fuel-ratio sensor AFS. Thus, the oxygen-concentration-detection voltage applied across the air-fuel-ratio sensor AFS goes down instead of rising.

As a result, much like the air-fuel-ratio detecting apparatus 1 implemented by the first embodiment, in an operation to detect an element admittance Y carried out by the air-fuel-ratio detecting apparatus 41 implemented by the third embodiment, the element admittance Y can be detected without causing the sensor current I to go beyond the dynamic range.

Some embodiments of the present invention have been explained so far. It should be noted that the scope of the present invention is not limited to these embodiments. That is, a variety of changes can be made.

For example, in the case of the air-fuel-ratio detecting terminals 1 and 31 implemented by the first and second embodiments respectively, the voltage Vo applied to the plus-side terminal AF+ of the air-fuel-ratio sensor AFS is changed in an operation to detect an element admittance Y. It should be noted that the air-fuel-ratio detecting terminals can also be designed into a configuration wherein it is the voltage applied to the minus-side terminal AF− of the air-fuel-ratio sensor AFS that is changed in an operation to detect an element admittance Y.

As described above, in an operation to detect an element admittance Y carried out by the air-fuel-ratio detecting apparatus 41 implemented by the third embodiment, the voltage applied to the minus-side terminal AF− of the air-fuel-ratio sensor AFS is changed by activating a voltage divider. It should be noted, however, that the air-fuel-ratio detecting apparatus 41 can also designed into a configuration wherein it is the voltage applied to the plus-side terminal AF+ of the air-fuel-ratio sensor AFS that is changed by activating a voltage divider in an operation to detect an element admittance Y as is the case with the first embodiment. In this case, it is the voltage applied to the minus-side terminal AF− of the air-fuel-ratio sensor AFS that is changed by the simple D/A converter embedded in the microcomputer 2.

In addition, in the air-fuel-ratio detecting apparatus 41 implemented by the third embodiment, a constant voltage of typically 3.0 V is supplied to the non-inverting input terminal of the operational amplifier OP5 from the output terminal DAC2 of the microcomputer 2. It should be noted, however, that the air-fuel-ratio detecting apparatus 41 can also be designed into a configuration wherein the constant voltage is generated by a voltage divider for example instead of the output terminal DAC2 of the microcomputer 2.

Furthermore, the air-fuel-ratio detecting apparatuses 1, 31 and 41 implemented by the first, second and third embodiments respectively as described above, 2 voltage switching circuits, namely, the transistor Tr1 used in conjunction with the resistor R16 and the transistor Tr2 used in conjunction with the resistor R17, are employed. It should be noted, however, that even only one voltage switching circuit will also work. In such a configuration, by turning the voltage switching circuit on or off, the voltage applied to the air-fuel-ratio sensor AFS can be either raised or lowered.

In addition, the transistors Tr1 and Tr2 are connected with the resistors R16 and R17 respectively in the air-fuel-ratio detecting apparatuses 1, 31 and 41 implemented by the first, second and third embodiments respectively in wiring orders shown in FIGS. 1, 6 and 7 respectively. It is worth noting, however, that the wiring orders the transistors Tr1 and Tr2 are connected with the resistors R16 and R17 respectively is not limited to those shown in FIGS. 1, 6 and 7. For example, they can be connected in reversed wiring orders which are not shown in the figures. Nevertheless, the wiring orders adopted by the first, second and third embodiments offer a merit that the transistors Tr1 and Tr2 can be put in a turned-on state or a turned-off state by signals generated by the microcomputer 2 in a simple way and with a high degree of reliability.

By the way, as an oxygen concentration sensor, the air-fuel-ratio detecting apparatuses 1, 31 and 41 implemented by the first, second and third embodiments each employ an air-fuel-ratio sensor AFS having a shape resembling a cup as shown in FIG. 2 whereby an air-fuel ratio is found by detecting a limit current flowing through the sensor AFS. It should be noted, however, that the present invention can also be applied to an air-fuel-ratio detecting apparatus employing an air-fuel-ratio sensor of the stacked-layer type including 2 solid electrolyte layers forming the so-called pumping and sensing cells as an oxygen concentration sensor.

(Fourth Embodiment)

Figure 10:
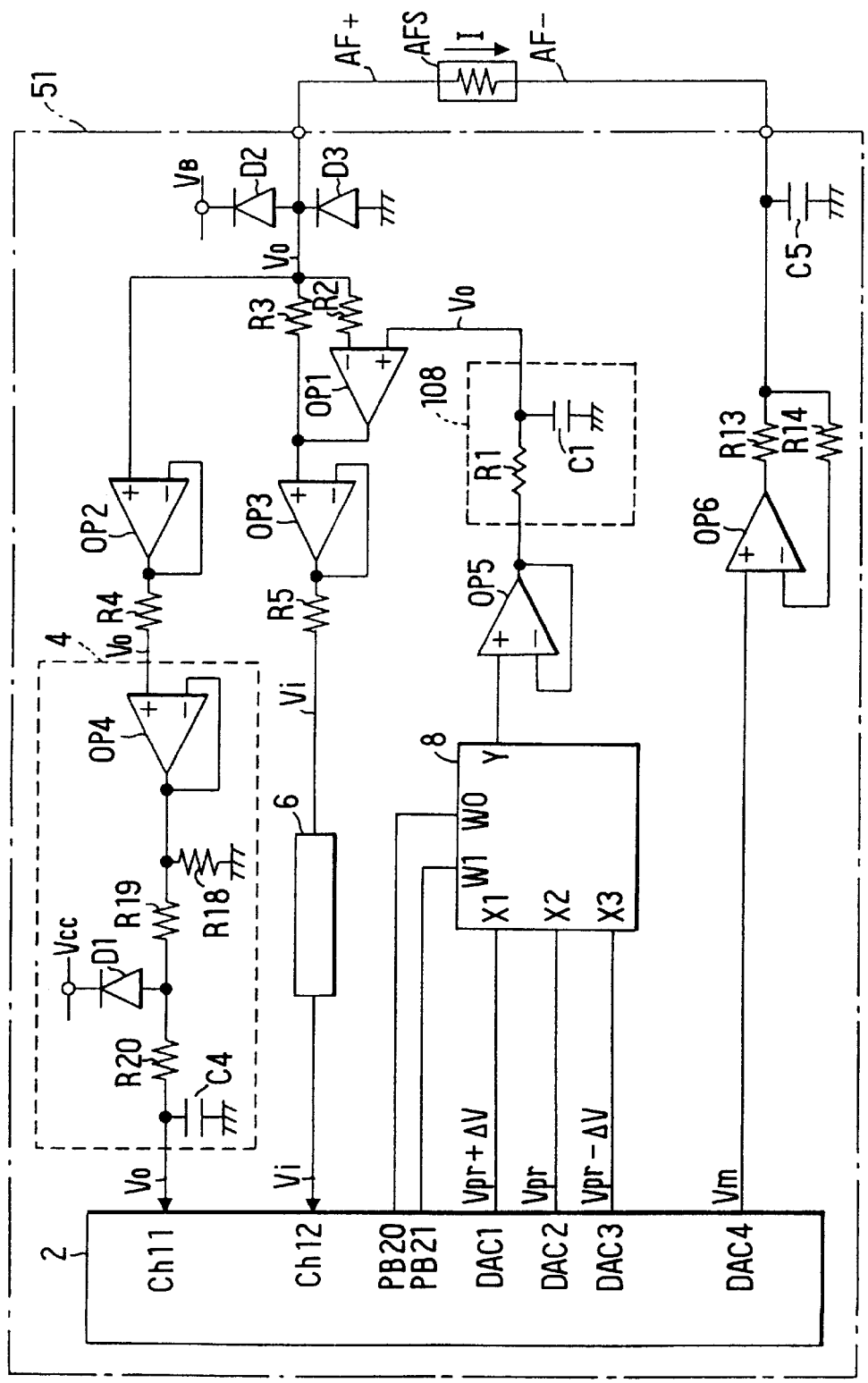
FIG. 10 is a circuit diagram showing an air-fuel-ratio detecting apparatus of a fourth embodiment of the present invention.

FIG. 10 is a circuit diagram showing an air-fuel-ratio detecting apparatus 51 implemented by a fourth embodiment of the present invention.

As shown in FIG. 10, the air-fuel-ratio sensor AFS of the limit-current type shown in FIG. 2 is connected to the air-fuel-ratio detecting apparatus 51 and used as an oxygen concentration sensor. The air-fuel-sensor-ratio sensor AFS is installed on an exhaust pipe 10 as shown in FIG. 2. The exhaust pipe 10 is extended from the main body of an engine which is shown in none of the figures. For an oxygen-concentration-detection voltage applied to the air-fuel-ratio sensor AFS, a sensor current I proportional to the concentration of oxygen contained in gas exhausted by the engine flows through the sensor AFS.

As shown in FIG. 10, the air-fuel-ratio detecting apparatus 51 is provided with a microcomputer 2 having an embedded A/D converter and embedded simple D/A converter which are not shown in the figure. The two terminals ch11 and ch12 of the microcomputer 2 are input terminals of the embedded A/D converter whereas the 4 terminals DAC1, DAC2, DAC3 and DAC4 of the microcomputer 2 are output terminals of the embedded D/A converter. The 2 other terminals PB20 and PB21 of the microcomputer 2 are output terminals of an ordinary output port of the microcomputer 2.

Encircled by a dashed line in FIG. 10, the input circuit 4 includes an operational amplifier OP4 which serves as a buffer. A non-inverting input terminal of the operational amplifier OP4 is used as the input terminal of the input circuit 4. An output terminal and an inverting input terminal of the operational amplifier OP4 are connected to each other. A pull-down resistor R18 is connected between the output terminal of the operational amplifier OP4 and a ground potential GND of 0 V. One end of a resistor R19 is connected to the output terminal of the operational amplifier OP4 and the other end of the resistor R19 is connected to an anode of a diode D1 serving as an over-voltage protection component. A cathode of the diode D1 is connected to a power-supply voltage Vcc which is set at a level of 5V in the case of this embodiment. One end of a resistor R20 is used as the output terminal of the input circuit 4 and the other end of the resistor R20 is connected to the anode of the diode D1. Used for eliminating noise, a capacitor C4 is connected between the ground potential GND and the output terminal of the input circuit 4 which is connected to the input terminal ch11 of the microcomputer 2. As described above, the input terminal of the input circuit 4, that is, the non-inverting input terminal of the operational amplifier OP4, is connected to the output terminal of the operational amplifier OP2 by the resistor R4 and the output terminal of the input circuit 4, that is, a point of junction between one end of the resistor R20 and one end of the capacitor C4, is connected directly to the input terminal ch11 of the microcomputer 2. The input circuit 6 has exactly the same configuration as the input circuit 4.

One end of a resistor R1 is connected to a non-inverting input terminal of the operational amplifier OP1. A capacitor C1 is connected between the non-inverting input terminal of the operational amplifier OP1 and the ground potential GND. The capacitor C1 forms a low-pass filter 108 in conjunction with the resistor R1. A voltage Vo appearing at the output terminal of the low-pass filter 108, that is, a point of junction between the capacitor C1 and the resistor R1, is supplied to the non-inverting input terminal of the operational amplifier OP1.

In particular, the air-fuel-ratio detecting apparatus 51 implemented by the fourth embodiment includes a multiplexer 8 with 3 input terminals X1, X2 and X3, an output terminal Y and select terminals W0 and W1. The multiplexer 8 selects one of signals supplied to the input terminals X1, X2 and X3 in accordance with the levels of signals supplied to the select terminals W0 and W1, outputting the selected signal to the output terminal Y. The input terminals X1, X2 and X3 are connected respectively to the output terminals DAC1, DAC2 and DAC3 of the simple D/A converter embedded in the microcomputer 2. On the other hand, the select terminals W0 and W1 are connected to the output terminals PB20 and PB21 of the microcomputer 2 respectively.

To put it in detail, with both the voltages supplied to the select terminals W0 and W1 set at the low level, the multiplexer 8 selects the signal supplied to the input terminal X1 and outputs the selected signal to the output terminal Y. With the signal supplied to the select terminal W0 set at the high level of 5 V while the signal supplied to the select terminal W1 set at the low level, the multiplexer 8 selects the signal supplied to the input terminal X2, outputting the selected signal to the output terminal Y. With both the voltages supplied to the select terminals W0 and W1 set at the high level, the multiplexer 8 selects the signal supplied to the input terminal X3 and outputs the selected signal to the output terminal Y.

In addition, the air-fuel-ratio detecting apparatus 51 also includes an operational amplifier OP5. The output terminal Y of multiplexer 8 is connected to a non-inverting input terminal of the operational amplifier OP5. An output terminal and an inverting input terminal of the operational amplifier OP5 are connected to each other. In such a configuration, a voltage appearing at the output terminal Y of the multiplexer 8 is supplied to the input terminal of the low-pass filter 108 through the output terminal of the operational amplifier OP5. The output terminal of the low-pass filter 108 is the other end of the resistor R1 cited above, that is, the end of the resistor R1 not connected to the non-inverting input terminal of the operational amplifier OP1. Furthermore, the air-fuel-ratio detecting apparatus 51 also includes an operational amplifier OP6. A non-inverting input terminal of the operational amplifier OP6 is connected to the output terminal DAC4 of the microcomputer 2. An output terminal of the operational amplifier OP4 is connected to a minus-side terminal AF− of the air-fuel-ratio sensor AFS by a resistor R13. The minus-side terminal AF− is a terminal connected to the exhausted-gas-side electrode layer 26 shown in FIG. 2. An inverting input terminal of the operational amplifier OP6 is also connected to the minus-side terminal AF− of the air-fuel-ratio sensor AFS by a resistor R14.

In addition, the air-fuel-ratio detecting apparatus 51 also includes a capacitor C5 as well as diodes D2 and D3. The capacitor C5 is connected between a signal line from the resistor R13 to the minus-side terminal AF− of the air-fuel-ratio sensor AFS and the ground potential GND. An anode of the diode D2 is connected to a signal line from the shunt resistor R3 to the plus-side terminal AF+ of the air-fuel-ratio sensor AFS. A cathode of the diode D2 is connected to a battery voltage VB of normally 12 V. On the other hand, a cathode of the diode D3 is connected to the signal line from the shunt resistor R3 to the plus-side terminal AF+ of the air-fuel-ratio sensor AFS. An anode of the diode D3 is connected to the ground potential GND. It should be noted that the capacitor C5 is used for preventing a high-voltage surge or high-voltage static electricity from being introduced from the signal line between the air-fuel-ratio detecting apparatus 51 and the minus-side terminal AF− of the air-fuel-ratio sensor AFS into the air-fuel-ratio detecting apparatus 51. By the same token, the two diodes D2 and D3 are used for preventing a high-voltage surge or high-voltage static electricity from being introduced from the signal line between the air-fuel-ratio detecting apparatus 51 and the plus-side terminal AF+ of the air-fuel-ratio sensor AFS into the air-fuel-ratio detecting apparatus 51.

In the air-fuel-ratio detecting apparatus 51 with a configuration described above, a voltage appearing at the output terminal Y of the multiplexer 8 is supplied to the low-pass filter 108 by way of the operational amplifier OP5. On the other hand, a voltage Vo at the same level as the voltage output by the low-pass filter is supplied to the plus-side terminal AF+ of the air-fuel-ratio sensor AFS by a so-called output circuit which comprises the operational circuit OP1, the resistor R2 and the shunt resistor R3.

When the microcomputer 2 writes digital data into the embedded simple D/A converter, the simple D/A converter outputs a plus-side reference voltage Vpr through the output terminal DAC2, a voltage (Vpr+ΔV) through the output terminal DAC1, a voltage (Vpr−ΔV) through the output terminal DAC3 and a minus-side reference voltage Vm through the output terminal DAC4. The plus-side reference voltage Vpr is a voltage to be applied to the plus-side terminal AF+ of the air-fuel-ratio sensor AFS. Considering the oxygen-concentration-detection voltage of the present invention or the voltage applied to the air-fuel-ratio sensor AFS to be a difference between 2 electric potentials, the plus-side reference voltage Vpr is one of the electric potentials while the minus-side reference voltage Vm is the other electric potential. On the other hand, the minus-side reference voltage Vm is a voltage to be applied to the minus-side terminal AF− of the air-fuel-ratio sensor AFS. The voltage (Vpr+ΔV) is higher than the plus-side reference voltage Vpr by a predetermined voltage difference ΔV while the voltage (Vpr−ΔV) is lower than the plus-side reference voltage Vpr by the predetermined voltage difference ΔV. In this embodiment, the predetermined voltage difference ΔV is 0.2 V.

When the microcomputer 2 sets the signal output through the output terminal PB20 at the high level and the signal output through the output terminal PB21 at the low level, the plus-side reference voltage Vpr output through the output terminal DAC2 is selected by the multiplexer 8 and applied to the plus-side terminal AF+ of the air-fuel-ratio sensor AFS through the output terminal Y of the multiplexer 8.

When the microcomputer 2 sets both the voltages output through the output terminals PB20 and PB21 at the high level, the voltage (Vpr−ΔV) output through the output terminal DAC3 is selected by the multiplexer 8 and applied to the plus-side terminal AF+ of the air-fuel-ratio sensor AFS through the output terminal Y of the multiplexer 8. That is, a voltage lower than the plus-side reference voltage Vpr by the predetermined voltage difference ΔV of 0.2 V is applied to the plus-side terminal AF+ of the air-fuel-ratio sensor AFS.

When the microcomputer 2 sets both the voltages output through the output terminals PB20 and PB21 at the low level, on the contrary, the voltage (Vpr+ΔV) output through the output terminal DAC1 is selected by the multiplexer 8 and applied to the plus-side terminal AF+ of the air-fuel-ratio sensor AFS through the output terminal Y of the multiplexer 8. That is, a voltage higher than the plus-side reference voltage Vpr by the predetermined voltage difference ΔV of 0.2 V is applied to the plus-side terminal AF+ of the air-fuel-ratio sensor AFS.

On the other hand, the minus-side reference voltage Vm output by the simple D/A converter embedded in the microcomputer 2 through the output terminal DAC4 is supplied to the minus-side terminal AF− of the air-fuel-ratio sensor AFS by way of another output circuit which comprises the operational circuit OP6 and the resistors R13 and R14.

Thus, in a normal operation wherein the microcomputer 2 sets the signal output through the output terminal PB20 at the high level and the signal output through the output terminal PB21 at the low level, the plus-side reference voltage Vpr output through the output terminal DAC2 is applied to the plus-side terminal AF+ of the air-fuel-ratio sensor AFS and the minus-side reference voltage Vm output through the output terminal DAC4 is applied to the minus-side terminal AF− of the air-fuel-ratio sensor AFS. As a result, an oxygen-concentration-detection voltage equal to a difference (Vpr−Vm) between the plus-side reference voltage Vpr and the minus-side reference voltage Vm is applied across the air-fuel-ratio sensor AFS as a voltage for detecting the air-fuel ratio of mixed air. With the oxygen-concentration-detection voltage applied across the air-fuel-ratio sensor AFS, a current representing the concentration of oxygen contained in exhausted gas flows through the air-fuel ratio sensor AFS. As described above, such a current is also referred to as a sensor current I.

Also in the case of the air-fuel-ratio detecting apparatus 51 implemented by the fourth embodiment, a current with a magnitude equal to the sensor current I flowing through the air-fuel ratio sensor flows through the shunt resistor R3 as well. Thus, a difference between electric potentials at the ends of the shunt resistor R3 is proportional to the sensor current I. This electric-potential difference is supplied to the microcomputer 2 as follows. The voltage Vo appearing at the end of the shunt resistor R3 connected to the plus-side terminal AF+ of the air-fuel-ratio sensor AFS, that is, the voltage applied to the plus-side terminal AF+ of the air-fuel-ratio sensor AFS, is supplied to the input terminal ch11 of the microcomputer 2 through the operational amplifier OP2 and the input circuit 4. On the other hand, a voltage Vi having the same potential level as a voltage appearing at the other end of the shunt resistor R3, that is, a voltage output by the operational amplifier OP1, is supplied to the input terminal ch12 of the microcomputer 2 through the operational amplifier OP3 and the input circuit 6.

Figure 11:
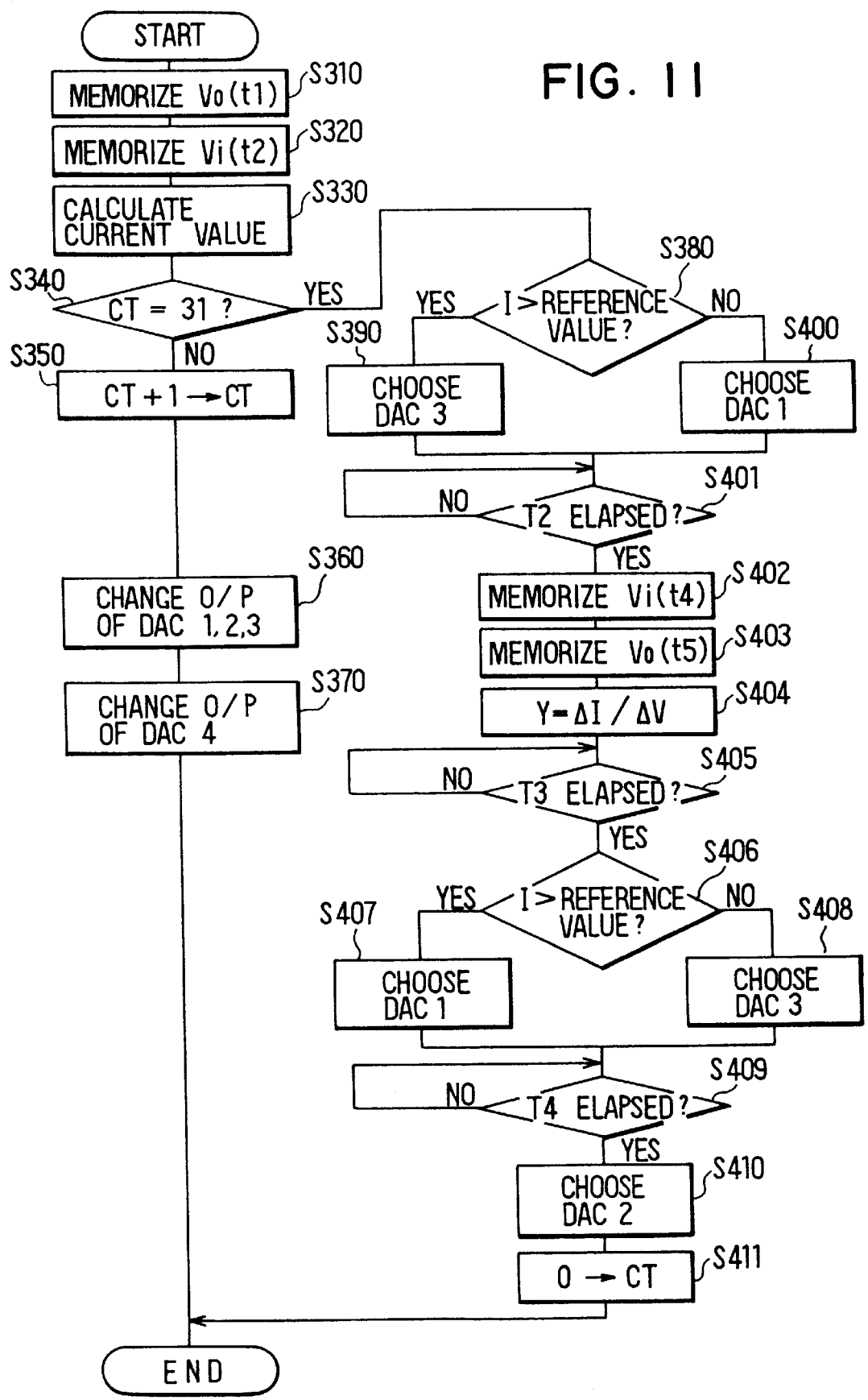
FIG. 11 is a flowchart showing a detection routine carried out by a microcomputer employed in the air-fuel-ratio detecting apparatus according to the fourth embodiment of the present invention.

The microcomputer 2 of the air-fuel-ratio detecting apparatus 51 implemented by the fourth embodiment periodically carries out processing shown in FIG. 11 in order to detect the sensor current I flowing through the air-fuel-ratio sensor AFS. From the magnitude of the sensor current I, the air-fuel ratio of the air-fuel mixture, that is, the concentration of oxygen contained in exhausted gas, and the element admittance Y of the air-fuel-ratio sensor AFS are determined.

Next, the processing carried out by the microcomputer 2 employed in the air-fuel-ratio detecting apparatus 51 to detect the sensor current I by changing the oxygen-concentration-detection voltage applied to the air-fuel-ratio sensor AFS is explained by referring to a flowchart shown in FIG. 11. It should be noted that the detection processing shown in FIG. 11 is carried out at time intervals of 4 ms. In addition, the microcomputer 2 initially sets signals output through the output terminals PB20 and PB21 at levels that drive the multiplexer 8 to select the plus-side reference voltage Vpr generated by the microcomputer 2 through the output terminal DAC2 and apply the voltage Vpr to the plus-side terminal AF+ of the air-fuel-ratio sensor AFS through the output terminal Y of the multiplexer 8. To be more specific the output terminals PB20 and PB21 are initially set at a high level of 5 V and a low level of 0 V respectively.

As shown in FIG. 11, the flowchart begins with step S310 at which the microcomputer 2 starts execution of the detection processing to detect the voltage Vo supplied to the input terminal ch11 and stores the detected voltage Vo as Vo(t1). The flow of the detection processing then goes on to step S320 at which the microcomputer 2 detects the voltage Vi supplied to the input terminal ch12 and stores the detected voltage Vi as Vi(t2).

Then, the flow of the detection processing goes on to step S330 at which the microcomputer 2 computes the magnitude of the sensor current I, that is, the limit current, by division of the difference (Vi(t2)−Vo(t1)) between the voltage Vi(t2) detected at the step S320 and the voltage Vo(t1) detected at the step S310 by the resistance RS of the shunt resistor R3. Then, the microcomputer 2 searches a characteristic map stored in advance in a ROM embedded in the microcomputer 2 for an air-fuel ratio of mixed air (that is, the concentration of oxygen contained in exhausted air) corresponding to the magnitude of the sensor current I.

Subsequently, the flow of the detection processing goes on to step S340 at which the microcomputer 2 examines the value of a counter CT set in a RAM embedded in the microcomputer 2 to determine whether the counter CT has a typical value of 31 corresponding to a predetermined period T1 (=128 ms). If the value of the counter CT is not 31, the flow of the detection processing then goes on to step S350 at which the microcomputer 2 increments the value of the counter CT by 1.

The flow of the detection processing then proceeds to step S360 at which the plus-side reference voltage Vpr output through the output terminal DAC2 is changed. Then, the signal output through the output terminal DAC1 is also updated to a level (Vpr+ΔV) higher than the changed plus-side reference voltage Vpr by a difference Δ V of 0.2 V. Subsequently, the signal output through the output terminal DAC3 is also updated to a level (Vpr−ΔV) lower than the changed plus-side reference voltage Vpr by a difference ΔV of 0.2 V. That is, the signal output through the output terminal DAC1 is always set at a level (Vpr+ΔV) higher than the plus-side reference voltage Vpr output through the output terminal DAC2 by a difference ΔV of 0.2 V while the signal output through the output terminal DAC3 is always set at a level (Vpr−ΔV) lower than the plus-side reference voltage Vpr by a difference ΔV of 0.2 V.

The flow of the detection processing then continues to step S370 at which the minus-side reference voltage Vm output through the output terminal DAC4 is changed before the detection processing is ended.

The processing of the step S360 is carried out when it is deemed necessary to change the plus-side reference voltage Vpr in accordance with conditions such as the operating state of the engine. By the same token, the processing of the step S370 is carried out when it is deemed necessary to change the minus-side reference voltage Vm. For example, an oxygen-concentration-detection voltage or an air-fuel-ratio-detection voltage is found from the chain line L1 shown in FIG. 3 for the most recent air-fuel ratio found at the step S330. Then, the processing of the step S360 is carried out to change the plus-side reference voltage Vpr and the processing of the step S370 is carried out to change the minus-side reference voltage Vm so that the difference (Vpr−Vm) is equal to the oxygen-concentration-detection voltage.

It should be noted, however, that the processing of the steps S360 and S370 to change the voltages output through the output terminals DAC1 to DAC4 is carried out in order to optimize the operating zone of the air-fuel-ratio sensor AFS in the normal operation to detect an air-fuel ratio. Thus, at the steps S360 and S370, instead of changing the voltages output through the output terminals DAC1 to DAC4, the signals are varied gradually by a predetermined small change at one time so that the sensor current I does not change abruptly during the normal operation. In the fourth embodiment, the small change is set at a typical value of 5 mV. For more information, refer to an ellipse enclosed by a dashed line shown in FIG. 13.

In addition, the processing of the steps S360 and S370 to change the voltages output through the output terminals DAC1 to DAC4 is carried out by updating digital contents of target-value registers for the output terminals DAC1 to DAC4 which compose a group of registers in the simple D/A converter. In this way, the voltages appearing at the output terminals DAC1 to DAC4 change within a period of time not longer than a maximum response delay time Tdmax of the simple D/A converter which is about 48 microseconds in the case of the fourth embodiment.

On the other hand, a value of the counter CT determined at the step S340 to be 31 indicates that it is time to detect the element admittance Y of the air-fuel-ratio sensor AFS. In this case, the flow of the detection processing goes on to step S380 at which the microcomputer 2 determines whether the magnitude of the sensor current I found at the step S330 is greater than a reference value determined in advance. The reference value is a value in the dynamic range of the voltage-current characteristic of the air-fuel-ratio sensor AFS shown in FIG. 3. The dynamic range is a current-detection range in which a sensor current is detected for an oxygen-concentration-detection voltage applied to the air-fuel-ratio sensor AFS and the reference value is typically the magnitude of a current at the center of the dynamic range.

Figure 12A:
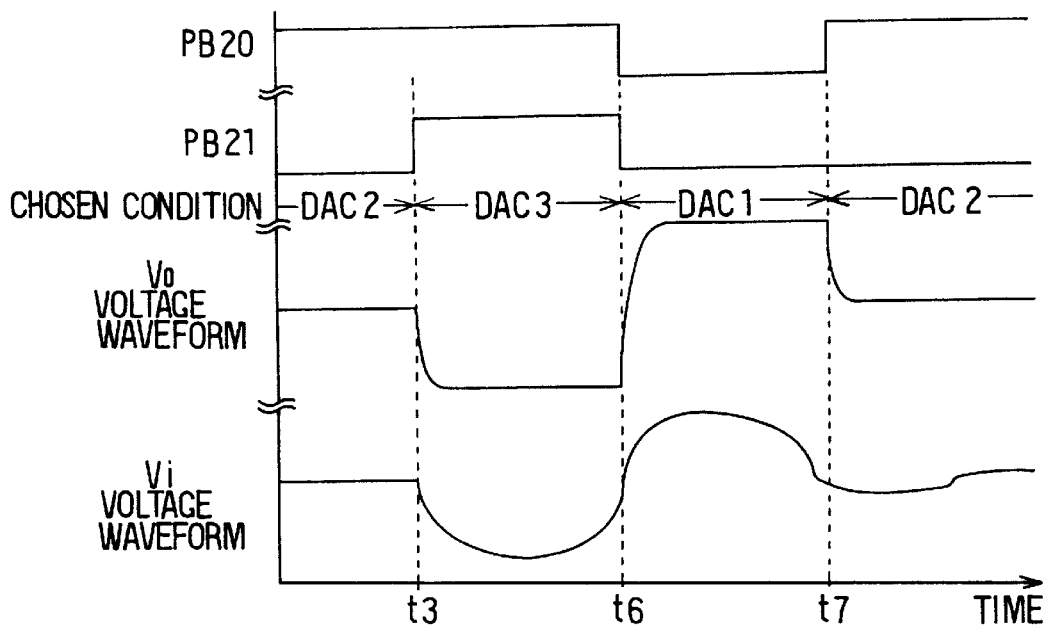
FIGS. 12A and 12B are time charts showing changing operations of the voltage applied to an air-fuel-ratio sensor carried out by a multiplexer according to the fourth embodiment of the present invention.

If the result of the determination of the step S380 is an affirmation, that is, if the magnitude of the sensor current I is determined at the step S380 to be greater than the reference value in the dynamic range, the flow of the detection processing proceeds to step S390 at which the microcomputer 2 changes the voltage output by the output terminal PB21 from the low level to the high level at a point of time t3 of the timing charts shown in FIG. 12A so that both the voltages appearing at the output terminals PB20 and PB21 are set at the high level to drive the multiplexer 8 to select the voltage output by the microprocessor 2 through the output terminal DAC3. Then, the flow of the detection processing proceeds to step S401. That is, at the point of time t3, the voltage (Vp−ΔV) output by the microprocessor 2 through the output terminal DAC3 is applied to the plus-side terminal AF+ of the air-fuel-ratio sensor AFS through the output terminal Y of the multiplexer 8 before the flow of the detection processing proceeds to the step S401.

Thus, at the point of time t3, the voltage Vo applied to the plus-side terminal AF+ of the air-fuel-ratio sensor AFS changes to the voltage (Vpr−ΔV) which is lower than the plus-side reference voltage Vpr by the difference ΔV of 0.2

V described earlier as shown in FIG. 12A. Accompanying the decrease of Vo, the sensor current I and, hence, the voltage Vi supplied to the input terminal ch12, that is, the voltage output by the operational amplifier OP1, also decrease as well.

Figure 12B:
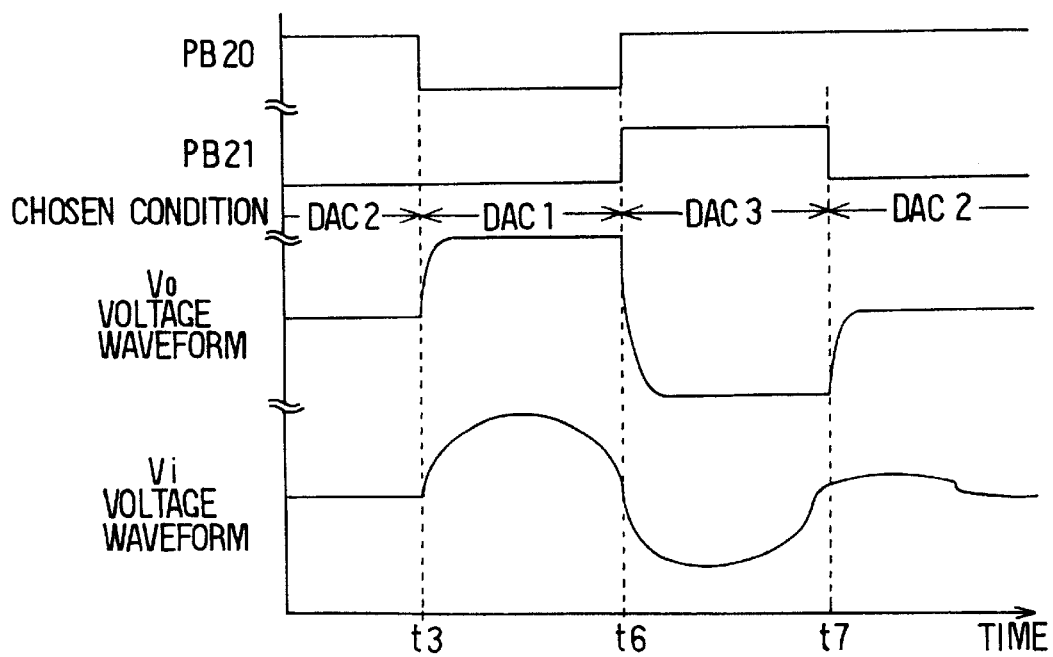

If the result of the determination of the step S380 is a negation, that is, if the magnitude of the sensor current I is determined at the step S380 to be smaller than the reference value in the dynamic range, on the other hand, the flow of the detection processing proceeds to step S400 at which the microcomputer 2 changes the voltage output by the output terminal PB20 from the high level to the low level at a point of time t3 of the timing charts shown in FIG. 12B so that both the voltages appearing at the output terminals PB20 and PB21 are set at the low level to drive the multiplexer 8 to select the voltage output by the microprocessor 2 through the output terminal DAC1. Then, the flow of the detection processing proceeds to the step S401. That is, at the point of time t3, the voltage (Vpr+ΔV) output by the microprocessor 2 through the output terminal DAC1 is applied to the plus-side terminal AF+ of the air-fuel-ratio sensor AFS through the output terminal Y of the multiplexer 8 before the flow of the detection processing proceeds to the step S401.

Thus, at the point of time t3, the voltage Vo applied to the plus-side terminal AF+ of the air-fuel-ratio sensor AFS changes to the voltage (Vpr+ΔV) which is higher than the plus-side reference voltage Vpr by the difference ΔV of 0.2 V described earlier as shown in FIG. 12B. Accompanying the increase of Vo, the sensor current I and, hence, the voltage Vi supplied to the input terminal ch12, that is, the voltage output by the operational amplifier OP1, also increase as well.

At the step S401, the microcomputer 2 determines whether a period of time T2 of typically 135 microseconds has elapsed since completion of the processing of the step S390 or S400. At the end of the period of time T2, the transient change ΔI in sensor current I is expected to reach a peak. The microcomputer 2 repeats the processing of the step S401, waiting for the period of time T2 to lapse. As the microcomputer 2 determines that the period of time T2 has elapsed, the flow of the detection processing then goes on to step S402 at which the microcomputer 2 detects the voltage Vi supplied to the input terminal ch12 and stores the detected voltage Vi as Vi (t4). Then, the flow of the detection processing then goes on to step S403 at which the microcomputer 2 detects the voltage Vo supplied to the input terminal ch11 and stores the detected voltage Vo as Vo(t5).

Then, the flow of the detection processing then goes on to step S404 at which an element admittance Y, that is, the reciprocal of the element resistance, is computed according to the equation (1) as follows:

$$Y = \frac{\Delta I}{\Delta V} \quad (1)$$
$$= \frac{\{Vi(t2) - Vo(t1)\} - \{Vi(t4) - Vo(t5)\}}{\{Vo(t1) - Vo(t5) \times Rs\}}$$

Then, the flow of the detection processing proceeds to step S405 at which the microcomputer 2 determines whether a period of time T3 of typically 200 microseconds has elapsed since completion of the processing of the step S390 or S400. The microcomputer 2 repeats the processing of the step S405, waiting for the period of time T3 to lapse. As the microcomputer 2 determines that the period of time T3 has elapsed, the flow of the detection processing goes on to step S406 at which the microcomputer 2 determines whether the magnitude of the sensor current I found at the step S330 is greater than a reference value determined in advance as the microprocessor 2 did at the step S380.

If the result of the determination of the step S406 is an affirmation (YES), that is, if the magnitude of the sensor current I is determined at the step S406 to be greater than the reference value in the dynamic range, the flow of the detection processing proceeds to step S407 at which the microcomputer 2 sets both the voltages appearing at the output terminals PB20 and PB21 at the low level to drive the multiplexer 8 to select the voltage output by the microprocessor 2 through the output terminal DAC1. Then, the flow of the detection processing proceeds to step S409. That is, at the point of time t6 of the timing charts shown in FIG. 12A, the voltage (Vpr+ΔV) output by the microprocessor 2 through the output terminal DAC1 is applied to the plus-side terminal AF+ of the air-fuel-ratio sensor AFS through the output terminal Y of the multiplexer 8 before the flow of the detection processing proceeds to the step S409.

Thus, at the point of time t6, the voltage Vo applied to the plus-side terminal AF+ of the air-fuel-ratio sensor AFS changes to the voltage (Vpr+ΔV) which is higher than the plus-side reference voltage Vpr by the difference ΔV of 0.2 V described earlier as shown in FIG. 12A. Accompanying the increase of Vo, the sensor current I and, hence, the voltage Vi supplied to the input terminal ch12, that is, the voltage output by the operational amplifier OP1, also increase as well.

If the result of the determination of the step S406 is a negation (NO), that is, if the magnitude of the sensor current I is determined at the step S406 to be smaller than the reference value in the dynamic range, on the other hand, the flow of the detection processing proceeds to step S408 at which the microcomputer 2 sets both the voltages appearing at the output terminals PB20 and PB21 at the high level to drive the multiplexer 8 to select the voltage output by the microprocessor 2 through the output terminal DAC3. Then, the flow of the detection processing proceeds to the step S409. That is, at the point of time t6 of the timing charts shown in FIG. 12B, the voltage (Vpr−ΔV) output by the microprocessor 2 through the output terminal DAC3 is applied to the plus-side terminal AF+ of the air-fuel-ratio sensor AFS through the output terminal Y of the multiplexer 8 before the flow of the detection processing proceeds to the step S409.

Thus, at the point of time t6, the voltage Vo applied to the plus-side terminal AF+ of the air-fuel-ratio sensor AFS changes to the voltage (Vpr−ΔV) which is lower than the plus-side reference voltage Vpr by the difference ΔV of 0.2 V described earlier as shown in FIG. 12B. Accompanying the decrease of Vo, the sensor current I and, hence, the voltage Vi supplied to the input terminal ch12, that is, the voltage output by the operational amplifier OP1, also decrease as well.

At the step S409, the microcomputer 2 determines whether a period of time T4 of typically 200 microseconds has elapsed since completion of the processing of the step S407 or S408. The microcomputer 2 repeats the processing of the step S409, waiting for the period of time T4 to lapse. As the microcomputer 2 determines that the period of time T4 has elapsed, the flow of the detection processing goes on to step S410 at which the microcomputer 2 sets the voltage output by the output terminal PB21 to the initial low level and sets the voltage output by the output terminal PB20 at the initial high level to drive the multiplexer 8 to again select the voltage appearing at the output terminal DAC2 of the microprocessor 2 at a point of time t7 of the timing charts shown in FIG. 12A or 12B. Thus, at the point of time t7, the plus-side reference voltage Vpr generated by the microcomputer 2 through the output terminal DAC2 is output by the multiplexer 2 through the output terminal Y.

As a result, as shown at the point of time t7 of the time charts shown in FIG. 12A or 12B, the voltage Vo applied to the plus-side terminal AF+ of the air-fuel-ratio sensor AFS is returned to the initial plus-side reference voltage Vpr prior to t3. Accordingly, the sensor current I and the voltage Vi supplied to the input terminal ch12 are also returned to their initial values as well.

Finally, the flow of the detection processing goes on to step S411 at which the microcomputer 2 resets the value of the counter CT to 0, ending the detection processing.

Briefly, in the detection processing represented by the flowchart shown in FIG. 11, the counter CT for counting time units is reset at the step S411, incremented at the step S350 and examined at the step S340. If the predetermined period of time T1 of 128 ms to detect the element admittance Y is found to have not elapsed at the step S340, that is, if the result of the determination at the step S340 is NO, the simple D/A converter changes the voltages output through the output terminals DAC1 to DAC4 at the steps S360 and S370.

Figure 13:
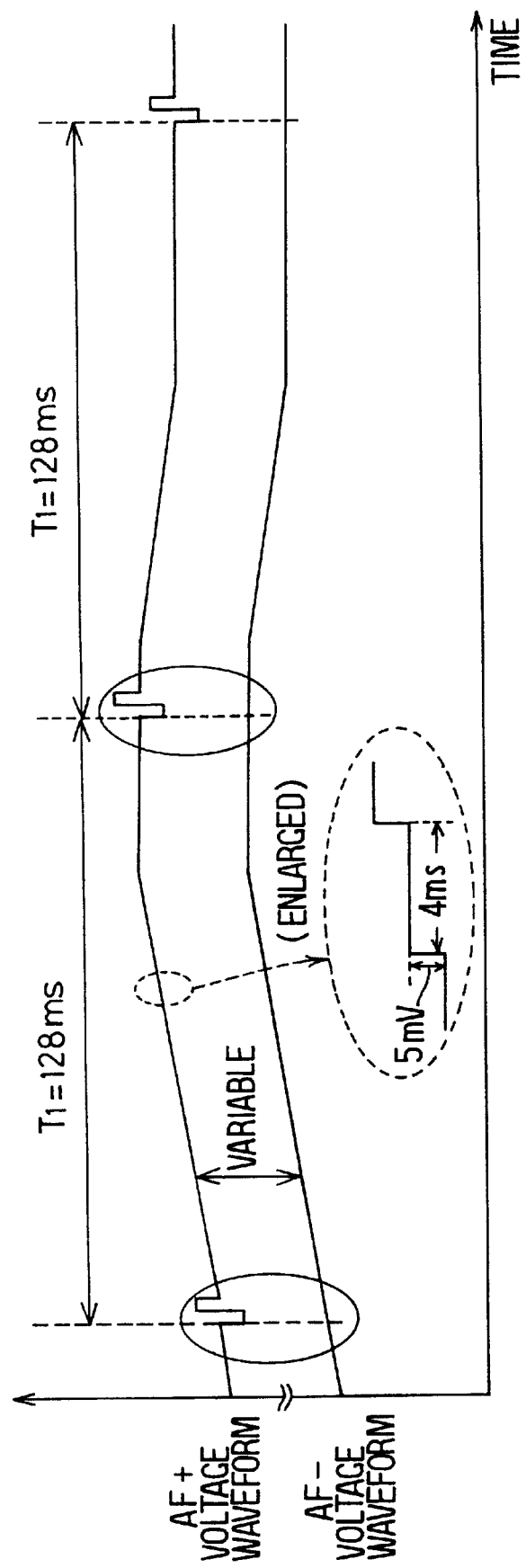
FIG. 13 is a time chart showing operations of the detection processing in FIG. 11 according to the fourth embodiment of the present invention.

To put it in detail, in a normal operation wherein the element admittance Y is not detected, the plus-side reference voltage Vpr applied to the plus-side terminal AF+ of the air-fuel-ratio sensor AFS and the minus-side reference voltage Vm applied to the minus-side terminal AF− of the air-fuel-ratio sensor AFS are raised or lowered by typically 5 mV at time intervals of typically 4 ms, the period of detection of the oxygen concentration, as shown by an ellipse enclosed by a dashed line in FIG. 13. In the example shown in FIG. 13, the plus-side reference voltage Vpr and the minus-side reference voltage Vm are raised or lowered in exactly the same way. It should be noted, however, that the plus-side reference voltage Vpr and the minus-side reference voltage Vm can also be changed in directions opposite to each other or, as another alternative, only one of the plus-side reference voltage Vpr and the minus-side reference voltage Vm is changed.

If the predetermined period of time T1 of 128 ms to detect the element admittance Y is found to have elapsed at the step S340 of the flowchart shown in FIG. 11, that is, if the result of the determination at the step S340 is YES, on the other hand, the processing to change the voltages output through the output terminals DAC1 to DAC4 is not carried out. Instead, the processing at the steps S380 to S400 and the steps S405 to S410 is carried out as an applied-voltage changing means to properly set the levels of the select signals output through the output terminals PB20 and PB21 by the ordinary output port of the microprocessor 2 to the select terminals W0 and W1 of the multiplexer 8. In this way, the voltage Vo applied to the plus-side terminal AF+ of the air-fuel-ratio sensor AFS is set to a level higher and lower than the plus-side reference voltage Vpr as shown in FIGS. 12A and 12B.

As a result, the plus-side reference voltage Vpr applied to the plus-side terminal AF+ of the air-fuel-ratio sensor AFS changes to levels higher and lower than the plus-side reference voltages at time intervals T1 of 128 ms as shown by ellipses each enclosed by a solid line in FIG. 13. It should be noted that FIG. 13 shows an example wherein the plus-side reference voltage Vpr applied to the plus-side terminal AF+ of the air-fuel-ratio sensor AFS is decreased before being increased and returned to its original level as is indicated by the timing charts shown in FIG. 12A.

Figure 14:
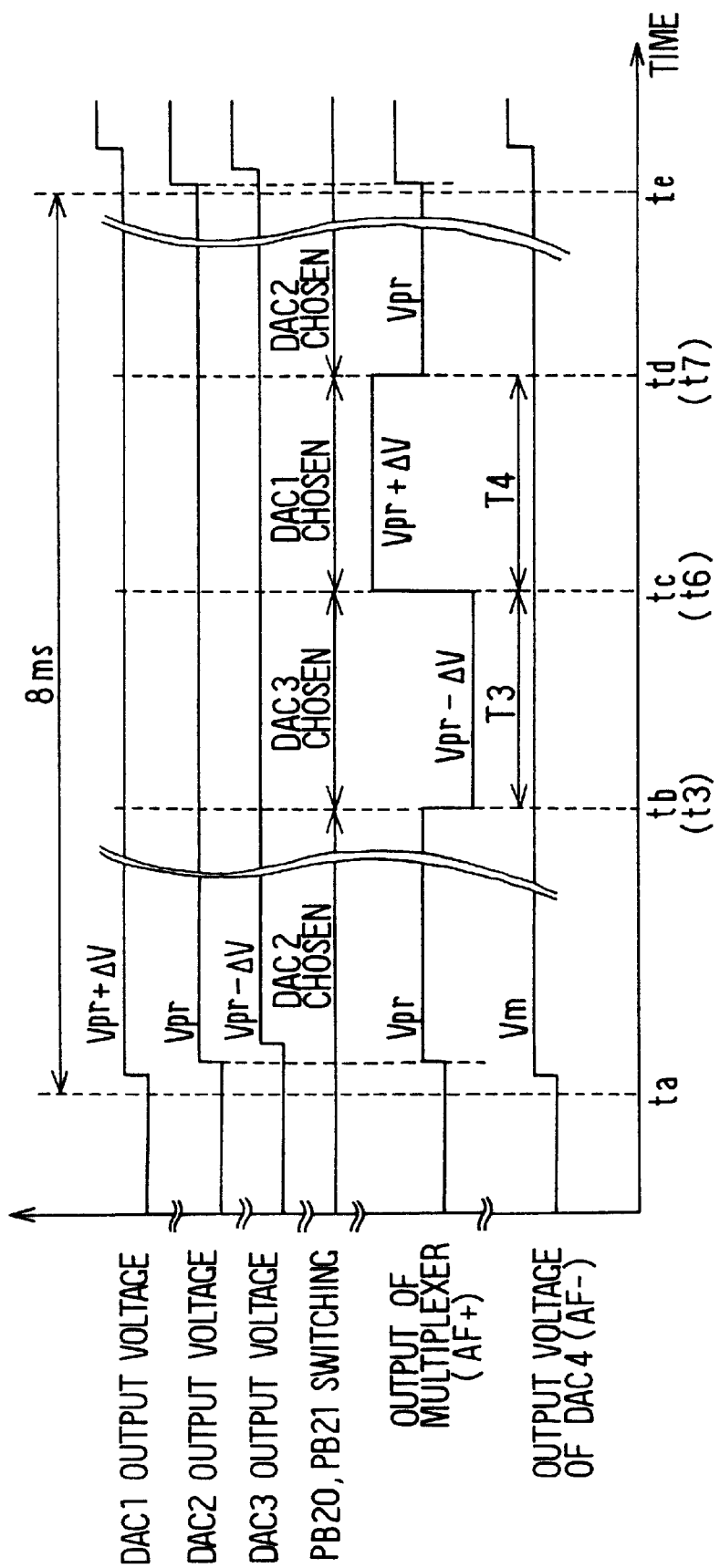
FIG. 14 is a time chart showing detailed changes in voltages of portions of FIG. 13 each enclosed in a solid-line ellipses according to the fourth embodiment of the present invention.

The effect of the detection processing represented by the flowchart shown in FIG. 11 is explained in more detail by referring to FIG. 14 showing timing charts for the portion enclosed by the solid-line ellipse shown in FIG. 13.

In the first place, for a value of the counter CT equal to 30, the processing of the steps S360 and S370 is carried out at a point of time ta of the timing chart shown in FIG. 14.

As a result, the voltages appearing at the output terminals DAC1 to DAC4 of the microcomputer 2 change sequentially one after another within a period of time not longer than the maximum response delay time Tdmax of typically about 48 microseconds introduced by the simple D/A converter as shown in FIG. 14. It should be noted that the order the voltage change and the time it takes to change all the voltages vary in dependence on the configuration of the simple D/A converter. At that time, the plus-side reference voltage Vpr output by the microcomputer 2 through the output terminal DAC2 is selected by the multiplexer 8 and applied to the plus-side terminal AF+ of the air-fuel-ratio sensor AFS by way of the output terminal Y of the multiplexer 8. On the other hand, the minus-side reference voltage Vm output by the microcomputer 2 through the output terminal DAC4 is applied to the minus-side terminal AF− of the air-fuel-ratio sensor AFS.

Later on, at a point of time tb of the timing charts shown in FIG. 14 corresponding to the point of time t3 of the timing charts shown in FIGS. 12A and 12B, the detection processing represented by the flowchart shown in FIG. 11 is carried out again. This time, however, the value of the counter CT is found equal to 31 at the step S340. In this case, the processing of the step S390 or S400 is carried out. In this example, it is the processing of the step S390 that is carried out. As described above, the voltage (Vpr−ΔV) output by the microprocessor 2 through the output terminal DAC3 appears at the output terminal Y of the multiplexer 8. As a result, the voltage Vo applied to the plus-side terminal AF+ of the air-fuel-ratio sensor AFS changes to the voltage (Vpr−ΔV) which is lower than the plus-side reference voltage Vpr by the difference ΔV.

Then, at a point of time tc of the timing charts shown in FIG. 14 corresponding to the point of time t6 of the timing charts shown in FIGS. 12A and 12B, that is, at a point of time after the predetermined period of time T3 (=200 microseconds) has elapsed since the point of time tb, the processing of the step S407 or S408 of the flowchart shown in FIG. 11 is carried out. In this example, it is the processing of the step S407 that is carried out. As described above, the voltage (Vpr+ΔV) output by the microprocessor 2 through the output terminal DAC1 appears at the output terminal Y of the multiplexer 8. As a result, the voltage vo applied to the plus-side terminal AF+ of the air-fuel-ratio sensor AFS swings to the voltage (Vpr+ΔV) which is higher than the plus-side reference voltage Vpr by the difference ΔV.

Later on, at a point of time td of the timing charts shown in FIG. 14 corresponding to the point of time t7 the timing charts shown in FIGS. 12A and 12B, that is, at a point of time after the predetermined period of time T4 (=200 microseconds) has elapsed since the point of time tc, the processing of the step S410 of the flowchart shown in FIG. 11 is carried out. As described above, the plus-side reference voltage Vpr output by the microprocessor 2 through the output terminal DAC2 appears at the output terminal Y of the multiplexer 8. As a result, the voltage vo applied to the plus-side terminal AF+ of the air-fuel-ratio sensor AFS is returned to the plus-side reference voltage Vpr.

Then, at a point of time te shown in FIG. 14, the detection processing represented by the flowchart shown in FIG. 11 is carried out again. This time, however, the value of the counter CT is equal to "0" at the step S340, and the result of the determination of the step S340 is a negation (NO). Accordingly, the processing of the steps S360 and S370 are carried out again.

Much like the processing carried out at the point of time ta, the voltages appearing at the output terminals DAC1 to DAC4 of the microcomputer 2 thus change sequentially one after another within a period of time not longer than the maximum response delay time Tdmax of typically about 48 microseconds introduced by the simple D/A converter.

Thereafter, the detection processing represented by the flowchart shown in FIG. 11 is repeated with a time interval of 4 ms to properly change the plus-side and minus-side reference voltages Vpr and Vm and to increment the counter CT by 1 at each execution till the contents of the counter CT are again found equal to 31 at the step S340 to indicate that it is time to detect the element admittance Y.

The transient changes in voltage shown in FIG. 13 are made as described above. The processing of the steps S310 and S320 of the flowchart shown in FIG. 11 is carried out as a first current detecting means for detecting the sensor current I flowing through the air-fuel-ratio sensor AFS as a difference between the voltages Vi(t2) and Vo(t1) appearing at the ends of the shunt resistor R3 in a steady state immediately before the voltage Vo applied to the plus-side terminal AF+ is changed at the step S390 or S400. On the other hand, the processing of the steps S401 to S403 is carried out as a second current detecting means for detecting the sensor current I flowing through the air-fuel-ratio sensor AFS as a difference between the voltages Vi (t4) and Vo(t5) appearing at the ends of the shunt resistor R3 when the result of the determination at the step S401 is YES, that is, after a predetermined period of time T2 of 135 microseconds has elapsed since the voltage Vo applied to the plus-side terminal AF+ is changed at the step S390 or S400.

The processing of the step S404 is carried out as an admittance computing means for calculating the element admittance Y of the air-fuel-ratio sensor AFS from a difference in sensor current I found from the voltages Vo(t1), Vi(t2), Vi (t4) and Vo(t5) detected at the steps S310, S320, S402 and S403 respectively. To be more specific, the difference in sensor current I is a difference between the sensor current I for the period from the point of time t1 to t2 represented by {Vi(t2)−Vo(t1)}/RS] in a steady state immediately before the change in voltage Vo applied to the plus-side terminal AF+ of the air-fuel-ratio sensor AFS and the sensor current I for the period from the point of time t4 to t5 represented by {Vi (t4)−Vo(t5)}/RS] after the predetermined period of time T2 has elapsed since the change in voltage Vo as is the case with the first embodiment.

The processing of the step S330 is carried out as an oxygen-concentration computing means for finding the air-fuel ratio of mixed air or the concentration of oxygen contained in exhausted gas from a limit current of the air-fuel-ratio sensor AFS which is computed as a sensor current I from a difference between the voltages Vi(t2) and Vo(t1) detected at the steps S320 and S310 respectively.

As described in detail above, according to the fourth embodiment, the simple D/A converter embedded in the microcomputer 2 generates 3 voltage with levels different from each other at the output terminals DAC1 to DAC3. One of which is selected by the multiplexer 8 as a voltage Vo to be applied to the plus-side terminal AF+ of the air-fuel-ratio sensor AFS. The 3 voltages are the plus-side reference voltage Vpr output through the output terminal DAC2 to be used for detecting the air-fuel ratio of mixed air, the voltage (Vpr+ΔV) output through the output terminal DAC1 to be used for detection of the element admittance Y and the (Vpr−ΔV) output through the output terminal DAC1 to be used also for detection of the element admittance Y. The microcomputer 2 changes the levels of the select signals output to the select terminals W0 and W1 of the multiplexer 8 through the output terminals PB20 and PB21 respectively to switch the voltage vo applied to the plus-side terminal AF+ of the air-fuel-ratio sensor AFS from the plus-side reference voltage Vpr to the voltage (Vpr+ΔV) or (Vpr−ΔV) and restore the voltage Vo back to the voltage Vpr. Thus, it is possible to detect the sensor current I that flows through the air-fuel-ratio sensor AFS after the predetermined period of time T2 has elapsed since the actual transient change in voltage Vo with a high degree of reliability.

As a result, the element admittance Y of the air-fuel-ratio sensor AFS can be detected with a high degree of accuracy by changing the voltage Vo applied to the air-fuel-ratio sensor AFS. In addition, it is possible to accurately execute feedback control of the heater 23 for maintaining the activated state of the air-fuel-ratio sensor AFS and to identify the degree to which the sensor AFS has been deteriorated.

Furthermore, the simple D/A converter embedded in the microcomputer 2 outputs the voltage (Vpr+ΔV) higher than the plus-side reference voltage Vpr by the difference ΔV and the (Vpr−ΔV) lower than the plus-side reference voltage Vpr by the difference ΔV to the plus-side terminal AF+ of the air-fuel-ratio sensor AFS by way of the multiplexer 8 to raise or lower the level of the voltage Vo applied to the plus-side terminal AF+ in detection of the element admittance Y of the sensor AFS. Thus, when the applied voltage is returned to its original level, electric charge can be discharged from capacitance components of the air-fuel-ratio sensor AFS in a short period of time. The capacitance components include a particle-boundary capacitance on a particle boundary face of the solid electrolyte layer 24 and an electrode boundary-face capacitance. As a result, the sensor current I can be stabilized quickly to its steady-state magnitude after the element admittance Y of the air-fuel-ratio sensor AFS has been detected.

In addition, the plus-side reference voltage Vpr for detection of the air-fuel ratio of mixed air, the voltage (Vpr+ΔV) and the (Vpr−ΔV) for detection of the element admittance Y generated by the simple D/A converter can be changed arbitrarily. Thus, by properly changing the plus-side reference voltage Vpr, the operating range of the air-fuel-ratio sensor AFS can be optimized during a normal operation to detect the air-fuel ratio of mixed air. Moreover, by changing the voltage Vo applied to the plus-side terminal AF+ of the air-fuel-ratio sensor AFS from the plus-side reference voltage Vpr to the voltage (Vpr+ΔV) or the (Vpr−ΔV) in an operation to detect the element admittance Y, the admittance Y can be detected with a high degree of reliability.

In addition, the simple D/A converter outputs the minus-side reference voltage Vm to the minus-side terminal AF− of the air-fuel-ratio sensor AFS through the terminal DC4 which is, unlike the other terminals DAC1 to DAC3, connected to none of the input terminals X1 to X3 of the multiplexer 8. Thus, the minus-side reference voltage Vm applied to the minus-side terminal AF− of the air-fuel-ratio sensor AFS can also be changed, allowing the oxygen-detection voltage applied between the minus-side terminal AF− and the plus-side terminal AF+ of the air-fuel-ratio sensor AFS to be varied over a wide range. As a result, the operating range of the air-fuel-ratio sensor AFS can be optimized during a normal operation to detect the air-fuel ratio of mixed air.

As shown in FIGS. 12A and 12B, if the magnitude of the sensor current I for detecting an air-fuel ratio is determined at the step S380 to be greater than the reference value in the dynamic range, that is, if the result of the determination of the step S380 is YES, the flow of the detection processing proceeds to step S390 at which the microcomputer 2 lowers the voltage Vo applied to the plus-side terminal AF+ of the air-fuel sensor AFS and computes an alternating-current element admittance Y from the transient decrease in voltage Vo and a transient decrease in sensor current I accompanying the transient decrease in voltage Vo. If the magnitude of the sensor current I for detecting an air-fuel ratio is determined at the step S380 to be not greater than the reference value in the dynamic range, that is, if the result of the determination of the step S380 is NO, on the other hand, the flow of the detection processing proceeds to step S400 at which the microcomputer 2 raises the voltage Vo applied to the plus-side terminals AF+ of the air-fuel sensor AFS and computes an alternating-current element admittance Y from the transient increase in voltage Vo and a transient increase in sensor current I accompanying the transient increase in voltage Vo.

Thus, in the detection of an element admittance Y, it is possible to prevent the voltage Vo applied to the plus-side terminals AF+ of the air-fuel sensor AFS from being shifted in a direction departing from the dynamic range with a high degree of reliability. The element admittance Y can therefore be detected without causing the sensor current I to go beyond the dynamic range. As a result, the element admittance Y can be detected with a high degree of accuracy.

(Fifth Embodiment)

Figure 15:
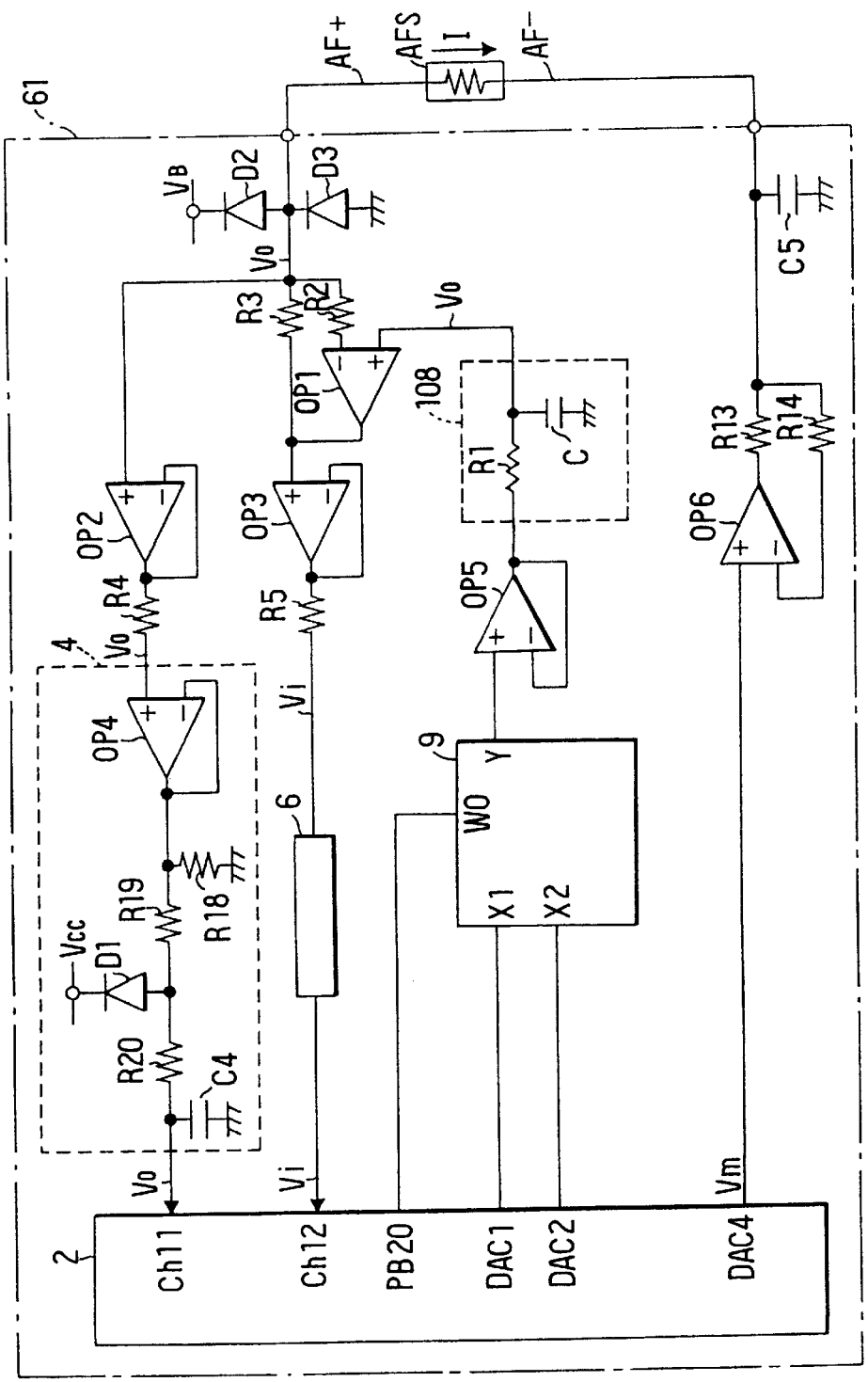
FIG. 15 is a circuit diagram showing an air-fuel-ratio detecting apparatus according to a fifth embodiment of the present invention.
Figure 16:
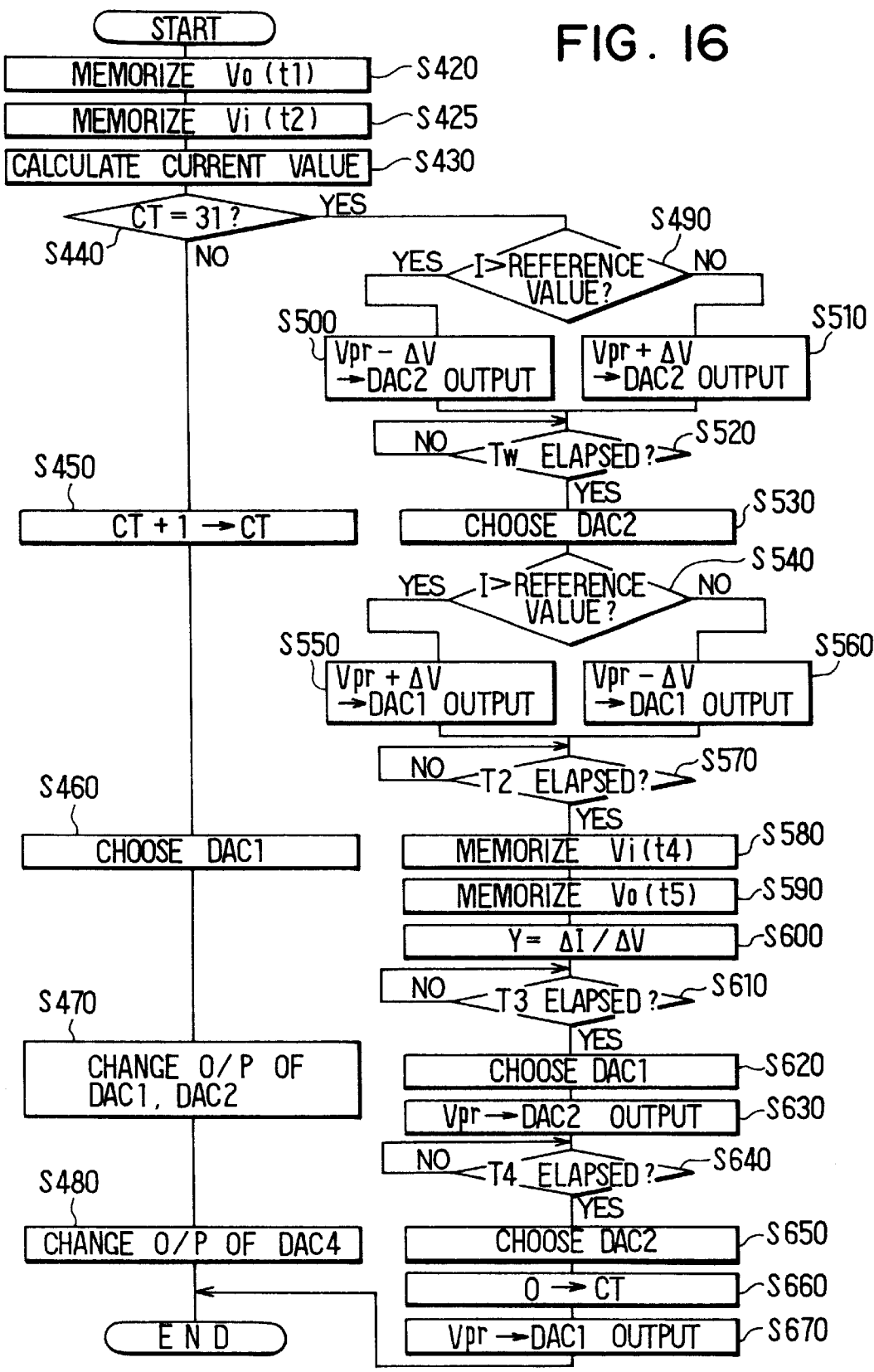
FIG. 16 is a flowchart showing a detection routine carried out by a microcomputer employed in the air-fuel-ratio detecting apparatus according to the fifth embodiment of the present invention.
Figure 17:
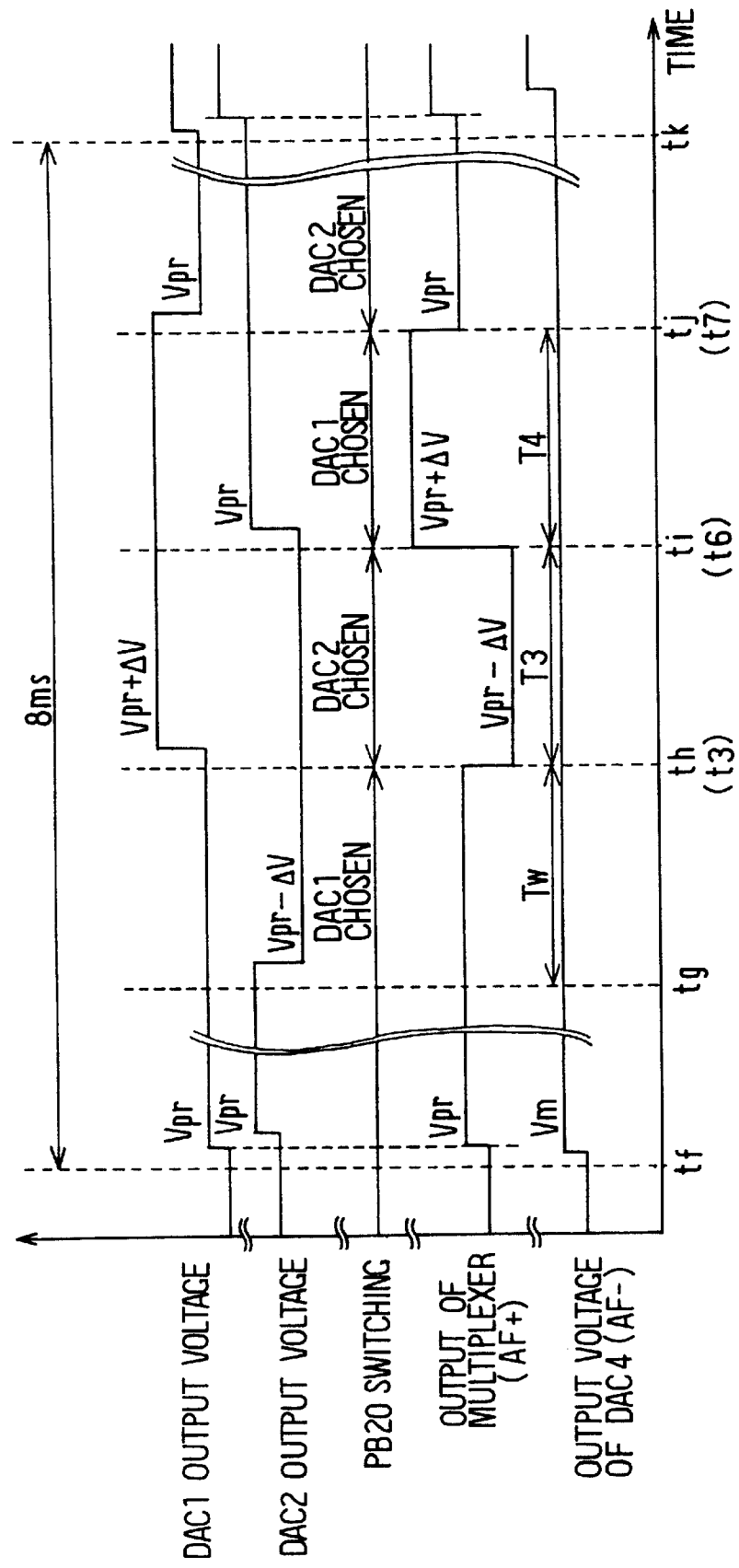
FIG. 17 is a time chart showing operations of the detection processing in FIG. 16 according to the fifth embodiment of the present invention.

Next an air-fuel-ratio detecting apparatus 61 implemented by a fifth embodiment is explained by referring to FIGS. 15 to 17.

FIG. 15 is a circuit diagram showing the configuration of the air-fuel-ratio detecting apparatus 61 implemented by the fifth embodiment.

As shown in FIG. 15, there are the following 2 differences between the configuration of the air-fuel-ratio detecting apparatus 61 implemented by the fifth embodiment and the configuration of the air-fuel-ratio detecting apparatus 51 implemented by the fourth embodiment shown in FIG. 10.

In the first place, in place of the multiplexer 8 employed in the fourth embodiment, the fifth embodiment employs a multiplexer 9 for selecting one of 2 inputs supplied to input terminals X1 and X2 in dependence on the level of a select signal supplied to a select terminal W0 and outputting the selected signal to an output terminal Y of the multiplexer 9.

To put it in detail, with the select signal supplied to the select terminal W0 set at the low level, the signal supplied to the input terminal X1 is selected and output to the output terminal Y. With the select signal supplied to the select terminal W0 set at the high level, on the other hand, it is the signal supplied to the input terminal X2 that is selected and output to the output terminal Y.

In the second place, the input terminals X1 and X2 of the multiplexer 9 are connected respectively to terminals DAC1 and DAC2 of a simple D/A converter embedded in the microcomputer 2 whereas the select terminal W0 of the multiplexer 9 is connected to the output terminal PB20 of the microprocessor 2. That is, the output terminals DAC3 and PB21 of the microcomputer 2 employed in the fourth embodiment are not used.

In addition, the microcomputer 2 employed in the air-fuel-ratio detecting apparatus 61 implemented by the fifth embodiment carries out detection processing shown in FIG. 16 in place of the detection processing shown in FIG. 11 to execute exactly the same functions as the air-fuel-ratio detecting apparatus 51 implemented by the fourth embodiment.

The detection processing carried out by the air-fuel-ratio detecting apparatus 61 implemented by the fifth embodiment is explained by referring to a flowchart shown in FIG. 16 as follows.

It should be noted that the detection processing shown in FIG. 16 is also executed at time intervals of 4 ms. In addition, in a normal operation not to detect an element admittance Y, the simple D/A converter embedded in the microcomputer 2 outputs voltages at exactly the same level as the plus-side reference voltage Vpr described earlier through the output terminal DAC1 or DAC2. Initially, the microcomputer 2 sets the signal output through the output terminal PB20 at the low level so that the multiplexer 9 selects and outputs the plus-side reference voltage Vpr generated through the output terminal DAC1 to the plus-side terminal AF+ of the air-ratio-terminal sensor AFS through the output terminal Y of the multiplexer 9.

As shown in FIG. 16, at steps S420 to S450 at the beginning of the flowchart, the microcomputer 2 carries out exactly the same processing of the steps S310 to S350 of the flowchart shown in FIG. 11.

At step S460, the signal output through the output terminal PB20 is set at the low level to drive the multiplexer 9 to select the voltage by the microcomputer 2 output through the output terminal DAC1. That is, the multiplexer 9 selects and outputs the voltage generated by the microcomputer 2 through the output terminal DAC1 to the plus-side terminal AF+ of the air-ratio-terminal sensor AFS through the output terminal Y of the multiplexer 9.

The flow of the detection processing then goes on step S470 at which the voltages output through the output terminals DAC1 and DAC2, that is, the plus-side reference voltage Vpr, are updated. Then, the flow continues to step S480 at which the voltage output through the output terminal DAC4, that is, the minus-side reference voltage Vm, is updated. It should be noted that the processing of the steps S470 and S480 is carried out in accordance with the same procedures as the processing of the steps S360 and S370 of the flowchart shown in FIG. 11.

On the other hand, a value of the counter CT determined at the step S440 to be 31 indicates that it is time to detect the element admittance Y. In this case, the flow of the detection processing goes on to step S490 at which the microcomputer 2 determines whether the magnitude of the sensor current I found at the step S430 is greater than a reference value determined in advance as the microcomputer 2 performs the processing at the step S380 of the flowchart shown in FIG. 11.

If the result of the determination of the step S490 is an affirmation, that is, if the magnitude of the sensor current I is determined at the step S490 to be greater than the reference value in the dynamic range, the flow of the detection processing proceeds to step S500 at which the microcomputer 2 changes the voltage output by the microprocessor 2 through the output terminal DAC2 to a voltage (Vpr−ΔV) lower than the plus-side reference voltage Vpr by the predetermined difference ΔV of 0.2 V where the plus-side reference voltage Vpr was updated at the step S470 at the immediately preceding execution of the detection processing. The flow of the detection processing then proceeds to step S520. That is, digital data contained in a second target register of the simple D/A converter is updated so that the voltage output through the output terminal DAC2 is lower than the plus-side reference voltage Vpr output through the output terminal DAC1 by the difference ΔV before the flow of the detection processing proceeds to the step S520.

If the result of the determination of the step S490 is a negation, that is, if the magnitude of the sensor current I is determined at the step S490 to be not greater than the reference value in the dynamic range, on the other hand, the flow of the detection processing proceeds to step S510 at which the microcomputer 2 changes the voltage output by the microprocessor 2 through the output terminal DAC2 to a voltage (Vpr+ΔV) higher than the plus-side reference voltage Vpr by the predetermined difference ΔV of 0.2 V where the plus-side reference voltage Vpr was updated at the step S470 at the immediately preceding execution of the detection processing. The flow of the detection processing then proceeds to the step S520. That is, digital data contained in the second target register of the simple D/A converter is updated so that the voltage output through the output terminal DAC2 is higher than the plus-side reference voltage Vpr output through the output terminal DAC1 by the difference ΔV before the flow of the detection processing proceeds to the step S520.

At the step S520, the microcomputer 2 determines whether a waiting time Tw longer than the maximum response delay time Tdmax of the simple D/A converter has elapsed since completion of the processing of the step S500 or S510. The waiting time Tw is set at 200 microseconds in the case of this embodiment. The microcomputer 2 repeats the processing of the step S530, waiting for the waiting time Tw to lapse. As the microcomputer 2 determines that the waiting time Tw has elapsed, the flow of the detection processing then goes on to step S530 at which the microcomputer 2 sets the signal output through the output terminal PB20 at a high level to drive the multiplexer 9 to select the voltage output through the output terminal DAC2. That is, the voltage (Vpr+ΔV) or (Vpr−ΔV) output through the output terminal DAC2 is applied to the plus-side terminal AF+ of the air-fuel-ratio sensor AFS through the output terminal Y of the multiplexer 9.

To be more specific, if the processing of the step S500 has been carried out due to an affirmative result of the determination of the step S490, a voltage Vo equal to (Vpr−ΔV) lower than the plus-side reference voltage Vpr by the predetermined difference ΔV of 0.2 V is applied to the plus-side terminal AF+ of the air-fuel-ratio sensor AFS at the step S530 as is the case with the transient change made at the point of time t3 of the timing charts shown in FIG. 12A. If the processing of the step S510 has been carried out due to a negation result of the determination of the step S490, on the other hand, a voltage Vo equal to (Vpr+ΔV) higher than the plus-side reference voltage Vpr by the predetermined difference ΔV of 0.2 V is applied to the plus-side terminal AF+ of the air-fuel-ratio sensor AFS at the step S530 as is the case with the transient change made at the point of time t3 of the timing charts shown in FIG. 12B.

The flow of the detection processing then goes on to step S540 at which the microcomputer 2 determines whether the magnitude of the sensor current I found at the step S430 is greater than the reference value as the microcomputer 2 performed the processing at the step S490.

If the result of the determination of the step S540 is an affirmation (YES), the flow of the detection processing proceeds to step S550 at which the microcomputer 2 changes the voltage output by the microprocessor 2 through the output terminal DAC1 to a voltage (Vpr+ΔV) higher than the plus-side reference voltage Vpr by the predetermined difference ΔV of 0.2 V where the plus-side reference voltage Vpr was updated at the step S470 at the immediately preceding execution of the detection processing. The flow of the detection processing then proceeds to step S570. That is, digital data contained in a first target register of the simple D/A converter is updated so that the voltage output through the output terminal DAC1 is higher than the plus-side reference voltage Vpr by the difference ΔV before the flow of the detection processing proceeds to the step S570.

If the result of the determination of the step S540 is a negation (NO), on the other hand, the flow of the detection processing proceeds to step S560 at which the microcomputer 2 changes the voltage output by the microprocessor 2 through the output terminal DAC1 to a voltage (Vpr−ΔV) lower than the plus-side reference voltage Vpr by the predetermined difference ΔV of 0.2 V where the plus-side reference voltage Vpr was updated at the step S470 at the immediately preceding execution of the detection processing. The flow of the detection processing then proceeds to the step S570. That is, digital data contained in the first target register of the simple D/A converter is updated so that the voltage output through the output terminal DAC1 is lower than the plus-side reference voltage Vpr by the difference ΔV before the flow of the detection processing proceeds to the step S570.

At the step S570, the microcomputer 2 determines whether a period of time T2 of typically 135 microseconds has elapsed since completion of the processing of the step S530. At the end of the period of time T2, the changeΔI in sensor current I is expected to reach a peak. The microcomputer 2 repeats the processing of the step S570, waiting for the period of time T2 to lapse. As the microcomputer 2 determines that the period of time T2 has elapsed, the processing of steps S580 to S600 which are the same as that of the steps S402 to S404 of the flowchart shown in FIG. 11 is carried out.

The flow of the detection processing then goes on to step S610 at which the microcomputer 2 determines whether a period of time T3 longer than the maximum response delay time Tdmax of the simple D/A converter has elapsed since completion of the processing of the step S530 and the step S550 or S560. The period of time T3 is set at a typical value of 200 microseconds. The microcomputer 2 repeats the processing of the step S610, waiting for the period of time T3 to lapse. As the microcomputer 2 determines that the period of time T3 has elapsed, the flow of the detection processing then goes on to step S620 at which the microcomputer 2 sets the signal output through the output terminal PB20 at the low level to drive the multiplexer 9 to select the voltage output through the output terminal DAC1. That is, the voltage (Vpr+ΔV) or (Vpr−ΔV) output through the output terminal DAC1 is applied to the plus-side terminal AF+ of the air-fuel-ratio sensor AFS through the output terminal Y of the multiplexer 9.

To be more specific, if the processing of the steps S500 and S550 has been carried out due to the affirmative results of the determinations of the steps S490 and S540 respectively, a voltage Vo equal to (Vpr+ΔV) higher than the plus-side reference voltage Vpr by the predetermined difference ΔV of 0.2 V is applied to the plus-side terminal AF+ of the air-fuel-ratio sensor AFS at the step S620 as is the case with the change made at the point of time t6 of the timing chart shown in FIG. 12A. If the processing of the steps S510 and S560 has been carried out due to the negation results of the determinations of the steps S490 and S540 respectively, on the other hand, a voltage Vo equal to (Vpr−ΔV) lower than the plus-side reference voltage Vpr by the predetermined difference ΔV of 0.2 V is applied to the plus-side terminal AF+ of the air-fuel-ratio sensor AFS at the step S620 as is the case with the change made at the point of time t6 of the timing charts shown in FIG. 12B.

The flow of the detection processing then proceeds to step S630 at which the voltage output through the output terminal DAC2 is returned to the plus-side reference voltage Vpr. That is, the contents of the second target register of the simple D/A converter are updated to generate a voltage equal to the plus-side reference voltage Vpr which was updated at the step S470 at the immediately preceding execution of the detection processing.

The flow of the detection processing then goes on to step S640 at which the microcomputer 2 determines whether a period of time T4 longer than the maximum response delay time Tdmax of the simple D/A converter has elapsed since completion of the processing of the steps S620 and S630. The period of time T4 is set at a typical value of 200 microseconds. The microcomputer 2 repeats the processing of the step S640, waiting for the period of time T4 to lapse. As the microcomputer 2 determines that the period of time T4 has elapsed, the flow of the detection processing then goes on to step S650 at which the microcomputer 2 sets the signal output through the output terminal PB20 at the high level to drive the multiplexer 9 to select the voltage output through the output terminal DAC2. That is, the plus-side reference voltage Vpr output through the output terminal DAC2 is applied to the plus-side terminal AF+ of the air-fuel-ratio sensor AFS through the output terminal Y of the multiplexer 9.

Thus, at the step S650, the voltage Vo applied to the plus-side terminal AF+ of the air-fuel-ratio sensor AFS is returned to the plus-side reference voltage Vpr output before the point of time t3 as is the case with the restoration carried out at the point of time t7 of the timing charts shown in FIGS. 12A and 12B.

Then, the flow of the detection processing continues to step S660 at which the counter CT is reset to 0. Finally, the flow proceeds to step S670 at which the voltage output through the output terminal DAC1 is returned to the plus-side reference voltage Vpr and the detection processing is ended. That is, the contents of the first target register of the simple D/A converter are updated to generate a voltage equal to the plus-side reference voltage Vpr which was updated at the step S470 at the immediately preceding execution of the detection processing before ending the detection processing.

Next, the detection processing represented by the flowchart shown in FIG. 16 is explained in terms of events occurring along the time axis by referring to timing charts shown in FIG. 17. It should be noted that FIG. 17 is timing charts for affirmative results of the determinations of the steps S490 and S540, that is, a case in which the voltage Vo applied to the plus-side terminal AF+ of the air-fuel-ratio sensor AFS is initially lowered and then raised before finally being returned to its original level as is the example shown in FIG. 12A.

First of all, when the contents of the counter CT have a value of 30, the processing of the steps S460 to S480 is carried out at a point of time tf of the timing charts shown in FIG. 17.

As a result, the voltages appearing at the output terminals DAC1, DAC2 and DAC4 of the microcomputer 2 change sequentially one after another within a period of time not longer than the maximum response delay time Tdmax introduced by the simple D/A converter as shown in FIG. 17. At that time, the plus-side reference voltage Vpr output by the microcomputer 2 through the output terminal DAC1 is selected by the multiplexer 9 and applied to the plus-side terminal AF+ of the air-fuel-ratio sensor AFS by way of the output terminal Y of the multiplexer 9. On the other hand, the minus-side reference voltage Vm output by the microcomputer 2 through the output terminal DAC4 is applied to the minus-side terminal AF− of the air-fuel-ratio sensor AFS.

Later on, at a point of time tg of the timing charts shown in FIG. 17, the detection processing represented by the flowchart shown in FIG. 16 is carried out again. This time, however, the value of the counter CT is found equal to 31 at the step S440. In this case, the processing of the step S500 or S510 is carried out. In this example, it is the processing of the step S500 that is carried out. As a result, the voltage output by the microprocessor 2 through the output terminal DAC2 changes within a period of time not longer than the maximum response delay time Tdmax introduced by the simple D/A converter to the voltage (Vpr−ΔV) which is lower than the plus-side reference voltage Vpr by the difference ΔV.

Then, at a point of time th of the timing chart shown in FIG. 17 corresponding to the point of time t3 of the timing charts shown in FIGS. 12A and 12B, that is, at a point of time after the waiting time Tw (>Tdmax, where Tdmax is the maximum response delay time introduced by the simple D/A converter) has elapsed since the point of time tg, the processing of the steps S530 and S550 or S560 of the flowchart shown in FIG. 16 is carried out. In this example, it is the processing of the step S550 that is carried out instead of S560. As a result, the voltage (Vpr−ΔV) appearing at the output terminal DAC2 of the microcomputer 2 is selected and generated through the output terminal Y of the multiplexer 9. Thus, the voltage Vo applied to the plus-side terminal AF+ of the air-fuel-ratio sensor AFS changes from the plus-side reference voltage Vpr to the voltage (Vpr−ΔV). Right after that, the voltage output by the microprocessor 2 through the output terminal DAC1 also changes within a period of time not longer than the maximum response delay time Tdmax of the simple D/A converter to the voltage (Vpr+ΔV) which is higher than the plus-side reference voltage Vpr by the difference ΔV.

Then, at a point of time ti of the timing charts shown in FIG. 17 corresponding to the point of time t6 of the timing charts shown in FIGS. 12A and 12B, that is, at a point of time after the predetermined period of time T3 (>Tdmax, where Tdmax is the maximum response delay time introduced by the simple D/A converter) has elapsed since the point of time th, the processing of the steps S620 and S630 of the flowchart shown in FIG. 16 is carried out. As a result, the voltage (Vpr+ΔV) appearing at the output terminal DAC1 of the microcomputer 2 is selected and generated through the output terminal Y of the multiplexer 9. Thus, the voltage Vo applied to the plus-side terminal AF+ of the air-fuel-ratio sensor AFS swings to the voltage (Vpr+ΔV). Right after that, the voltage output by the microprocessor 2 through the output terminal DAC2 is also returned to the plus-side reference voltage Vpr within a period of time not longer than the maximum response delay time Tdmax.

Then, at a point of time tj of the timing charts shown in FIG. 17 corresponding to the point of time t7 of the timing charts shown in FIGS. 12A and 12B, that is, at a point of time after the predetermined period of time T4 (>Tdmax, where Tdmax is the maximum response delay time introduced by the simple D/A converter) has elapsed since the point of time ti, the processing of the steps S650 to S670 of the flowchart shown in FIG. 16 is carried out. As a result, the plus-side reference voltage Vpr appearing at the output terminal DAC2 of the microcomputer 2 is selected and generated through the output terminal Y of the multiplexer 9. Thus, the voltage Vo applied to the plus-side terminal AF+ of the air-fuel-ratio sensor AFS is returned to the plus-side reference voltage Vpr. Right after that, the voltage output by the microprocessor 2 through the output terminal DAC1 is also returned to the plus-side reference voltage Vpr within a period of time not longer than the maximum response delay time Tdmax.

Then, at a point of time tk of the timing charts shown in FIG. 17, the detection processing represented by the flowchart shown in FIG. 16 is carried out again. This time, however, the value of the counter CT is found equal to 0 at the step S440. Since the result of the determination of the step S440 is a negation (NO), the processing of the steps S460 to S480 is carried out again. Much like the processing carried out at the point of time tf, the voltages appearing at the output terminals DAC1, DAC2 and DAC4 of the microcomputer 2 thus change sequentially one after another within a period of time not longer than the maximum response delay time Tdmax introduced by the simple D/A converter.

Thereafter, the detection processing represented by the flowchart shown in FIG. 16 is repeated to carry out the same processing performed at the point of time tf till the contents of the counter CT are found equal to 31 at the step S440 to indicate that it is time to detect the element admittance Y.

In should be noted that, in the fifth embodiment, the processing of the steps S440 to S560 and the steps S610 to S670 of the flowchart shown in FIG. 16 are carried out as an applied-voltage changing means. The processing of the steps S530 to S560 of the applied-voltage changing means is carried out as a first step of the processing whereas the processing of the steps S610 to S630 of the applied-voltage changing means is carried out as a second step of the processing. The processing of the steps S640 and S650 of the applied-voltage changing means is carried out as a third step of the processing.

As described in detail above, according to the fifth embodiment, the voltages generated by the simple D/A converter through the output terminals DAC1 and DAC2 are switched from one to another, being applied to the plus-side terminal AF+ of the air-fuel-ratio sensor AFS alternately. That is, in each switching operation, the simple D/A converter is driven to output a voltage to be applied to the plus-side terminal AF+ of the air-fuel-ratio sensor AFS in the next switching operation to an output terminal which is not currently selected by the multiplexer 9.

As a result, the air-fuel-ratio detecting apparatus 61 implemented by the fifth embodiment results in exactly the same effects as the air-fuel-ratio detecting apparatus 51 implemented by the fourth embodiment in spite of the fact that the number of output terminals of the simple D/A converter and, hence, the number of input terminals of the multiplexer 9 are each reduced by 1. For this reason, the size of the circuit configuration can be minimized and the cost can be reduced.

In the air-fuel-ratio detecting apparatus 61 implemented by the fifth embodiment and the air-fuel-ratio detecting apparatus 51 implemented by the fourth embodiment, the voltage generated through the output terminal DAC4 of the microcomputer 2 is applied to the minus-side terminal AF− of the air-fuel-ratio sensor AFS. If it is not necessary to change the minus-side reference voltage Vm applied to the minus-side terminal AF− of the air-fuel-ratio sensor AFS, a constant voltage generated by typically a voltage divider can be supplied in place of the voltage generated through the output terminal DAC4 of the microcomputer 2 to the non-inverting input terminal of the operational amplifier OP6. As another alternative, the minus-side terminal AF− of the air-fuel-ratio sensor AFS can also be wired to a fixed electric potential such as the ground potential GND from the beginning.

In the air-fuel-ratio detecting apparatus 51 implemented by the fourth embodiment, on the other hand, the simple D/A converter embedded in the microcomputer 2 outputs 3 voltage with levels different from each other to the multiplexer 8 through the output terminals DAC1 to DAC3 in order to raise and lower the voltage applied to the plus-side terminal AF+ of the air-fuel-ratio sensor AFS. As an alternative, if it is desired to merely either raise and lower the voltage applied to the plus-side terminal AF+ of the air-fuel-ratio sensor AFS, the output terminal DAC1 or DAC3 can be eliminated.

If it is not necessary to change the plus-side reference voltage Vpr used as a reference for the voltage applied to the plus-side terminal AF+ of the air-fuel-ratio sensor AFS, the input terminals X1 to X3 of the multiplexer 8 employed in the air-fuel-ratio detecting apparatus 51 implemented by the fourth embodiment can be connected to typically a voltage divider comprising resistors for generating the 3 voltages with levels different from each other instead of the output terminals DAC1 to DAC3 of the microcomputer 2.

As described above, in the first to fifth embodiments, an admittance computing means is used as a resistance-component calculating means provided by the present invention. It should be noted, however, that an impedance computing means can also be used in place of the admittance computing means.

(Sixth Embodiment)

Figure 18:
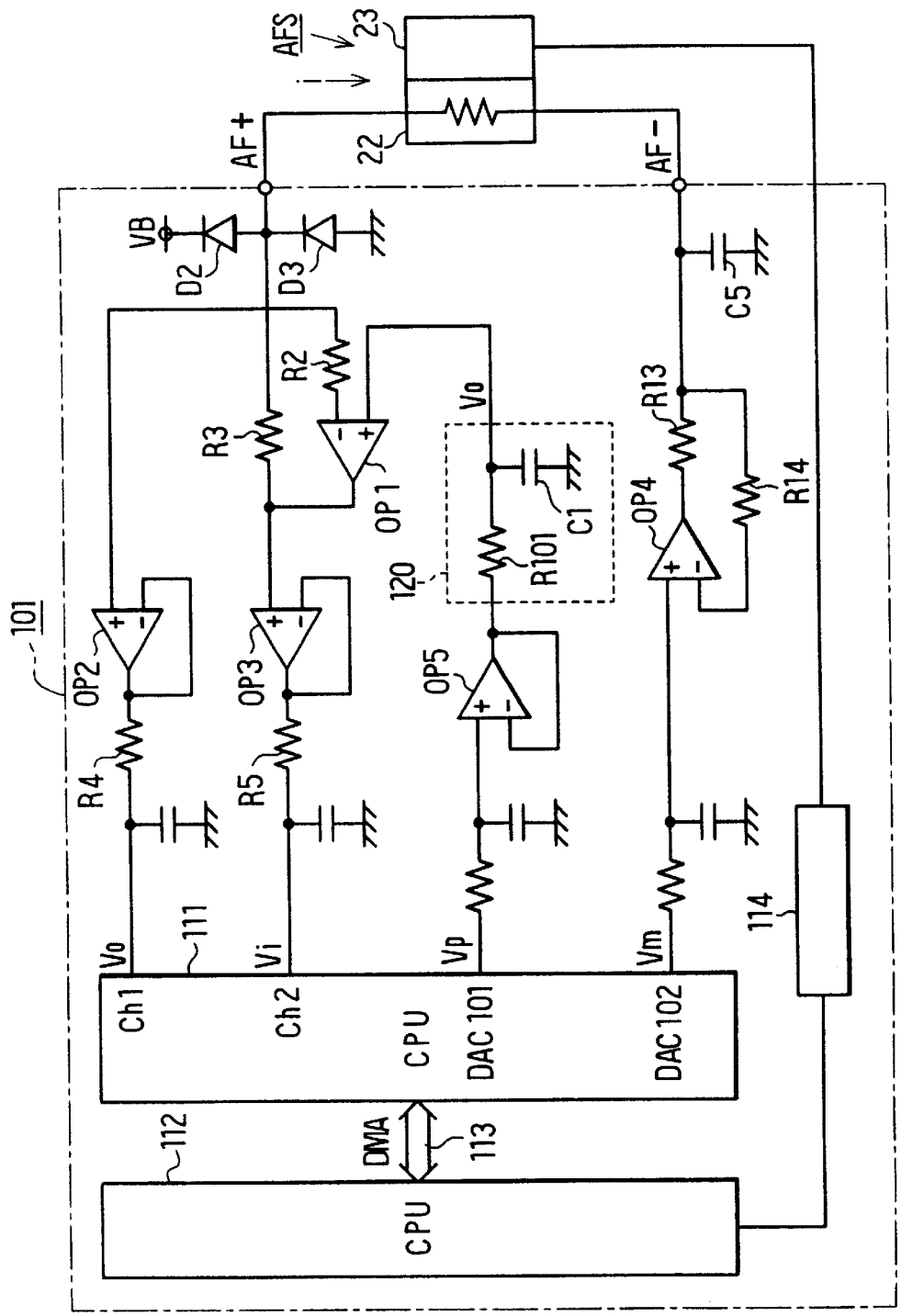
FIG. 18 is a circuit diagram illustrating an electrical configuration of an on-board ECU according to a sixth embodiment of the present invention.
Figure 24:
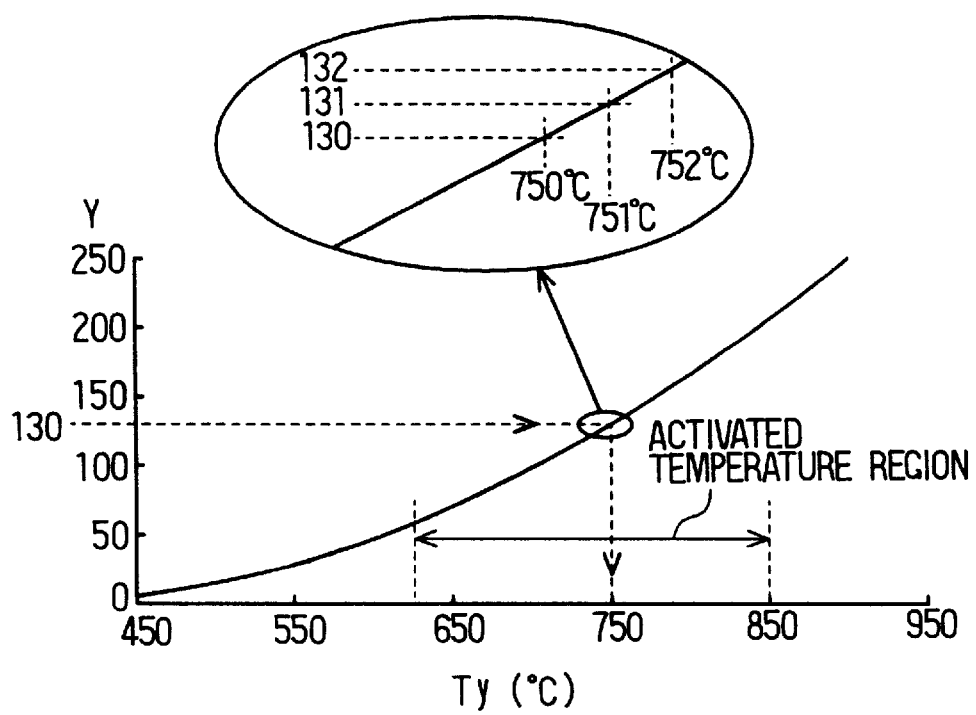
FIG. 24 is a graph showing a relationship between element temperature and admittance count value according to the sixth embodiment of the present invention.

Next, a sixth embodiment of the present invention is explained by referring to FIGS. 18 and 24. The sixth embodiment implements the present invention as an air-fuel-ratio detecting apparatus applied to an air-fuel-ratio control system employed in an engine of a vehicle. An electronic control unit mounted on a vehicle which is also referred to hereafter simply as an on-board ECU executes air-fuel-ratio feedback (F/B) control based on results of detection output by an air-fuel-ratio sensor (A/F sensor) of the limit-current type provided on an exhaust pipe of the engine. The ECU also controls the heating of the A/F sensor by a heater for maintaining an activation state of the sensor by monitoring the element temperature of the sensor. Details of the sixth embodiment are explained as follows.

The voltage-current characteristic of the sensor-element unit 22 is shown in FIG. 3. As described earlier, a voltage region lower than the straight-line segments parallel to the V axis of the voltage-current characteristic is called a resistance-dominant region. The gradient of a linear slanting straight line in the resistance-dominant region represents the internal resistance or the element resistance of the solid electrolyte layer 24 of the sensor-element unit 22. The element resistance varies with the element temperature. To be more specific, when the temperature of the sensor-element unit 22 decreases, the element resistance increases or the gradient of the slanting straight line decreases.

The first central processing unit (hereinafter referred to as "CPU") 111 employed in the ECU 101 has two terminals Ch101 and 102 serving as input terminals of an A/D converter embedded in the first CPU 111 as well as two terminals DAC101 and DAC102 serving as output terminals of a D/A converter embedded therein.

The configuration of an air-fuel-ratio detecting circuit employed in the on-board ECU 101 includes the following main components:

an operational amplifier OP1 with an inverting input terminal thereof connected by a resistor R2 to the plus-side terminal AF+ of the air-fuel-ratio sensor AFS, that is, a terminal connected to the atmosphere-side electrode layer 27 shown in FIG. 2;

a shunt resistor R3 connected between the plus-side terminal AF+ of the air-fuel-ratio sensor AFS and an output terminal of the operational amplifier OP1;

an operational amplifier OP2 with a non-inverting input terminal thereof connected to the plus-side terminal AF+ of the air-fuel-ratio sensor AFS and an inverting input terminal thereof wired directly to an output terminal thereof; and an operational amplifier OP3 with a non-inverting input terminal thereof connected to the output terminal of the operational amplifier OP1 and an inverting input terminal thereof wired directly to an output terminal thereof.

It should be noted that the shunt resistor R3 has a resistance of about 100 ohms. The output terminals of the operational amplifiers OP2 and OP3 are connected to the input terminals Ch101 and Ch102 respectively by resistors R4 and R5 respectively. A non-inverting input terminal of the operational amplifier OP1 is connected to an output terminal of a low-pass filter (LPF) 120 which comprises a resistor R101 and a capacitor C1.

In addition, the configuration of an air-fuel-ratio detecting circuit employed in the on-board ECU 101 further includes the following components:

an operational amplifier OP5 with a non-inverting input terminal thereof connected to the output terminal DAC101 of the first CPU 111 and an inverting input terminal thereof wired directly to an output terminal thereof; and an operational amplifier OP4 with a non-inverting input terminal thereof connected to the output terminal DAC102 of the first CPU 111 and an inverting input terminal and an output terminal thereof connected by resistors R14 and R13 respectively to the minus-side terminal AF− of the air-fuel-ratio sensor AFS, that is, a terminal connected to the exhausted-gas-side electrode layer 26 shown in FIG. 2.

Furthermore, the air-fuel-ratio detecting circuit also includes a capacitor C5 as well as diodes D2 and D3. The capacitor C5 is connected between a signal line from the resistor R13 to the minus-side terminal AF− of the air-fuel-ratio sensor AFS and the ground potential GND. An anode of the diode D2 is connected to a signal line from the shunt resistor R3 to the plus-side terminal AF+ of the air-fuel-ratio sensor AFS. A cathode of the diode D2 is connected to a battery voltage VB. On the other hand, a cathode of the diode D3 is connected to the signal line from the shunt resistor R3 to the plus-side terminal AF+ of the air-fuel-ratio sensor AFS. An anode of the diode D3 is connected to the ground potential. It should be noted that the capacitor C5 is used for preventing a high-voltage surge or high-voltage static electricity from being introduced from the signal line between the air-fuel-ratio detecting circuit and the minus-side terminal AF− of the air-fuel-ratio sensor AFS into the air-fuel-ratio detecting circuit. By the same token, the two diodes D2 and D3 are used for preventing a high-voltage surge or high-voltage static electricity from being introduced from the signal line between the air-fuel-ratio detecting circuit and the plus-side terminal AF+ of the air-fuel-ratio sensor AFS into the air-fuel-ratio detecting circuit. Components such as capacitors used for mainly eliminating noise are also employed appropriately in the air-fuel-ratio detecting circuit.

In the ECU 101 with a configuration described above, a voltage Vp output by the first CPU 111 through the output terminal DAC101 is supplied as a voltage Vo through the operational amplifier OP5 and the LPF 120 to an output circuit comprising the operational amplifier OP1, the resistor R2 and the shunt resistor R3. The output circuit passes on this voltage Vo to the plus-side terminal AF+ of the air-fuel-ratio sensor AFS. That is, the operational amplifier OP1 adjusts a voltage output thereby so that the voltage applied to the plus-side terminal AF+ of the air-fuel-ratio sensor AFS becomes equal to the voltage Vo output by the low-pass filter 120.

On the other hand, the first CPU 111 outputs a minus-side reference voltage Vm to the minus-side terminal AF− of the air-fuel-ratio sensor AFS through the output terminal DAC102 and another output circuit comprising the operational amplifier OP4, the resistor R13 and the resistor R14. In this embodiment, the minus-side reference voltage Vm is 3.0 V.

The so-called oxygen-concentration-detection voltage, that is, the difference between the voltages Vp and Vm generated by the first CPU 111 at the output terminals DAC101 and DAC102 respectively, is applied between the plus-side terminal AF+ and the minus-side terminal AF− of the air-fuel-ratio sensor AFS as a voltage for detection of the air-fuel ratio of mixed air. Typically, the voltages Vp and Vm are 3.3 V and 3.0 V respectively. Thus, an oxygen-concentration-detection voltage of 0.3 V is applied across the air-fuel-ratio sensor AFS, causing a limit current I representing the concentration of oxygen contained in exhausted gas at that time to flow through the air-fuel-ratio sensor AFS.

Also referred to hereafter as a sensor current, the limit current I flowing through the air-fuel-ratio sensor AFS also flows through the shunt resistor R3. Thus, an electric-potential difference proportional to the sensor current I appears between the ends of the shunt resistor R3. This electric-potential difference is supplied to the first CPU 111 as follows. The voltage Vo appearing at the end of the shunt resistor R3 connected to the plus-side terminal AF+ of the air-fuel-ratio sensor AFS, that is, the voltage applied to the plus-side terminal AF+ of the air-fuel-ratio sensor AFS, is supplied to the input terminal Ch1 of the first CPU 111 through the operational amplifier OP2. On the other hand, a voltage Vi having the same potential level as a voltage appearing at the other end of the shunt resistor R3, that is, a voltage output by the operational amplifier OP1, is supplied to the input terminal Ch2 of the first CPU 111 through the operational amplifier OP3.

The A/D converter embedded in the first CPU 111 of the air-fuel-ratio detecting circuit provided by this embodiment converts the voltages Vo and Vi through the input terminals Ch1 and Ch2 respectively as described above into digital data, dividing the electric-potential difference (Vi−Vo) by the resistance of the shunt resistor R3 in order to detect the sensor current I flowing through the air-fuel-ratio sensor AFS. From the magnitude of the sensor current I, the air-fuel ratio of mixed air, that is, the concentration of oxygen contained in exhausted gas, is found at time intervals of typically 4 ms.

Figure 23A:
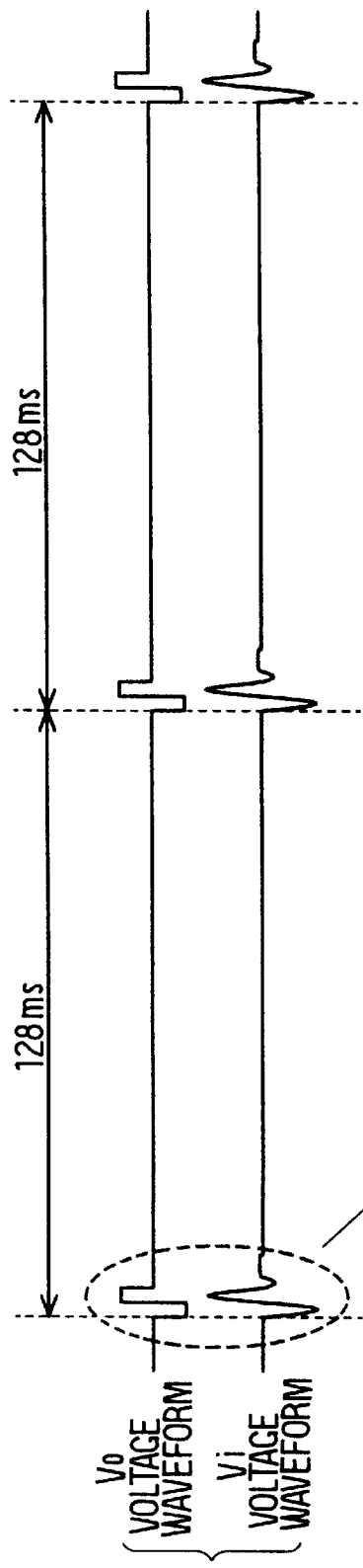
FIG. 23A is a time chart showing waveforms of voltages Vo and Vi when the element temperature is detected according to the sixth embodiment of the present invention.
Figure 23B:
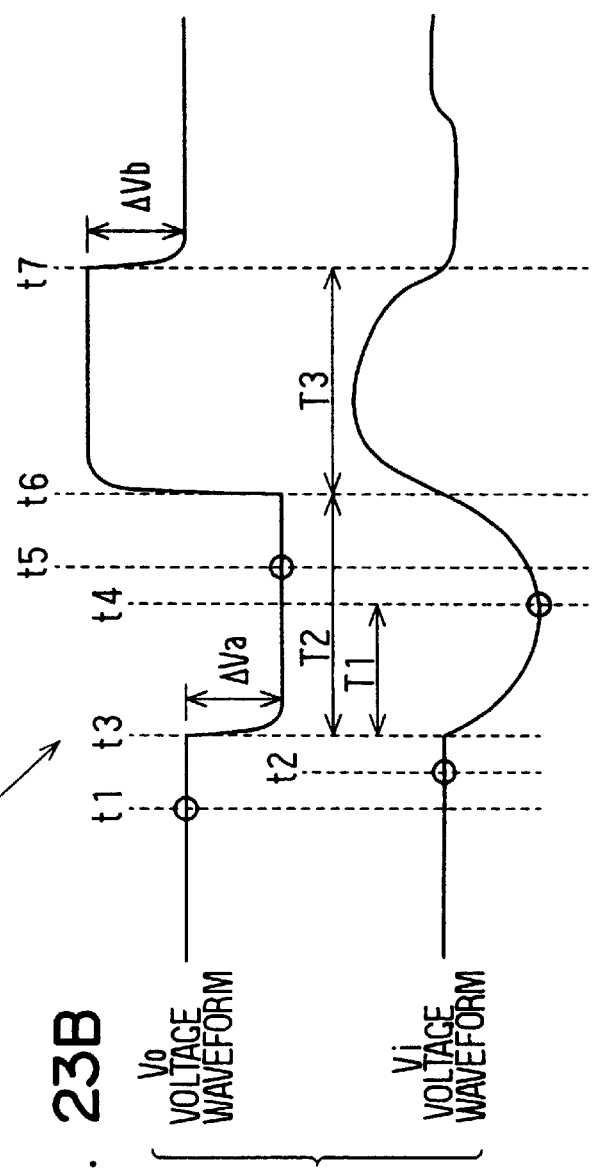
FIG. 23B is a time chart showing an enlarged waveforms of a portion of FIG. 23A encircled by a dotted eclipse.

By the way, the first CPU 111 changes the oxygen-concentration-detection voltage applied across the air-fuel-ratio sensor AFS for detecting the air-fuel ratio at predetermined time intervals of typically 128 ms as shown in FIG. 23A in order to detect the element resistance Y of the air-fuel-ratio sensor AFS. In this embodiment, the voltage Vp appearing at the output terminal DAC 101 is changed to exhibit a rectangular waveform in a transient state. In FIG. 23A, the transient change in voltage Vp is shown as a transient change in Vo waveform which is supplied to the input terminal Ch1. It should be noted that the voltage Vo exhibits a waveform distorted by a time constant obtained as a result of passing the voltage Vp through the low-pass filter 120. FIG. 23B shows detailed waveforms of a portion of FIG. 23A enclosed in an ellipse.

To put it concretely, the first CPU 111 detects the element resistance of the air-fuel-ratio sensor AFS according to the following procedure.

First of all, at a point of time t1 of the timing charts shown in FIG. 23B, the voltage Vo received through the input terminal Ch1 is detected. Let notation Vo(t1) denote the voltage Vo detected at the point of time t1.

Then, at a point of time t2 right after the point of time t1, the voltage Vi received through the input terminal Ch2 is detected. Let notation Vi(t2) denote the voltage Vi detected at the point of time t2.

Subsequently, at a point of time t3 right after the point of time t2, the voltage Vp output to the output terminal DAC101 is changed to a level lower than a steady-state voltage for detecting the air-fuel ratio by ΔVa.

Then, at a point of time t4 lagging behind the point of time t3 by a predetermined period of time T1, the voltage Vi received through the input terminal Ch2 is detected. Let notation Vi (t4) denote the voltage Vi detected at the point of time t4. The period of time T1 is set at such a value that, at the end of the period of time T1, that is, at the point of time t4, a transient change ΔI in sensor current I which starts at the point of time t3 is expected to reach a peak.

Subsequently, at a point of time t5 right after the point of time t4, the voltage Vo received through the input terminal Ch1 is detected. Let notation Vo(t5) denote the voltage Vo detected at the point of time t5. The element admittance Y, the reciprocal of the element resistance, is computed by using equation (2) as follows:

$$Y = \frac{\Delta I}{\Delta V} \qquad (2)$$
$$= \frac{\{Vi(t2) - Vo(t1)\} - \{Vi(t4) - Vo(t5)\}}{\{Vo(t1) - Vo(t5) \times Rs\}}$$
$$= \frac{\{Vi(t2) - Vi(t4)\} - \{Vo(t1) - Vo(t5)\}}{\{Vo(t1) - Vo(t5) \times Rs\}}$$

where the symbol RS is the resistance of the shunt resistor R3, expression {Vo(t1)–Vo(t5)} of the denominator is a transient change ΔV in voltage Vo applied to the plus-side terminal AF+ and the remaining expression on the right-hand side of Eq. (2) is the transient change ΔI in sensor current I. The change ΔV in voltage Vo is equal to the aforementioned change ΔVa in voltage Vp which is set by the first CPU 111 and, hence, a known value. {Vo(t1)–Vo (t5)} of the equation (2) corresponds to the changing amount ΔV of the applied voltage. {Vo(t1)-Vo(t5)} can be replaced by known ΔVa.

Then, at a point of time t6 lagging behind the point of time t3 by a predetermined period of time T2, the voltage Vp output to the output terminal DAC101 is changed to a level higher than the steady-state voltage for detecting the air-fuel ratio by ΔVb.

Subsequently, at a point of time t7 lagging behind the point of time t6 by a predetermined period of time T3, the voltage the voltage Vp output to the output terminal DAC101 is returned to the steady-state voltage for detecting the air-fuel ratio.

It should be noted that the reason why the voltage Vp output to the output terminal DAC101 is changed to a level higher than the steady-state voltage for detecting the air-fuel ratio by ΔVb at the point of time t6 after the detection of the element admittance Y, that is, the reciprocal of the element resistance or, in general, the reason why the voltage Vp output to the output terminal DAC101 is changed at the point of time t6 in a direction opposite to the direction of the change made at the point of time t3 is to expedite the settling or the stabilization of the sensor current I to its steady-state magnitude. That is, if the voltage Vp is returned directly to the original steady-state voltage level without first changing it in the opposite direction, it will take a longer time to stabilize the sensor current I to its steady-state magnitude due to the fact that the peak sensor current I reaches a peak right after the restoration of the voltage Vp in a process of discharging electric charge from capacitance components of the air-fuel-ratio sensor AFS. In order to solve this problem, in this embodiment, before the voltage Vp is returned to the original steady-state voltage level, it is first changed in a direction opposite to the first change for a short period of time. It is thus possible to shorten the time it takes to discharge electric charge from capacitance components of the element of the air-fuel-ratio sensor AFS and to stabilize the sensor current I to its steady-state magnitude. If the waveforms of the changes in voltage Vp are set so that the amount of electric charge migrating in the element of the air-fuel-ratio sensor AFS due to a change in voltage Vp in one direction can be made equal to the amount of electric charge migrating in the element of the air-fuel-ratio sensor AFS due to a change in voltage Vp in the opposite direction, the time it takes to stabilize the sensor current I to its steady-state magnitude can be shortened more effectively.

Figure 19:
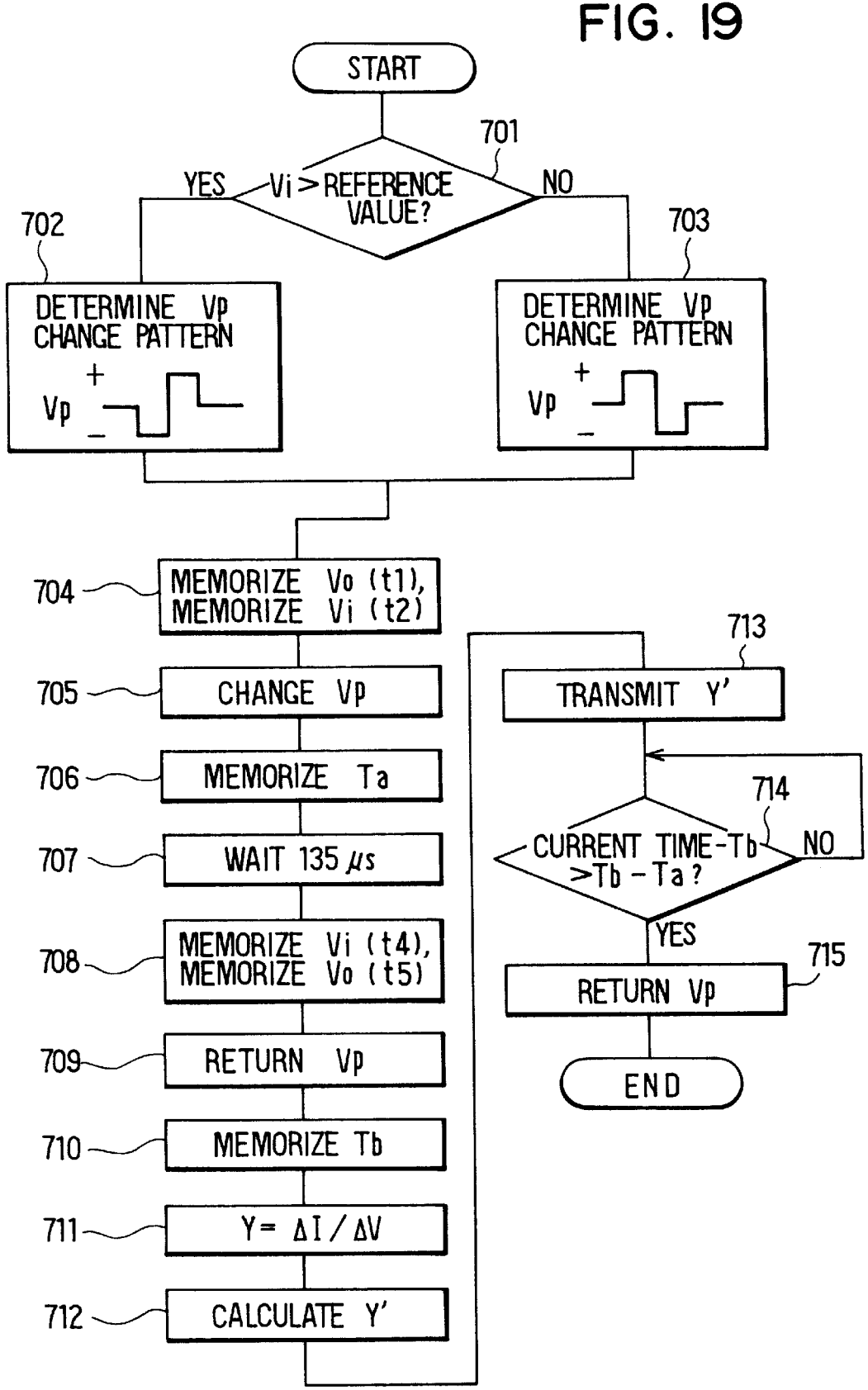
FIG. 19 is a flowchart showing a detection routine for an element resistance detection according to the sixth embodiment of the present invention.

Next, an element-resistance detection routine executed by the first CPU 111 to detect the element admittance Y of the air-fuel-ratio sensor AFS is explained by referring to a flowchart shown in FIG. 19. The routine shown in FIG. 19 is executed at time intervals of typically 128 ms.

As shown in the figure, the flowchart of FIG. 19 representing processing to detect the element resistance starts with step S701 at which the first CPU 111 detects the voltage Vi received through the input terminal Ch2 and compares the voltage Vi with a predetermined reference value in order to determine whether the voltage Vi is higher than the reference value. The predetermined reference value is the center of a range of voltages that the operational amplifier OP1 is capable of outputting. In this embodiment, since the operational amplifier OP1 generates a voltage in the range 1.5 V to 4.5 V, the reference value is predetermined at 3.0 V.

If the voltage Vi is found higher than the reference value, the CPU 111 continues the processing with step S702 to adopt voltage changing processing wherein the applied voltage Vp is first changed to a level lower than the steady-state voltage, that is, the voltage for detection of the air-fuel ratio, and then to a level higher than the steady-state voltage. If the voltage Vi is found not higher than the reference value, on the other hand, the CPU 111 continues the processing with step S703 to adopt voltage changing processing wherein the applied voltage Vp is first changed to a level higher than the steady-state voltage, that is, the voltage for detection of the air-fuel ratio, and then to a level lower than the steady-state voltage.

Assume that Vi=2.0 V. In this case, the result of the determination of step S701 is NO. If the applied voltage Vp is lowered, the voltage Vo will be saturated right away at the lower limit of 1.5 V of the output-voltage range of the operational amplifier OP1. As a result, the difference between the voltages Vi and Vo that is resulted in after the voltages change do not correctly represent the sensor current I any more, making it impossible to detect the element resistance with a high degree of accuracy. On the contrary, assume that Vi=4.0 V. In this case, the result of the determination of step S701 is YES. If the applied voltage Vp is raised, the voltage Vo will be saturated right away at the upper limit of 4.5 V of the output-voltage range of the operational amplifier OP1. As a result, the difference between the voltages Vi and Vo that is resulted in after the voltages change do not correctly represent the sensor current I any more, making it impossible to detect the element resistance with a high degree of accuracy. In order to solve this problem, the direction of the change in voltage Vp is determined. In this way, it is possible to prevent the voltage Vi from getting saturated at the lower or upper limit of the output-voltage range of the operational amplifier OP1.

The flow of the processing then proceeds to step S704 at which the first CPU 111 detects the voltage Vo received through the input terminal Ch1, storing the detected voltage Vo as Vo(t1) cited earlier and detects the voltage Vi received through the input terminal Ch2, storing the detected voltage Vi as Vi(t2) cited earlier.

Then, the flow of the processing continues to step S705 at which the voltage Vp output through the output terminal DAC101 is lowered or raised in accordance with the decision made at the step S702 or S703 respectively. To be more specific, if the result of the determination of the step S701 is an affirmation, the voltage Vp output through the output terminal DAC101 is lowered. If the result of the determination of the step S701 is a negation, on the other hand, the voltage Vp output through the output terminal DAC101 is raised. Subsequently, the flow of the processing goes on to step S706 at which the present point of time is stored as Ta corresponding to the point of time t3 of the timing charts shown in FIG. 23B.

Subsequently, the flow of the processing goes on to step S707 to enter a wait state for a predetermined period of time. This period of time corresponds to the period of time T1 of the timing charts shown in FIG. 23B. In this embodiment, this period of time is 135 microseconds long.

After the period of 135 microseconds has elapsed, the flow of the processing proceeds to step S708 at which the first the voltage Vi received through the input terminal Ch2 is detected and stored as Vi (t4) cited earlier whereas the voltage Vo received through the input terminal Ch1 is detected and stored as Vo(t5) cited earlier.

The flow of the processing then continues to step S709 at which the voltage Vp is changed in a direction opposite to the direction of the change made at the step S705. To be more specific, if the result of the determination of the step S701 is an affirmation, the voltage Vp output through the output terminal DAC101 is raised. If the result of the determination of the step S701 is a negation, on the other hand, the voltage Vp output through the output terminal DAC101 is lowered. Subsequently, the flow of the processing goes on to step S710 at which the first CPU 111 stores the present point of time as Tb corresponding to the point of time t6 of the timing charts shown in FIG. 23B.

Then, the flow of the processing goes on to step S711 at which the first CPU 111 computes the element admittance Y from a change $\Delta V$ in voltage vo and a change $\Delta I$ in sensor current I by using Eq. (3) as follows:

$$Y = \frac{\Delta I}{\Delta V} \qquad (3)$$

$$= \frac{\{Vi(t2) - Vo(t1)\} - \{Vi(t4) - Vo(t5)\}}{Vo(t1) - Vo(t5)}$$

Basically, Eq. (3) is the same as Eq. (2) described earlier except that the resistance RS of the shunt resistor R3 is omitted from Eq. (3). This is because LSB conversion to be carried out at a later step S712 will compensate the result of computation for the omission of resistance RS anyway.

The flow of the processing then goes on to the step S712 at which the element admittance Y computed at the step S711 is subjected to LSB conversion to find an admittance count value Y'. Then, the flow of the processing then goes on to step S713 at which the admittance count value Y' is transferred to the second CPU 112. At the steps S704 to S711, 2 byte-data is processed. At the step S713, on the other hand, one-byte data completing the LSB conversion is transferred by direct memory access transmission (hereinafter referred to as "DMA transmission").

Subsequently, the flow of the processing goes on to step S714 at which the first CPU 111 compares the difference between the present time and the point of time Tb with the difference between the points of time Tb and Ta (Tb−Ta) to determine whether the following relation holds true:

(Present time−Tb)>(Tb−Ta)

The processing of the step S714 is repeated till the above relation is satisfied. As the above relation holds true, the flow of the processing proceeds to step S715 at which the first CPU 111 restores the voltage Vp output through the output terminal DAC 101 to the original steady-state level, that is, the voltage for detecting the air-fuel ratio, and ends the admittance-detection processing. In the timing charts shown in FIG. 23B, the result of the determination of the step S714 turns into an affirmation at a point of time t7.

Figure 20:
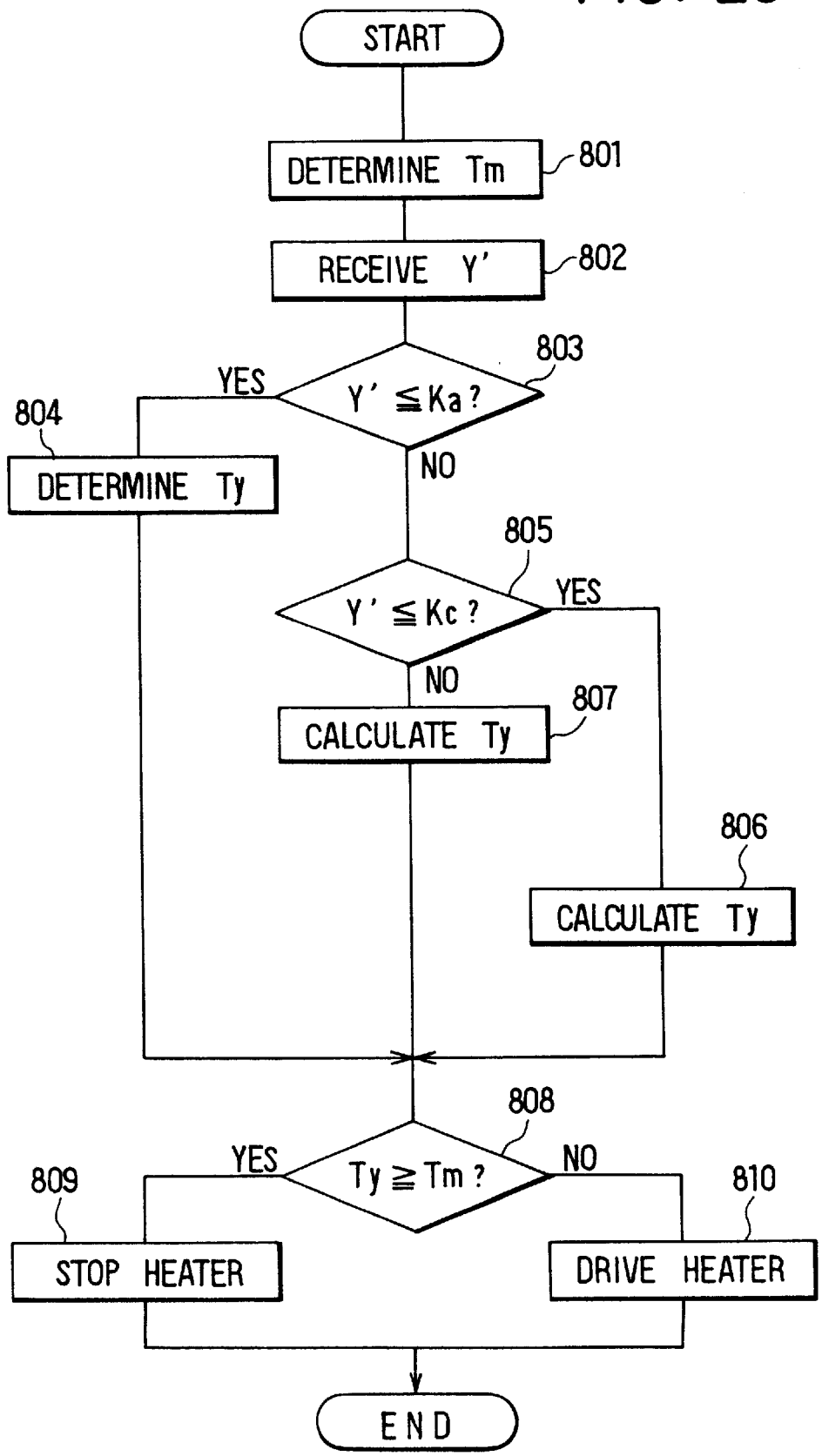
FIG. 20 is a flowchart showing a heater driving routine according to the sixth embodiment of the present invention.

Next, a heater driving routine executed by the second CPU 112 is explained by referring to a flowchart shown in FIG. 20. It should be noted that processing represented by the flowchart shown in FIG. 20 is carried out also at time intervals of typically 128 ms.

As shown in FIG. 20, the flowchart begins with step S801 at which the second CPU 112 sets a target temperature Tm. In this embodiment, the target temperature Tm is set at a typical value of 700 degrees C. The flow of the processing then goes on to step S802 at which the second CPU 112 receives an admittance count value Y' from the first CPU 111.

Then, the flow of the processing goes on to step S803 at which the second CPU 112 determines whether the admittance count value Y' received from the first CPU 111 is equal to or smaller than a predetermined value Ka which is a threshold value used as a criterion as to whether the air-fuel-ratio sensor AFS in an activated or inactivated state. Typically, the threshold is a count value corresponding to a typical element temperature of 625 degrees Celsius.

Figures 21, 22:
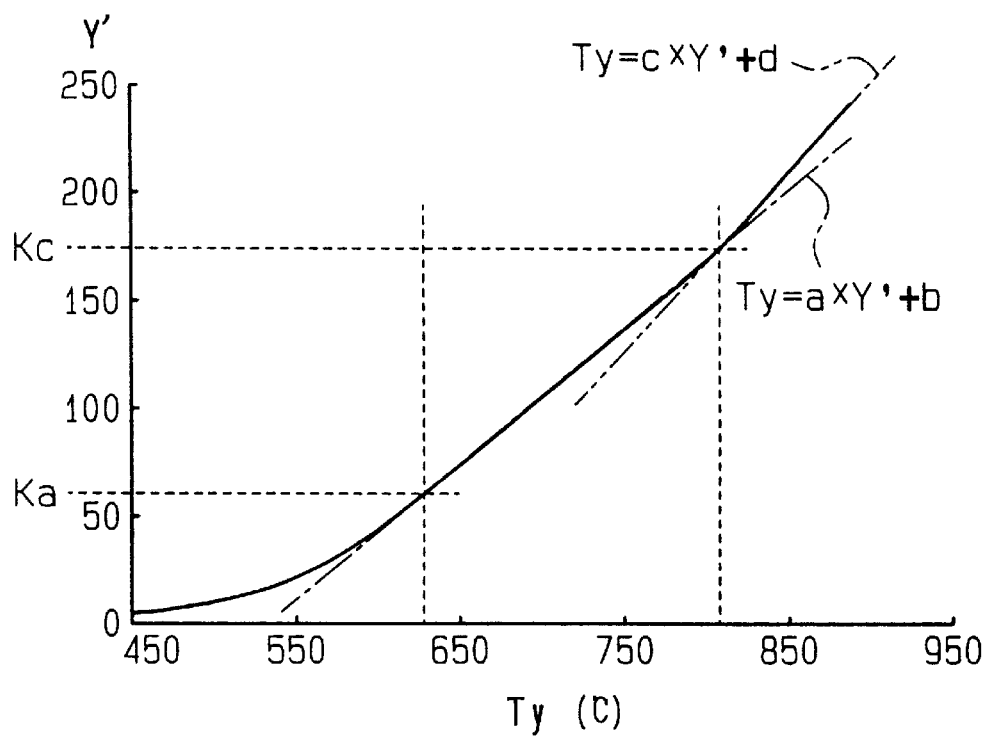
FIG. 21 is a graph showing a relationship between element temperature and admittance count value according to the sixth embodiment of the present invention.
FIG. 22 shows a map used for determining element temperature according to the sixth embodiment of the present invention.

If the admittance count value Y' is found equal to or smaller than the threshold Ka at the step S203, that is, if the result of the determination of the step S803 is YES, the flow of the processing proceeds to step S804 at which the second CPU 112 converts the admittance count value Y' into an element temperature Ty by interpolation based on a conversion map shown in FIG. 22. An admittance count value Y' equal to or smaller than Ka for example indicates a case in which the engine has just been started and is in a process of warming-up. Since the air-fuel-ratio sensor AFS is in an inactivated state, the element temperature Ty is found from the conversion map shown in FIG. 22.

If the admittance count value Y' is found greater than the threshold Ka at the step S803, that is, if the result of the determination of the step S803 is NO, on the other hand, the flow of the processing proceeds to steps S805 to S807 at which the element temperature Ty is computed by linear approximation represented by 2 straight lines each representing a linear relation between the element admittance and the element temperature as shown in FIG. 21. To put it in detail, for an admittance count value Y' exceeding the threshold Ka, that is, for an element temperature higher than 625 degrees Celsius, the element temperature Ty is inferred from the admittance count value Y' by using one of the 2 straight lines with different slopes shown in FIG. 21.

To put it in detail, at the step S805, the second CPU 112 determines whether the admittance count value Y' is equal o or smaller than a predetermined value Kc which is a count value corresponding to a predetermined temperature of typically about 800 degrees Celsius in the activation-temperature range of the air-fuel ratio sensor AFS. If the admittance count value Y' is found equal to or smaller than the predetermined value Kc at the step S805, that is, if the result of the determination of the step S805 is YES, the flow of the processing proceeds to step S806 at which the second CPU 112 converts the admittance count value Y' into an element temperature Ty by calculation based on Eq. (4) given below:

$$Ty = a \times Y' + b \quad (4)$$

where the symbols a and b are constants.

If the admittance count value Y' is found greater than the predetermined value Kc at the step S805, that is, if the result of the determination of the step S805 is NO, on the other hand, the flow of the processing proceeds to step S807 at which the second CPU 112 converts the admittance count value Y' into an element temperature Ty by calculation based on Eq. (5) given below:

$$Ty = c \times Y' + d \quad (5)$$

where the symbols c and d are constants.

That is, for an admittance count value Y' in the range Ka to Kc shown in FIG. 21, an element temperature Ty is found by using Eq. (4) while, for an admittance count value Y greater than the predetermined value Kc, an element temperature Ty is found by using Eq. (5).

After the element temperature Ty has been calculated in one of the ways at the step S804, S806 or S807 described above, the flow of the processing goes on to the step S808 at which the second CPU 112 determines whether the element temperature Ty is at least equal to the target element temperature Tm. An element temperature Ty at least equal to the target element temperature Tm is interpreted to suggest that it is not necessary to heat the sensor-element unit 22 by using the heater 23. In this case, the flow of the processing continues to step S809 at which the operation to drive the heater 23 is halted. The processing is then ended. On the other hand, an element temperature Ty lower than the target element temperature Tm is interpreted to suggest that it is necessary to heat the sensor-element unit 22 by using the heater 23. In this case, the flow of the processing continues to step S810 at which the operation to drive the heater 23 is carried out. The processing is then ended.

The processing carried out at the steps S701 to S709 of the flowchart of FIG. 19 provided by this embodiment corresponds to a voltage switching means and the processing carried out at the step S711 corresponds to an admittance-value computing means. On the other hand, the processing carried out at the steps S803 to S807 of the flowchart of FIG. 20 provided by this embodiment corresponds to an element-temperature detecting means.

By virtue of the sixth embodiment described in detail above, the following effects are obtained:

(1) In an operation to detect the element resistance of the air-fuel-ratio sensor AFS in this embodiment, an element admittance Y is computed as follows:

$$Y = \Delta I / \Delta V$$

where the symbol $\Delta V$ is a transient change in oxygen-concentration-detection voltage and $\Delta I$ is a transient change in sensor current I accompanying the transient change in oxygen-concentration-detection voltage. Then, an element temperature Ty is determined by the element admittance Y.

Figure 25:
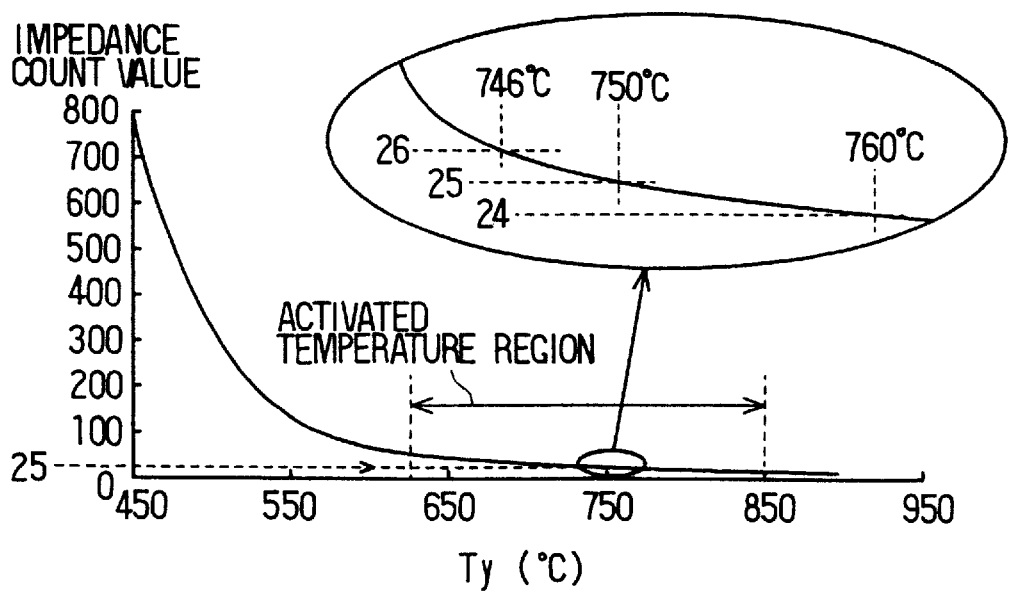
FIG. 25 is a graph showing a known relationship between the element temperature and the impedance count value.

As a result, unlike the conventional apparatus relying on a non-proportional relation between the element impedance and the element temperature shown in FIG. 25, the element temperature Ty can be found with ease from the element admittance Y. In addition, by finding an element temperature Ty from an element admittance Y using a linear relation, the accuracy of the detection of an element temperature Ty can be increased. To put it concretely, if the element admittance count value is shifted by 1 count, only a small magnitude of the shift in element temperature Ty is resulted in as shown in FIG. 24. Thus, a detection error of an element temperature Ty can be put under control. In the activation-temperature range of the air-fuel-ratio sensor AFS, a 1-count shift corresponds to a temperature shift of just 1 degree C.

(2) As described above, in the activation-temperature range of the air-fuel-ratio sensor AFS, an element temperature is found from an element admittance by using a linear relation between the element admittance and the element temperature. Thus, an element temperature can be found with a high degree of accuracy in the activation-temperature range of the air-fuel-ratio sensor AFS where a high detection accuracy is particularly required. With this embodiment, heater control in the activated state of the air-fuel-ratio sensor AFS can be implemented well. In addition, high-precision detection of the air-fuel ratio and accurate feedback control of the air-fuel ratio can be realized.

(3) The activation-temperature range of the air-fuel-ratio sensor AFS is divided into a plurality of zones and the same plurality of straight lines having slopes different from each other are assigned the zones. An element temperature is found from an element admittance in a zone by using a straight line for the zone properly selected among the straight lines which each represent the linear relation between the element temperature and the element admittance. As a result, the load of processing to find an element temperature is small in comparison with similar processing based on a conversion map. In addition, since a straight line properly selected from the straight lines having slopes different from each other is used for finding an element temperature, the detection accuracy can be further improved.

(4) A temperature below the activation-temperature range of the air-fuel-ratio sensor AFS is determined by interpolation based on map data. While it is feared that the use of a map will increase the magnitude of the processing load, the map is used occasionally only during a temporary period before the air-fuel-ratio sensor AFS gets activated. In an normal operation after the air-fuel-ratio sensor AFS has been activated, the problems with the conventional apparatus are no longer encountered.

(5) If the level of the voltage signal Vi appearing at one end of the shunt resistor R3 and supplied to the input terminal Ch2 of the first CPU111 is higher than a predetermined reference level, that is, the center level of a range of voltages output by the operational amplifier OP1, the variable electric potential of the oxygen-concentration-detection voltage is lowered, but if the level of the voltage signal Vi is lower than the reference level, on the other hand, the variable electric potential of the oxygen-concentration-detection voltage is raised. In this embodiment, the reference level is a middle value of a range of voltages output by the operational amplifier OP1, the variable electric potential is the potential of a voltage appearing at one end of the shunt resistor R3 connected to the plus-side terminal AF+ of the air-fuel-ratio sensor AFS and the predetermined voltage signal is a voltage appearing at the other end of the shunt resistor R3 or the input voltage Vi supplied to the input terminal Ch1 of the first CPU 111.

In addition, by correctly determining whether to lower or raise the variable electric potential of the oxygen-concentration-detection voltage in accordance with the level of the input voltage Vi as described above, the first CPU 111 is capable of correctly switching the variable electric potential from a level to another without knowing whether the current air-fuel ratio is on the rich or lean side. Since the input voltage Vi is determined by the performance of the operational amplifier OP1, the switching performance is not affected by the aging of the air-fuel-ratio sensor AFS and inherent characteristic variations from sensor to sensor.

(6) Furthermore, in this embodiment, a dual-CPU system is built in the on-board ECU 101 wherein the first CPU 111 detects an element admittance while the second CPU 112 finds an element temperature from the element admittance detected by the first CPU 111. In addition, the first CPU 111 is connected to the second CPU 112 so that the CPUs 111 and 112 are capable of communicating with each other by DMA transmission. To be more specific, the first CPU 111 transfers an element admittance count value obtained as a result of calculation to the second CPU 112 as fewer bytes of data than that resulting from computation of the element admittance value. In such a configuration, it is possible to transfer few bytes of information on an element resistance while maintaining the accuracy a required portion of the information. As a result, there has been exhibited an effect of substantial reduction of a load borne during the DMA transmission.

It should be noted that the embodiment may be modified as follows.

In the embodiment described above, 2 straight lines which have different gradients and each represent a linear relation between the element admittance and the element temperature are set in the activation-temperature region of the air-fuel-ratio sensor AFS, that is, a region of element temperatures higher than 625 degrees Celsius, as shown in FIG. 21 and each used to find an element temperature from an element admittance. It should be noted, however, that a straight line or 3 or more straight lines which have different gradients and each represent a linear relation between the element admittance and the element temperature can also be used. As for element temperatures below the activation-temperature region of the air-fuel-ratio sensor AFS, approximation based on a straight line can also be adopted in place of the conversion map shown in FIG. 22. On the other hand, a conversion map can also be used for element temperatures in the activation-temperature region of the air-fuel-ratio sensor AFS as is the case with the conventional apparatus.

In addition, detection of an element temperature from an element admittance can be limited to the activation-temperature zone of the air-fuel-ratio sensor AFS. That is, the demand for high-precision detection of an element temperature outside the activation-temperature zone of the air-fuel-ratio sensor AFS is low. Thus, the conventional technique for finding an element temperature from an element impedance can be adopted for a zone other than the activation-temperature zone of the air-fuel-ratio sensor AFS. In this case, for the activation-temperature zone of the air-fuel-ratio sensor AFS, an element temperature is detected from an element admittance while, for a zone other than the activation-temperature zone, an element temperature is detected from an element impedance.

In the embodiment described above, the ON/OFF control of the heater 23 is executed in accordance with a result of comparison of a detected element temperature Ty with a target element temperature Tm. It should be noted that a change can be made to such a configuration. For example, the amount of electric conduction of the heater 23 such as the duty cycle or the power supplying capacity of the heater 23 is controlled to eliminate a deviation of a detected element temperature Ty from a target element temperature Tm. That is, feedback control of the element temperature is implemented. In this case, by applying the present invention, the control precision of the feedback control of the element temperature can be improved.

In this embodiment, the first CPU 111 detects an element admittance, that is, the reciprocal of the element resistance, while the second CPU 112 finds an element temperature from the element admittance detected by the first CPU 111. It is worth noting, however, that one of the CPUs 111 and 112 can also be used to carry out both the pieces of processing.

In the embodiment described above, an element temperature Ty of the air-fuel-ratio sensor AFS is detected and the element temperature Ty obtained as a result of detection is used in control of the heater 2 wherein the amount of electrical conduction of the heater 23 is found from a characteristic representing a relation between the amount electrical conduction of the heater 23 and the element temperature which is stored in advance. In addition, the detected element temperature Ty can also be used for other purposes such as determination of a deterioration degree of the air-fuel-ratio sensor AFS. For example, if the detected element temperature Ty can not be brought to a target element temperature Tm even if the amount of electrical conduction of the heater 23 is set according to the stored characteristic, the air-fuel-ratio sensor ARS may be determined to have deteriorated.

As described above, the embodiment employs an air-fuel-ratio sensor AFS of the limit-current type having a shape resembling a cup as an oxygen concentration sensor. It should be noted, however, that an air-fuel-ratio sensor of the stacked-layer type may also be employed. By the way, an air-fuel-ratio sensor of the stacked-layer type offers merits such as an excellent rising-temperature characteristic as is generally known.

In addition, the present invention may also be applied to apparatuses other than an air-fuel-ratio detecting apparatus. For example, the present invention may also be applied to a gas-concentration detecting apparatus employing a gas-concentration sensor capable of detecting the concentration of a specific gas component such as NOx, HC or CO. By adopting the technique provided by the embodiment in such a gas-concentration detecting apparatus, the detection accuracy of the element temperature and, hence, the detection accuracy of the concentration of the specific gas is improved.

Although the present invention has been described in connection with the preferred embodiments thereof with reference to the accompanying drawings, it is to be noted that various changes and modifications will be apparent to those skilled in the art. Such changes and modifications are to be understood as being included within the scope of the present invention as defined in the appended claims.

What is claimed is:

1. Apparatus for detecting the resistance of an oxygen concentration sensor, said apparatus comprising:
   voltage applying means for applying a voltage to the oxygen concentration sensor for the purpose of generating a sensor current related to oxygen concentration of a gas;

applied-voltage changing means for changing the voltage applied to the oxygen concentration sensor for the purpose of detecting its resistance;

first current detecting means for detecting the sensor current before the voltage is changed by said applied-voltage changing means;

second current detecting means for detecting the sensor current when a predetermined period elapses after the voltage to the oxygen sensor is changed by said applied-voltage changing means; and element-resistance-component calculating means for calculating resistance of the oxygen concentration sensor based on a difference between the sensor current detected by said first current detecting means and the sensor current detected by said second current detecting means;

wherein said voltage applying means further includes:
   an output circuit for applying a voltage to the oxygen concentration sensor;
   a constant-voltage circuit for inputting a first predetermined constant voltage to an input terminal of said output circuit through an output resistor; and
   a first voltage switching circuit including a first voltage dividing resistor and a first switching device, which are connected in series between a signal line from said output resistor to said input terminal of said output circuit and a first terminal having a second predetermined voltage; and wherein said applied-voltage changing means changes the voltage applied to the oxygen concentration sensor by said voltage applying means by switching said first switching device.

2. Apparatus as in claim 1, wherein:

said voltage applying means further includes a second voltage switching circuit having a second voltage dividing resistor and a second switching device, which are connected in series between said signal line from said output resistor to said input terminal of said output circuit and a second terminal having a third predetermined voltage; and said applied-voltage changing means changes the voltage applied by said voltage applying means to the oxygen concentration sensor by switching said first and second switching devices such that the voltage applied by said voltage applying means to the oxygen concentration sensor is changed respectively in a positive direction and a negative direction.

3. Apparatus as in claim 2, wherein:

said constant-voltage circuit outputs said first predetermined constant voltage for detection of oxygen concentration;

said second predetermined voltage is higher than said first constant voltage;

said third predetermined voltage is lower than said first constant voltage;

the voltage applied by said voltage applying means to the oxygen concentration sensor is changed in a positive direction by turning on said first switching device; and the voltage applied by said voltage applying means to the oxygen concentration sensor is changed in a negative direction by turning on said second switching device.

4. An oxygen concentration detecting apparatus using an oxygen concentration sensor which generates a sensor current according to an oxygen concentration of a gas by applying a voltage to the sensor through first and second terminals of the sensor, said apparatus comprising:

first voltage applying means for applying a first voltage to the first herminal of the oxygen concentration sensor;

second voltage applying means for applying a second voltage to the second terminal of the oxygen concentration sensor;

applied-voltage changing means for changing said first voltage for the purpose of detecting resistance of the oxygen concentration sensor;

first current detecting means for detecting the sensor current before said first voltage is changed by said applied-voltage changing means;

oxygen concentration calculating means for calculating oxygen concentration of a gas based on the sensor current detected by said first current detecting means;

second current detecting means for detecting the sensor current of the oxygen concentration sensor when a predetermined period elapses after said first voltage is changed by said applied-voltage changing means; and resistance-component calculating means for calculating resistance of the oxygen concentration sensor based on a difference between the sensor current detected by said first current detecting means and the sensor current detected by said second current detecting means;

wherein said first voltage applying means further includes;
   an output circuit for applying a voltage to the oxygen concentration sensor;
   a constant-voltage circuit for inputting a first predetermined constant voltage to an input terminal of said output circuit through an output resistor; and
   a first voltage switching circuit including a first voltage dividing resistor and a first switching device, which are connected in series between a signal line from said output resistor to said input terminal of said output circuit and a first terminal having a second predetermined voltage; and wherein said applied-voltage changing means changes said first voltage by switching said first switching device.

5. Apparatus as in claim 4, wherein:

said apparatus includes voltage generating means for generating a first voltage and a second voltage by being connected in series between a battery voltage and a ground voltage such that said battery voltage is divided between said first voltage and said second voltage;

said first voltage generated by said voltage generating means is input to said constant voltage circuit;

said first voltage, input to said constant voltage circuit, is output from said constant voltage circuit as said first predetermined constant voltage;

said applied-voltage changing means changes said first voltage by turning on said first switching device;

said second voltage generated by said voltage generating means is input to said second voltage applying means; and said second voltage, input to said second voltage applying means, is output to the second terminal of the oxygen concentration sensor.

6. Apparatus as in claim 5, wherein:

said first voltage applying means includes a second voltage switching circuit including a second voltage dividing resistor and a second switching device, which are connected in series between said signal line from said output resistor to said input terminal of said output circuit and a second terminal having a third predetermined voltage;

said second predetermined voltage is higher than said first voltage;

said third predetermined voltage is lower than said first voltage; and said applied-voltage changing means changes said first voltage by switching said first and second switching devices such that said first voltage is respectively changed in a positive direction and a negative direction.

7. Apparatus as in claim 4, wherein said second voltage applying means is capable of changing said second voltage.

8. Apparatus as in claim 7, wherein:

said first voltage applying means includes a second voltage switching circuit including a second voltage dividing resistor and a second switching device, which are connected in series between said signal line from said output resistor to said input terminal of said output circuit and a second terminal having a third predetermined voltage; and said applied-voltage changing means changes said first voltage by switching said first and second switching devices such that said first voltage is respectively changed in a positive direction and a negative direction.

9. Apparatus as in claim 8, wherein:

said constant-voltage circuit outputs said first voltage as said first predetermined constant voltage;

said second predetermined voltage is higher than said first voltage;

said third predetermined voltage is lower than said first voltage;

said first voltage is changed in a positive direction by turning on said first switching device; and said first voltage is changed in a negative direction by turning on said second switching device.

10. Apparatus for measuring resistance of an oxygen concentration sensor which generates a sensor current according to an oxygen concentration of a gas by applying voltage to the sensor through first and second terminals of the sensor, said apparatus comprising:

first voltage applying means for applying a first voltage to the first terminal of the oxygen concentration sensor;

second voltage applying means for applying a second voltage to the second terminal of the oxygen concentration sensor;

applied-voltage changing means for changing said first voltage for the purpose of detecting resistance of the oxygen concentration sensor;

first current detecting means for detecting the sensor current when the oxygen concentration sensor is in a steady state;

second current detecting means for detecting the sensor current of the oxygen concentration sensor when a predetermined period elapses after said first voltage is changed by said applied-voltage changing means;

resistance-component calculating means for calculating resistance of the oxygen concentration sensor based on a difference between the sensor current detected by said first current detecting means and the sensor current detected by said second current detecting means;

wherein said first voltage applying means further includes:

multiple-voltage output means for outputting a plurality of voltages including said first voltage; and voltage selecting means for selecting one of said outputted plurality of voltages to apply to said first terminal of the sensor based on a selection signal from said applied-voltage changing means; and wherein said applied-voltage changing means changes said first voltage by changing said selection signal.

11. Apparatus as in claim 10, wherein said first current detecting means detects the sensor current before said first voltage is changed by said applied-voltage changing means.

12. Apparatus as in claim 10, wherein:

said multiple-voltage output means selectively outputs one of said first voltage, a higher voltage higher than said first voltage and a lower voltage lower than said first voltage; and said applied-voltage changing means selectively changes said first voltage to one of said higher voltage higher than said first voltage and said lower voltage lower than said first voltage by changing said selection signal.

13. Apparatus as in claim 10, wherein said multiple-voltage output means includes a digital/analog converter having a plurality of output terminals for outputting said plurality of voltages respectively.

14. Apparatus as in claim 10, wherein said second voltage applying means has second voltage changing means for changing said second voltage.

15. Apparatus for detecting resistance of an oxygen concentration sensor which generates a sensor current according to an oxygen concentration of a gas by applying a voltage to the sensor through first and second terminals of the sensor, said apparatus comprising:

first voltage applying means for applying a first voltage to the first terminal of the oxygen concentration sensor;

second voltage applying means for applying a second voltage to the second terminal of the oxygen concentration sensor;

applied-voltage changing means for changing said first voltage for the purpose of detecting resistance of the oxygen concentration sensor;

first current detecting means for detecting the sensor current when the oxygen concentration sensor is in a steady state;

second current detecting means for detecting the sensor current of the oxygen concentration sensor when a predetermined period elapses after said first voltage is changed by said applied-voltage changing means;

resistance-component calculating means for calculating resistance of the oxygen concentration sensor based on a difference between the sensor current detected by said first current detecting means and the sensor current detected by said second current detecting means;

wherein said first voltage applying means further includes:

a digital/analog converter having first and second output terminals; and voltage selecting means for selectively applying one of voltages outputted from said first and second output terminals of said digital/analog converter to the first terminal of the sensor based on a selection signal from said applied-voltage changing means; and wherein said applied-voltage changing means comprises:

a first means outputting a first command signal to said digital/analog converter such that said digital/analog converter outputs said first voltage from said first output terminal and a third voltage from said second output terminal, and outputting said selection signal to said voltage selecting means such that said first voltage from said first output terminal is applied to the first terminal of the sensor, before changing said first voltage;

a second means outputting a second command a signal to said digital/analog converter such that a fourth voltage, which has an opposite pole to said third voltage and has the same absolute value based on said first voltage, is outputted from said first output terminal after changing said selection signal such that said third voltage outputted from said second output terminal is applied to the first terminal of the sensor;

a third means outputting a third command signal to said digital/analog converter such that said first voltage is outputted from said second output terminal after changing said selection signal such that said fourth voltage outputted from said first output terminal is applied to the first terminal of the sensor when a first predetermined period, which is longer than a delayed period from outputting said second command signal to a voltage change at said first output terminal, elapses; and a fourth means changing said selection signal such that said first voltage outputted from said second output terminal is applied to the first terminal of the sensor when a second predetermined period, which is longer than a delayed period from outputting said third command signal to a voltage change at said second output terminal, elapses.

16. Apparatus as in claim 15, wherein said first current detecting means detects the sensor current immediately prior to an operation carried out by said applied-voltage changing means to change said first voltage.

17. Apparatus as in claim 15, wherein said second voltage applying means has second voltage changing means for changing said second voltage.

* * * * *